(12) United States Patent
Maras et al.

(10) Patent No.: US 9,221,829 B2
(45) Date of Patent: Dec. 29, 2015

(54) SYNTHESIS OF TRIAZOLOPYRIMIDINE COMPOUNDS

(75) Inventors: Nened Maras, Ljubljana (SI); Borut Zupancic, Ljubljana (SI)

(73) Assignee: Lek Pharmaceuticals d.d. (SI)

( * ) Notice: Subject to any disclaimer, the term of this patent is extended or adjusted under 35 U.S.C. 154(b) by 0 days.

(21) Appl. No.: 14/344,960

(22) PCT Filed: Sep. 14, 2012

(86) PCT No.: PCT/EP2012/068068
§ 371 (c)(1),
(2), (4) Date: Jul. 31, 2014

(87) PCT Pub. No.: WO2013/037942
PCT Pub. Date: Mar. 21, 2013

(65) Prior Publication Data
US 2015/0005498 A1    Jan. 1, 2015

(30) Foreign Application Priority Data

Sep. 14, 2011 (EP) .................................. 11181280
Nov. 10, 2011 (EP) .................................. 11188602
Dec. 23, 2011 (EP) .................................. 11195581

(51) Int. Cl.
| | |
|---|---|
| *C07D 471/00* | (2006.01) |
| *C07D 487/00* | (2006.01) |
| *C07D 491/00* | (2006.01) |
| *C07D 487/04* | (2006.01) |
| *C07D 405/12* | (2006.01) |
| *C07D 239/47* | (2006.01) |
| *C07D 239/69* | (2006.01) |
| *C07C 217/52* | (2006.01) |
| *C07D 239/48* | (2006.01) |

(52) U.S. Cl.
CPC ............ *C07D 487/04* (2013.01); *C07C 217/52* (2013.01); *C07D 239/47* (2013.01); *C07D 239/48* (2013.01); *C07D 239/69* (2013.01); *C07D 405/12* (2013.01)

(58) Field of Classification Search
None
See application file for complete search history.

(56) References Cited

FOREIGN PATENT DOCUMENTS

| | | |
|---|---|---|
| WO | 0034283 | 6/2000 |
| WO | 0119826 A2 | 3/2001 |
| WO | 0136421 A1 | 5/2001 |
| WO | 0192263 A1 | 12/2001 |
| WO | 2010030224 A1 | 3/2010 |
| WO | 2011017108 A2 | 2/2011 |

OTHER PUBLICATIONS

Hong Ye, et. al., "Carba-nucleosides as Potent Antagonists of the Adenosine 5'-Diphosphate (ADP) Purinergic Receptor (P2Y12) on Human Platelets," ChemMedChem, vol. 3, No. May 19, 2008, pp. 732-736, XP55011415, ISSN: 1860-7179, DOI: 10.1002/cmdc. 200700310.

Springthorpe, Brian, et.al, "From ATP to AZD6140: The Discovery of an Orally Active Reversible P2Y12 receptor Antagonist for the Prevention of Thrombosis," ScienceDirect, Bioorganic & Medicinal Chemistry Letters 17 (2007) 6013-6018 (www.sciencedirect.com).

*Primary Examiner* — Jeffrey H Murray
(74) *Attorney, Agent, or Firm* — Luedeka Neely Group, P.C.

(57) ABSTRACT

The present invention relates to the field of organic synthesis and describes the synthesis of specific triazolopyrimidine compounds and intermediates thereof as well as related derivatives, suitable for the preparation of Ticagrelor (TCG).

3 Claims, No Drawings

SYNTHESIS OF TRIAZOLOPYRIMIDINE COMPOUNDS

This application is a national phase entry of PCT International application number PCT/EP2012/068068, filed Sep. 14, 2012. This application also claims the benefit of the earlier filing dates of: (1) EP11181280.6, filed Sep. 14, 2011; (2) EP11188602.4, filed Nov. 10, 2011; and (3) EP1119558.1, filed Dec. 23, 2011.

The present invention relates to the field of organic synthesis, in particular to the synthesis of specific triazolopyrimidine compounds and intermediates thereof as well as related derivatives.

An important triazolopyrimidine compound is ticagrelor (TCG; Brilinta®; 3-[7-[[(1R,2S)-2-(3,4-difluorophenyl)cyclopropyl]amino]-5-(propylthio)-3H-1,2,3-triazolo[4,5-d]pyrimidin-3-yl]-5-(2-hydroxyethoxy)-(1S,2S,3R,5S)-1,2-cyclopentanediol) having the following structural formula.

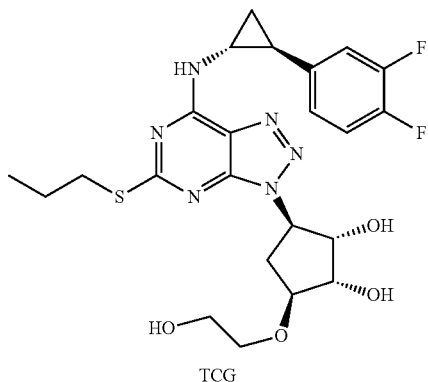 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

TCG

Ticagrelor shows pharmaceutical activity by functioning as a P2Y12 receptor antagonist and thus is indicated for the treatment or prevention of thrombotic events, for example stroke, heart attack, acute coronary syndrome or myocardial infection with ST elevation, other coronary artery diseases and arterial thrombosis as well as other disorders related to platelet aggregation (WO 00/34283).

The synthesis of ticagrelor (TCG) is demanding. There are five to six known synthetic variants, which are described in the basic patent application WO 00/34283, an improved one in patent application WO 01/92263, and a further improved one in patent application WO 10/030224 respectively derived from the originator AstraZeneca, while two are published in a "deutero" patent application WO 11/017108 of Auspex Pharmaceuticals. Further, there is one synthetic path published in a scientific journal (*Bioorg. Med. Chem. Lett.* 2007, 17, 6013-6018).

The first synthesis of TCG as described in WO 00/34283 is depicted in scheme 1 below.

Scheme 1: Synthesis of ticagrelor (TCG) as described in WO 00/34283.

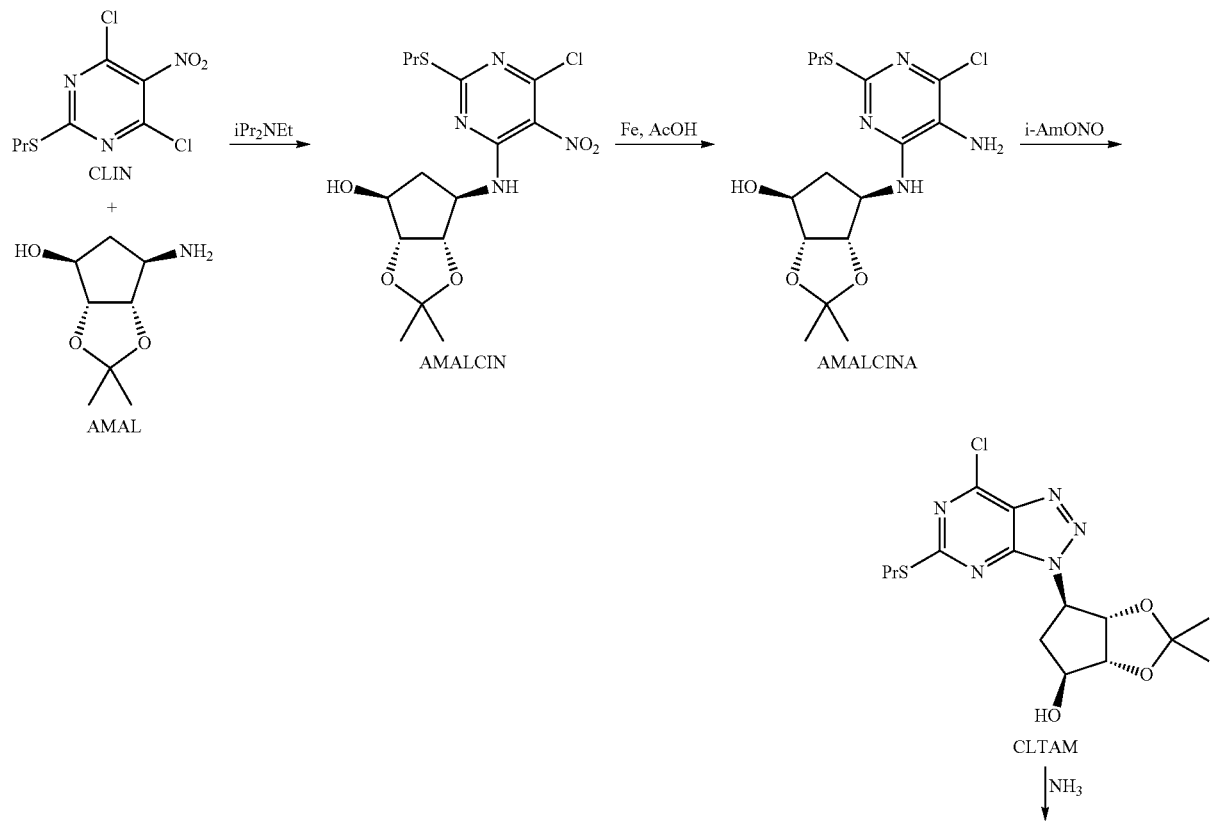

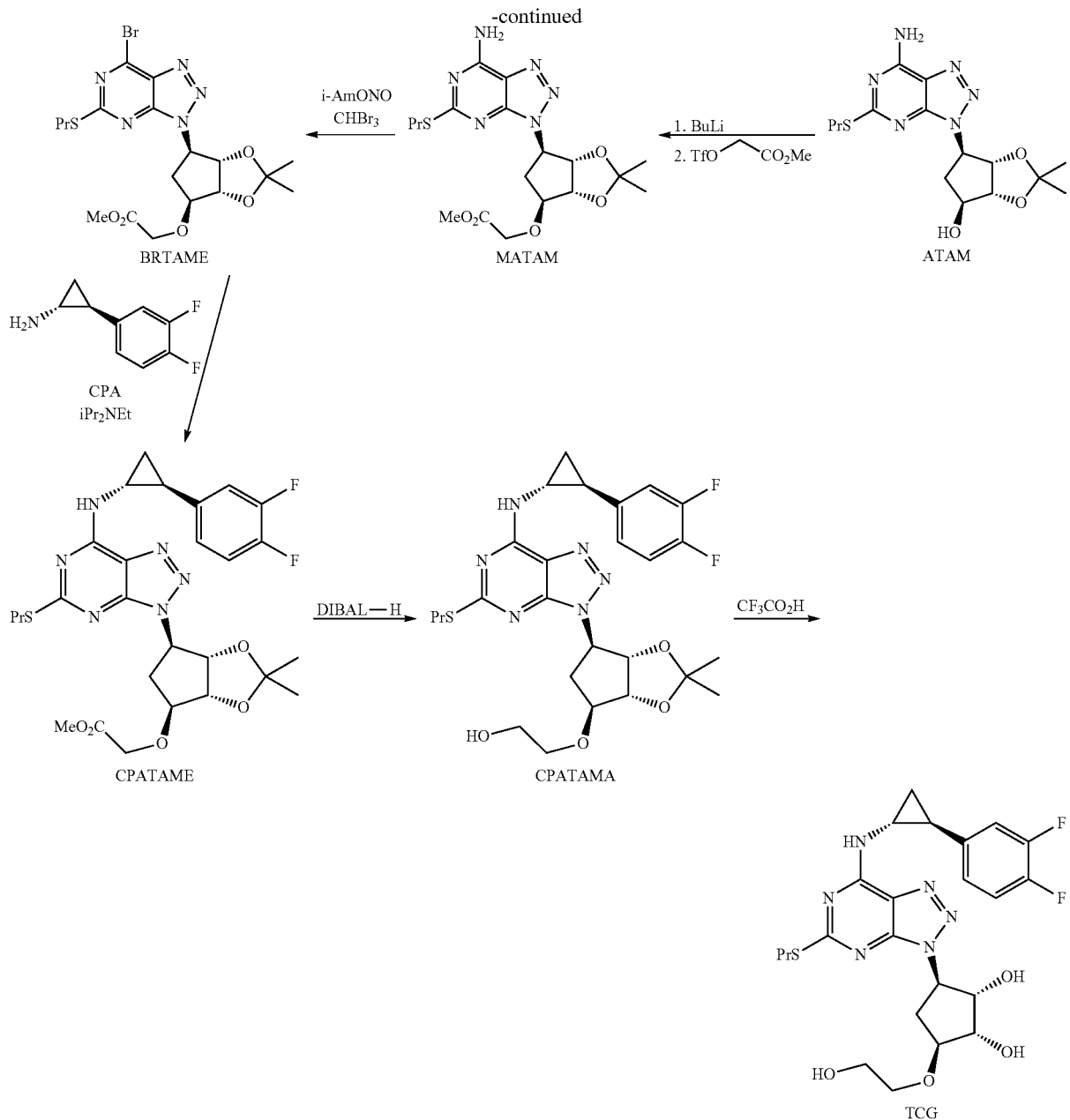

This nine step synthesis of ticagrelor (TCG) as described in WO 00/34283 (Scheme 1) starts with a reaction between CLIN and AMAL. In the presence of diisopropylethylamine (iPr$_2$NEt) AMALCIN is formed, which is in then reduced with iron (Fe) in acetic acid to AMALCINA. In the next step CLTAM is formed using isopentyl nitrite (iAmONO). Next, ATAM was prepared using ammonia, and side chain was introduced (MATAM) using n-butyllithium and methyl 2-(((trifluoromethyl)sulfonyl)oxy)acetate, which was previously prepared by reaction between methyl glycolate and triflic anhydride. In next step BRTAME is formed using iAmONO and CHBr$_3$, followed by the aromatic nucleophilic substitution of Br with CPA in the presence of iPr$_2$NEt to form CPATAME. This is then reduced to CPATAMA using DIBAL-H. Deprotection of diol group in the presence of trifluoroacetic acid in the final step leads to TCG. This synthetic path is very long (9 steps, not including reagents preparation) and uses toxic compounds like CHBr$_3$, triflic anhydride, and methyl 2-(((trifluoromethyl)sulfonyl)oxy)acetate. The introduction of the methoxycarbonylmethyl group (reaction from ATAM to MATAM) is very difficult due to poor chemo-selectivity, as the amino group also reacts with 2-(((trifluoromethyl)sulfonyl)oxy)acetate. An improved synthesis of ticagrelor (TCG) is described in WO 01/92263 (see Scheme 2). In this process the hydroxyethyl side chain is introduced at the beginning of the synthesis by a three step reaction path from AMAL to AMALA, which is then reacted with CLINA (prepared from CLIDA) in presence of triethylamine (Et$_3$N) to form AMALCINAA. The triazole ring of CLTAM is formed with NaNO$_2$ in acetic acid, and then Cl is exchanged with CPA to form CPATAMA. In the final step TCG is prepared via deprotection using HCl.

This improved process still has substantial length (7-8 steps). In AMALA synthesis the benzyloxycarbonyl protection (Cbz) is used, which is then removed in the third step using hydrogenation with Pd/C as a catalyst. Hydrogenation with Pt/C as a catalyst is also used in the reduction of CLIDA to CLINA.

Another improved synthetic path is described in WO 10/030224 (Scheme 3). The key steps in this process are reduction of CLIN to CLINA or AMALCINO to AMALCINAA using hydrogen gas and platinum vanadium catalyst.

Scheme 2: Synthesis of ticagrelor (TCG) as described in WO 01/92263.

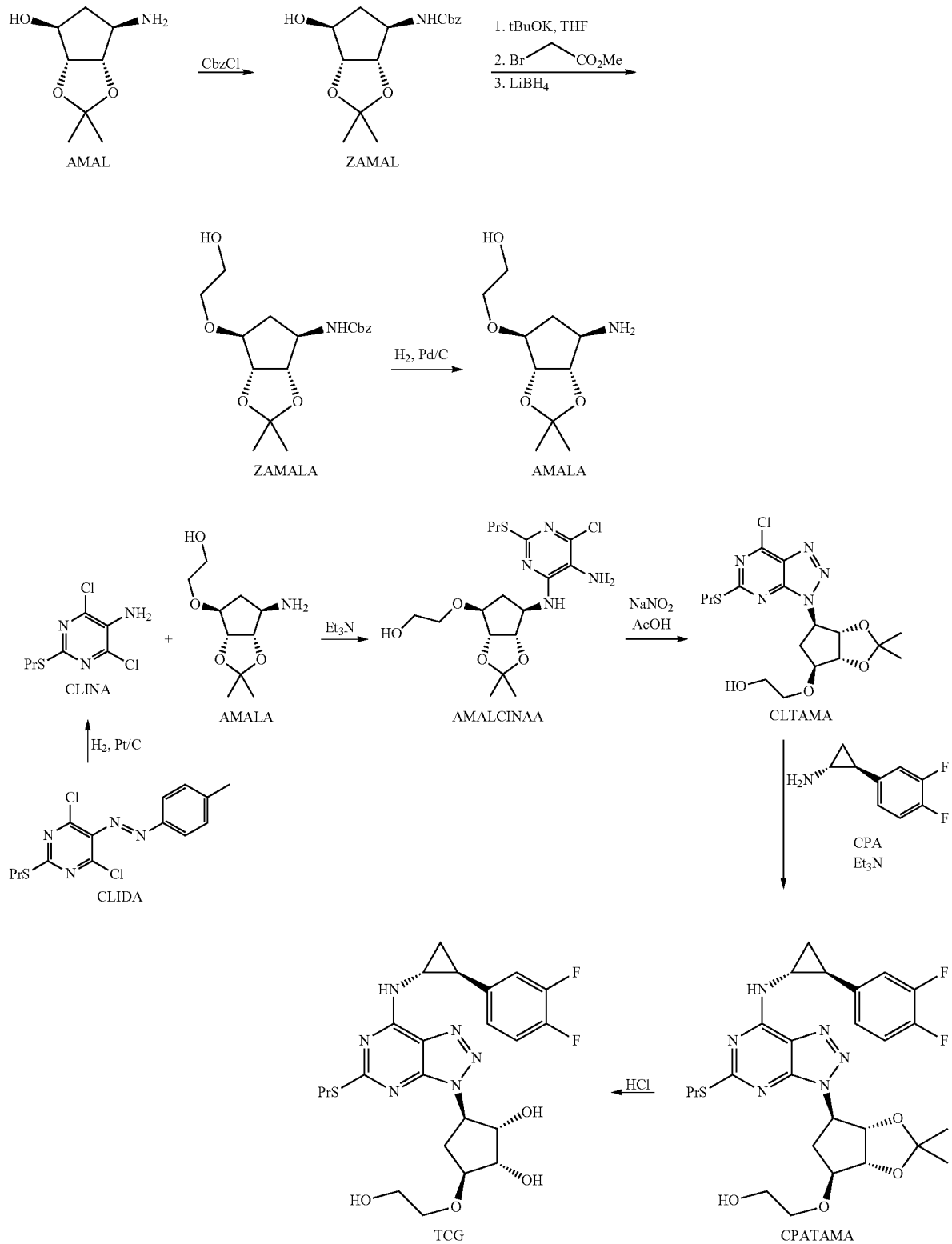

The introduction of the hydroxyethyl side chain to AMAL to form AMALA, cyclization, substitution of Cl atom of CLTAMA with CPA and final acidic deprotection are the same as in WO 01/92263.

This further improved process to TCG has 8 reaction steps. Like in WO 01/92263, there are used the Cbz protecting group and heavy metals as catalysts like Pd, Pt and/or V.

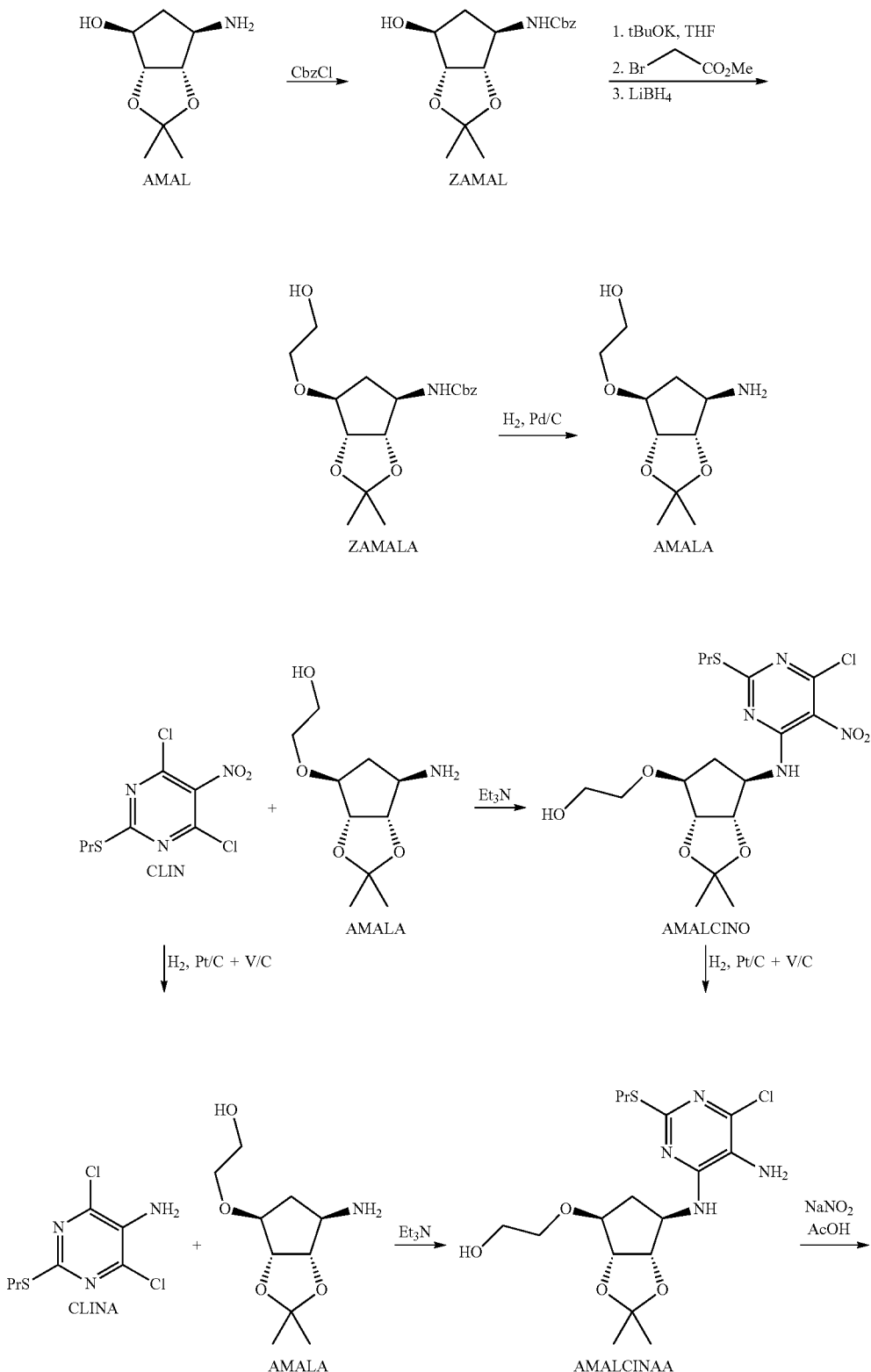

Scheme 3: Syntheses of ticagrelor (TCG) as described in WO 10/030224.

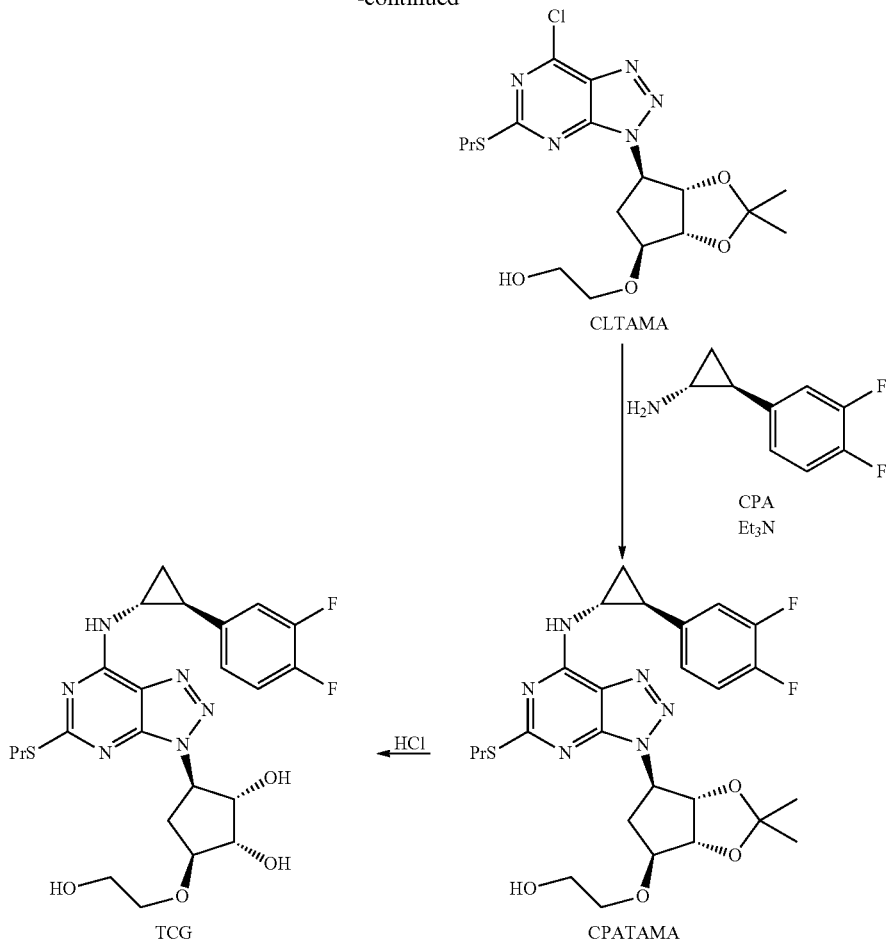
AstraZeneca published a synthetic path (Scheme 4) to ticagrelor (TCG) in *Bioorg. Med. Chem. Lett.* 2007, 17, 6013-6018. Intermediates in this process are similar to those described in WO 01/92263. There is difference in formation of triazolo ring of CLTAMA where iAmONO is used, and difference in deprotection in the last step.
Scheme 4: Synthesis of ticagrelor (TCG) as described in *Bioorg. Med. Chem. Lett.* 2007, 17, 6013-6018.
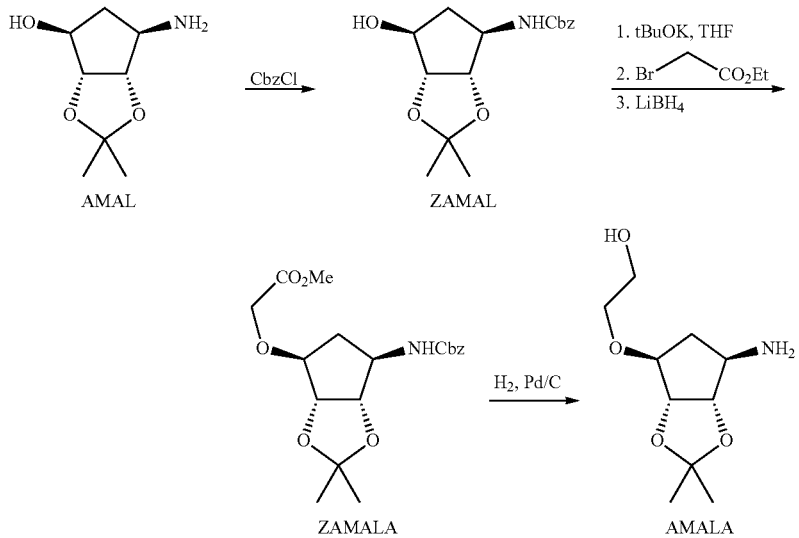

-continued

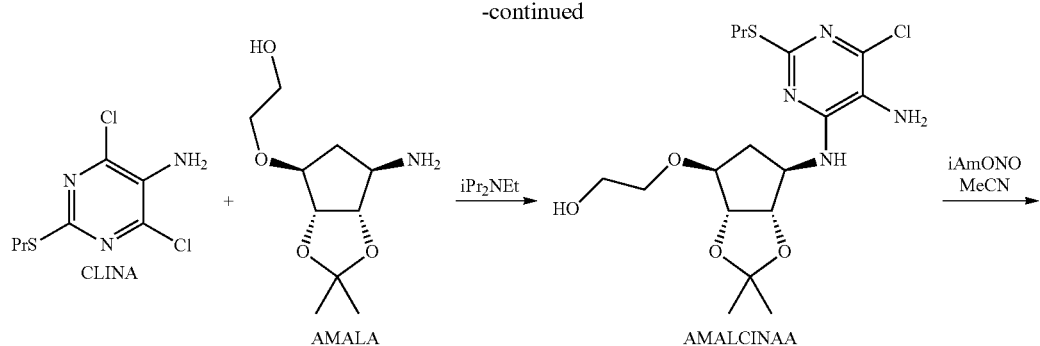

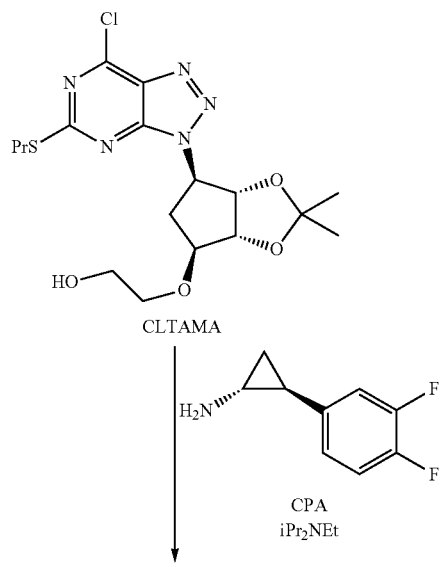

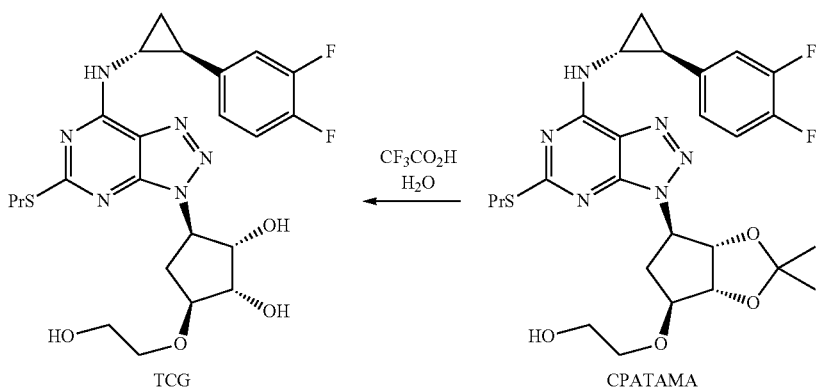

Another synthetic variant (Scheme 5) to ticagrelor (TCG) is described in WO 11/017108 by Auspex Pharmaceuticals. In nine step synthesis they prepared AMALE through deprotection of ZAMALE using hydrogen gas and Pd/C, which was then reduced to AMALA with LiAlH$_4$. AMALCINO was prepared without presence of base, further steps are similar to those published in WO 01/92263.

Still another synthetic variant (Scheme 6) to obtain ticagrelor with deuterated hydroxyethyl group (TCGD) is also described in WO 11/017108 by Auspex Pharmaceuticals.

Scheme 5: Synthesis of ticagrelor (TCG) as described in "deutero" patent WO 11/017108.
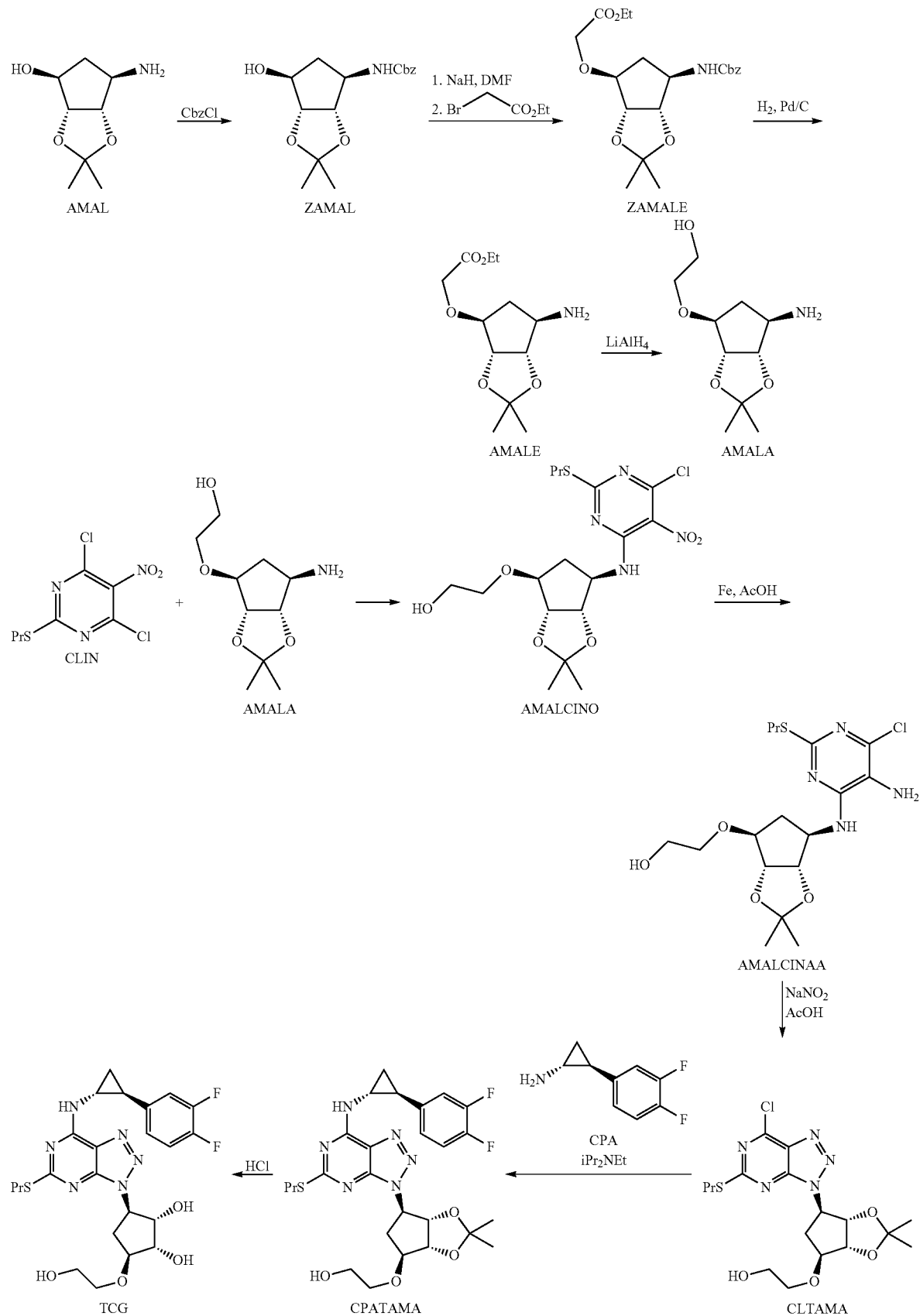

Scheme 6: Synthesis of ticagrelor with deuterated hydroxyethyl group (TCGD) aas described in "deutero" patent WO 11/017108.
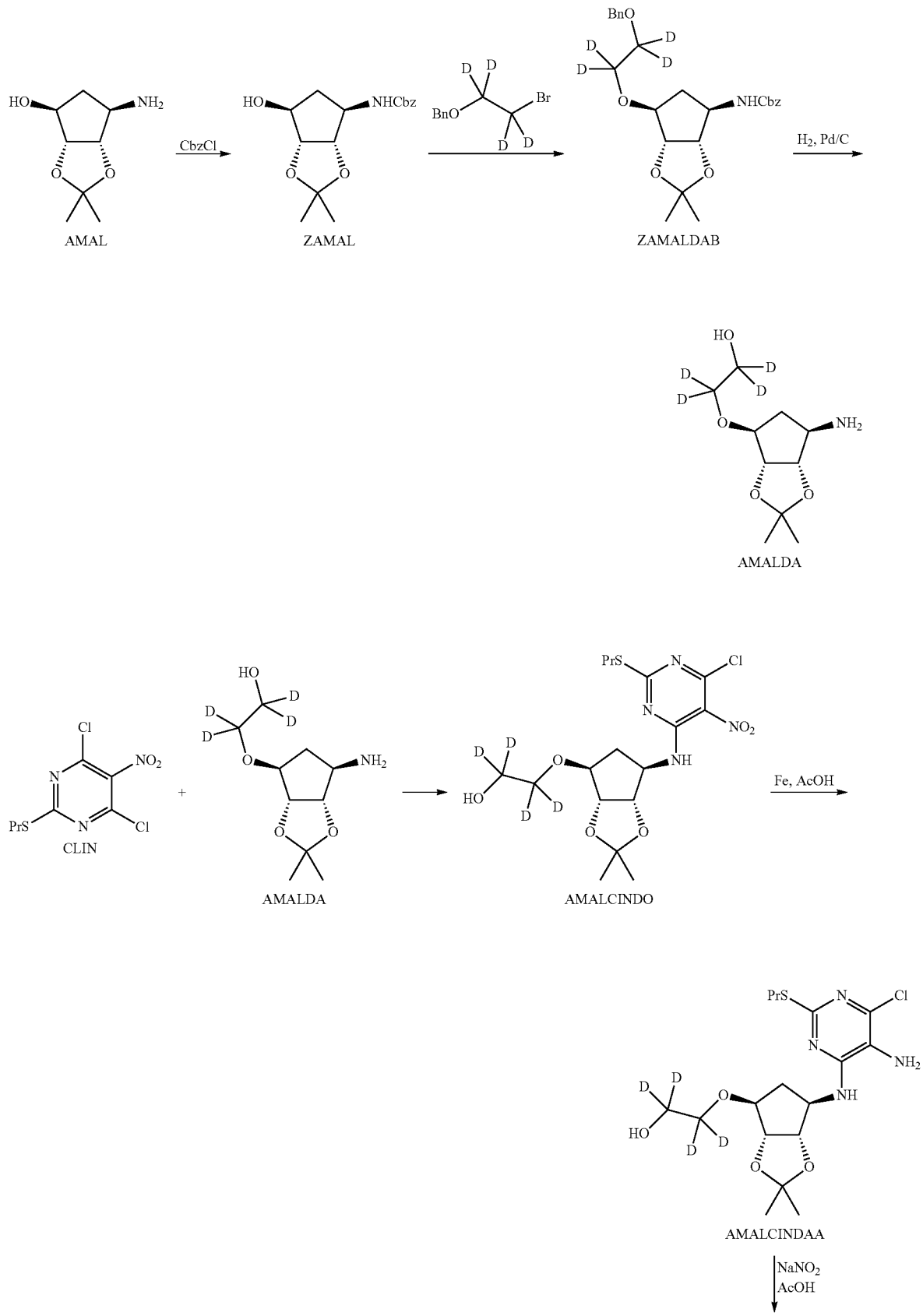

-continued

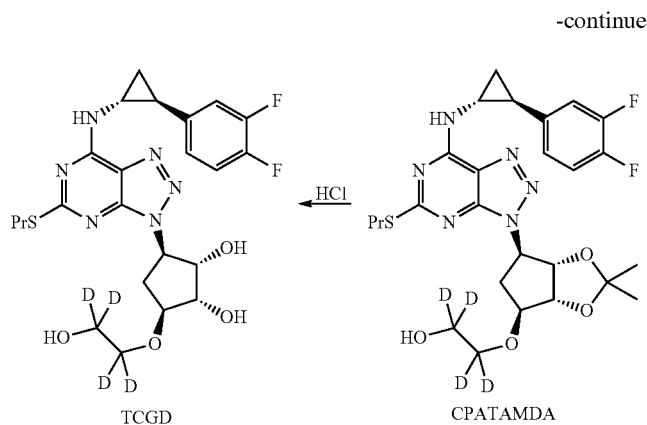

TCGD

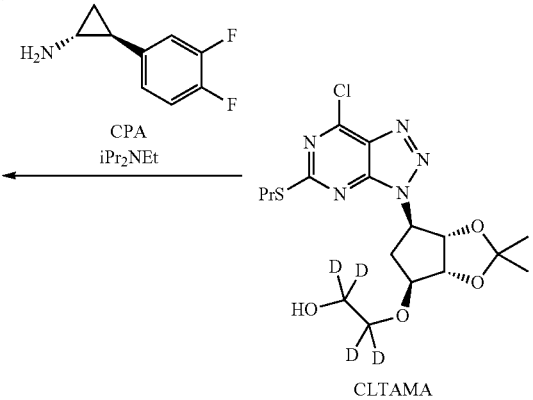

CPATAMDA  CLTAMA

As becomes apparent from the above, a major drawback of the hitherto known synthesis schemes for the preparation of ticagrelor is that the synthesis is long.

SUMMARY OF THE INVENTION

The object of the present invention was to provide an industrially applicable and economically improved process for obtaining ticagrelor.

The present invention provides a process for the preparation of a compound of formula Va or Vb Va

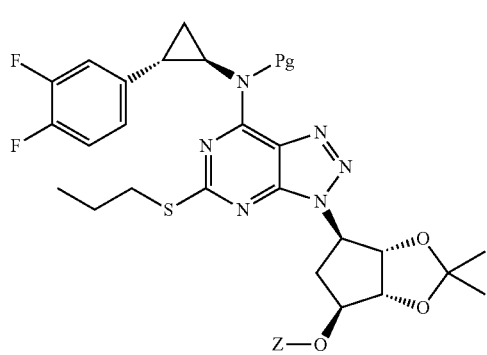

Vb

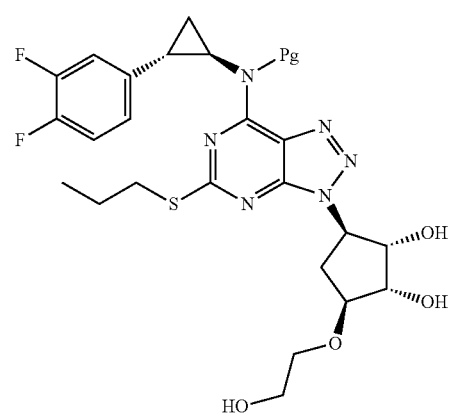

wherein Pg is an amino protecting group, and Z is hydrogen, hydroxyethyl or a group convertible to hydroxyethyl, the process comprising the steps of:
(i) reacting a compound of formula II'

II'

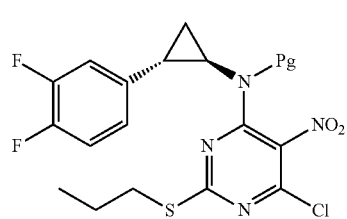

wherein Pg is defined as above, with a compound of the formula VI or VII

VI

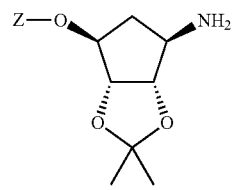

VII

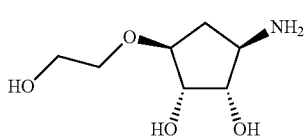

wherein Z is defined as above, to obtain a compound of formula IIIa' or IIIb', respectively IIIa'

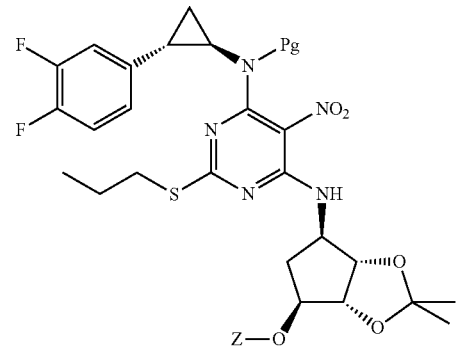

IIIb'

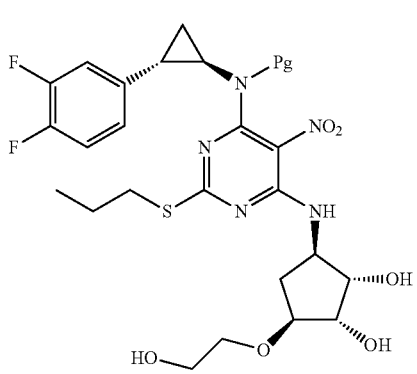

wherein Pg and Z are as defined above,
(ii) reducing the nitro group in the compound of formula IIIa' or IIIb' to an amino group to obtain a compound of formula IVa' or IVb', respectively, and IVa'

IVb'

(iii) nitrosation of the compound of formula IVa' or IVb' to obtain the compound of formula Va or Vb, respectively.

The process defined above allows for preparation or synthesis of ticagrelor with an industrially applicable and economically improved process. Preferred embodiments will be described below. The present invention further provides novel compounds that are highly useful as key intermediates in the preparation or synthesis of ticagrelor.

DESCRIPTION OF THE INVENTION AND OF PREFERRED EMBODIMENTS

Aspects, advantageous features and preferred embodiments of the present invention will be described in further detail below, noting however that such aspects, advantages features as well as embodiments and examples are presented for illustrative purposes only and shall not limit the invention in any way.

The introduction of a protective group on the amino group of the cyclopropane ring is a significant point of the present invention, which is a novel feature common to the key steps of the synthetic preparation as well as to the intermediate compounds mentioned above. This crucial point significantly distinguishes over every prior art synthesis in which a substitution reaction of the pyrimidine ring with cyclopentane is carried out first, and only then the triazole ring is created with a final substitution with the cyclopropane ring. This sequence of the reaction steps in the prior art solutions needs to be followed exactly, otherwise a selectivity of the triazole ring formation is eliminated, or wrong triazole systems are obtained. Introduction of the protective group on the amino group of cyclopropane ring according to the present invention however enables selectivity of the triazole ring formation regardless of the step conducted after the protective group is introduced. The synthesis and the special types of intermediate compounds are already suitably protected for the selective introduction of the cyclopentane ring and/or the selective introduction of the hydroxyethyl group.

In particular, the process according to the present invention reduces the number of the required reaction steps. It is possible to proceed in a short 3-4 step process, contrary to prior art processes requiring 7 steps or more. Further, while prior art syntheses use toxic or expensive reagents, and most of them require the use of hydrogen gas and heavy metals, it is possible according to the present invention to avoid the use of hydrogen gas, heavy metals and expensive reagents. Such avoidance of using hydrogen gas and/or heavy metals during the whole synthesis of ticagrelor, or in the preparation of precursor compounds disclosed herein, thus constitutes a preferred embodiment of the present invention.

A further significant advantage of the present invention resides in the possibility that several steps can be performed through one-pot conversions, without the need of isolation or separation of intermediate compounds, which one-pot system therefore constitutes a preferred embodiment of the present invention.

Accordingly, the possibility of reducing the number of required reaction steps, of increasing reaction selectivity, and of simplifying reactions respectively strongly contributes to provide an improved industrially applicable and economically beneficial process for obtaining triazolopyrimidine compounds and specifically ticagrelor.

According to a preferred embodiment, the compound of formula II' is prepared by comprising the steps of
(0-1) providing a compound of formula I

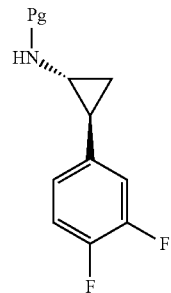

I wherein Pg is an amino protecting group, and
(0-2) reacting the compound of formula I with a compound of the formula

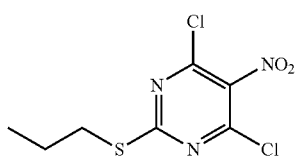

to obtain the compound of formula II'.

It has been found that various amino-protecting groups can be efficiently introduced at this early stage of the synthesis, wherein such amino protecting groups are particularly suited and consistent with the subsequent reaction steps, and allowing to increase reaction selectivity and making reaction simplifications through one-pot conversions possible.

Alternatively, the compound of formula II' can be obtained by first carrying out a substitutional reaction with the pyrimidine ring and subsequently introducing the protecting group, by comprising the steps of:

(0-1') providing a compound of formula Ia

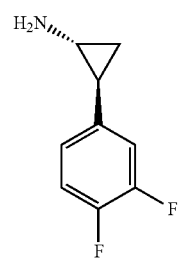

Ia (0-2') reacting the compound of formula Ia with a compound of the formula

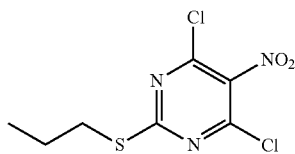

to obtain a compound of formula IIa,

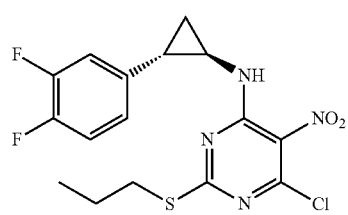

IIa and (0-3') introducing an amino protecting group Pg to obtain the compound of formula II'.

A summary of the afore-mentioned ways to prepare the compound of formula II' is shown in the following scheme 7 below.

Scheme 7 showing process embodiments of the present invention.

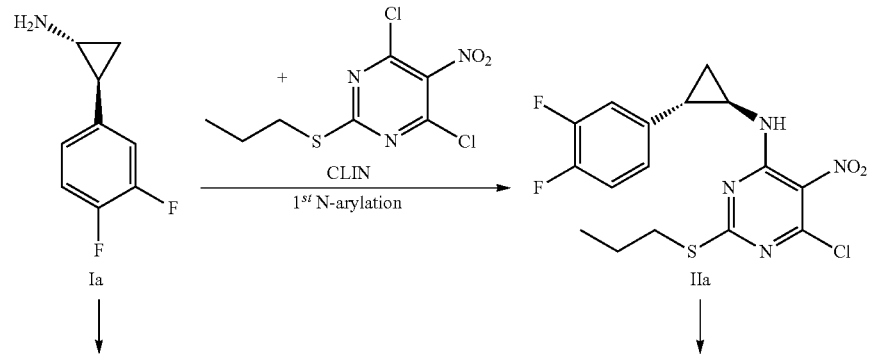

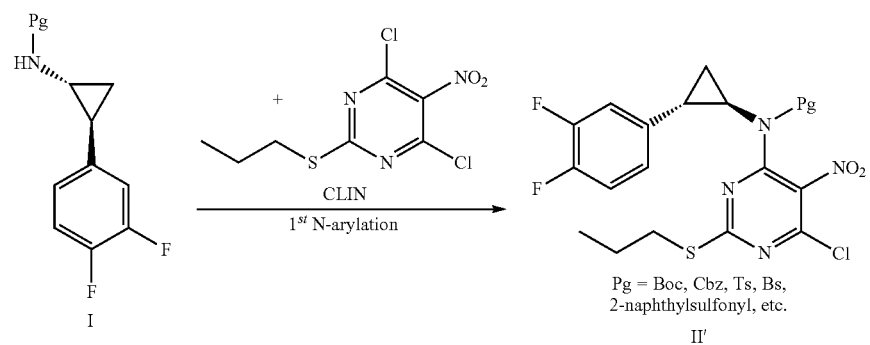

Pg = Boc, Cbz, Ts, Bs, 2-naphthylsulfonyl, etc.

II'

As set forth above, it is possible and corresponds to a particularly preferred embodiment of the present invention, that steps (i) to (iii) specified above, and optionally also the preparation of the compound of formula II', are carried out in one pot. Thus, while of course separation or isolation of any of the intermediate compounds of formulae IIIa', IIIb', IVa', IVb' and optionally of the compound of formula II' can be carried out to obtain such compounds as useful intermediate compounds, this can be beneficially dispensed with if desired. This preferred embodiment is not only economically beneficial by the feature that one-pot synthesis is made possible; it is especially advantageous due to the generally amorphous nature of the intermediate compounds, which would make the purification difficult using non-chromatographic means, while the use of chromatographic means would again render the whole process less economically acceptable. Furthermore, the protecting group "Pg" may be selected in such way that the intermediate of the critical isolable step is solid and recrystallizable, hence no need for using chromatography as a purification method exists anymore.

A further preferred embodiment, which is associated with additional advantages, is based on the beneficial possibility to carry out steps (i) and (ii), optionally also steps (0-1) to (0-2) or (0-1') to (0-3') generally under basic conditions in the presence of bases, which renders the synthetic steps consistent and further facilitates one-pot methodologies. More specifically, all chemical steps from the start shown above up to the compound of formula IVa are most efficient in the presence of bases of various strengths, more preferably in subsequent steps consistent with, or allowing, decreasing basicity. For example, a proper base, which can be used for the deprotonation of the compound of formula Ia is sodium hydride, while a suitable base which can be used as a hydrogen chloride scavenger in reaction step (i) (i.e. during the N-arylation of the compound of formula VI) can be selected from tertiary amines, alkali carbonates, or alkali phosphates, or from other poorly nucleophilic bases. Subsequently, mildly basic conditions, preferably using alkali carbonates, are well suited also for the nitro group reduction in step (ii), using for example sulphur-based reducing agents such as sodium dithionite or formamidine sulfinic acid (thiourea dioxide). Subsequently, and again consistent with a preferred one-pot methodology, the nitrosation step (iii) can be performed by shifting to mildly acidic conditions, suitably achieved for example by the addition of acetic acid, using appropriate nitrosating agents such as sodium nitrite, or it can be carried out as an alternative step by heating the solution of the crude product of the compound of formula IVa in the presence of an alkyl nitrite such as the readily available reagent isopentyl nitrite.

Further advantageous embodiments of the process according to the present invention are based on the synthetic possibility that useful synthetic options are allowed, depending on which cyclopentane substituent "Z" is used, and depending on what substituent "Z" is used at which stage of the synthesis. The possible synthetic options become more apparent by the illustrations of possible synthetic embodiments shown in the following scheme 8:

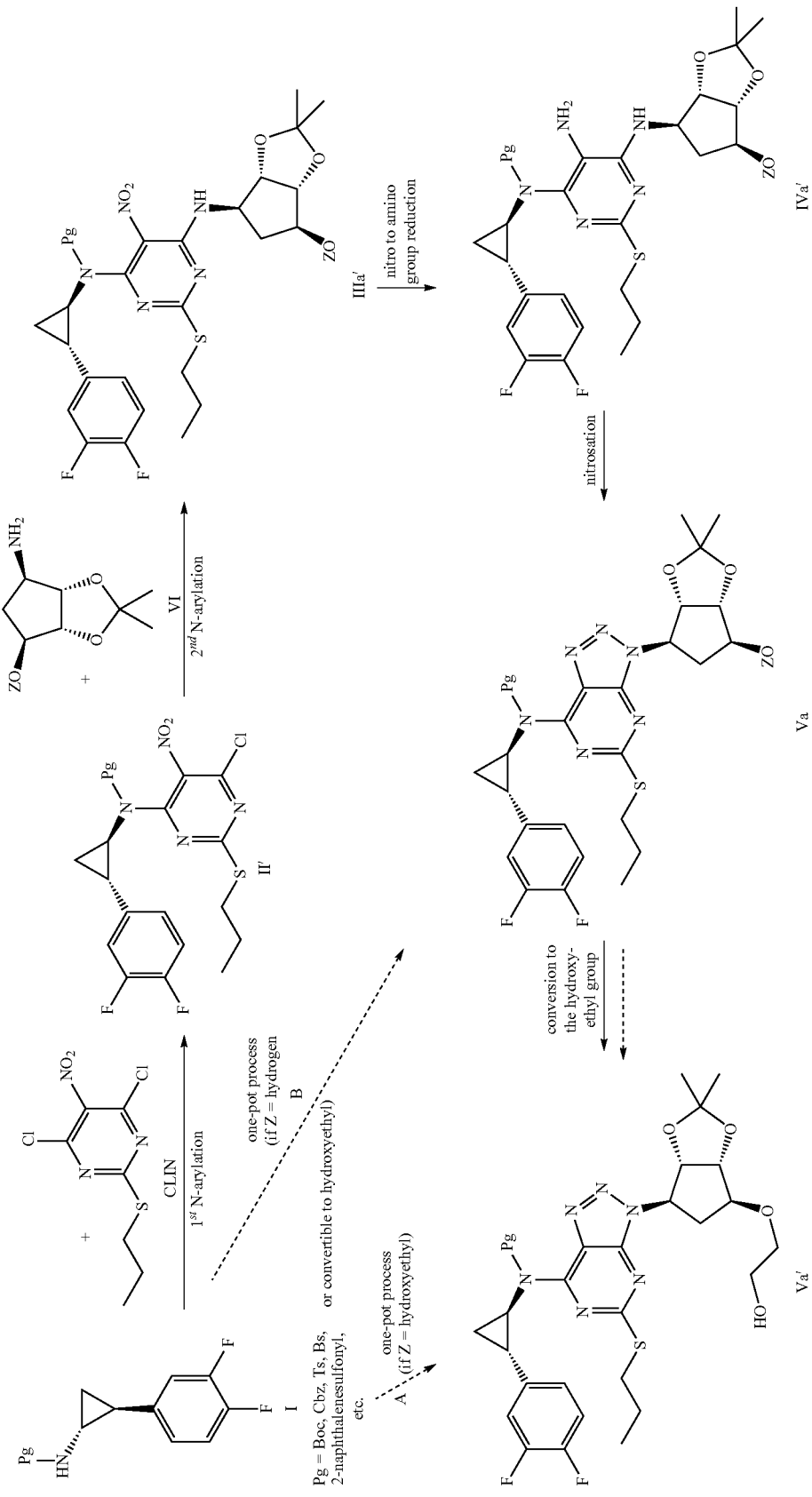

More specifically, if the compound of formula VI, that is used in the reaction step (i) to be reacted with the compound of formula II', already has a hydroxyethyl or a group convertible to hydroxyethyl as the group "Z", a one-pot process made feasible according to a preferred embodiment of the present invention already yields a desirable precursor compound of ticagrelor (see dashed arrow line A shown in reaction scheme 8), which precursor compound then only needs to be subjected to deprotection reactions for removing Pg and the vicinal hydroxyl protecting group at the cyclopentane ring, respectively. If, alternatively, "Z" in the compound of formula VI is hydrogen, then the molecular assembly sequence allows for a facilitated introduction of the hydroxyethyl group when it is done at a later stage of the synthesis, which is made possible because the described advantageous and preferred synthetic embodiments are still consistent with a one-pot process (see dashed arrow line B, and the subsequent conversion of the Z group in the compound of formula Va to the hydroxyethyl group as shown in scheme 8). Therefore, in the afore-mentioned alternative and economical routes to precursors of ticagrelor or ticagrelor itself, such preferred embodiments of the present invention constitute particularly suitable solutions for the synthetic challenge arising when the hydroxyethyl side chain is introduced at an early or at a later stage of the synthetic route.

Therefore, the advantageous possibility to join numerous steps into one-pot synthetic schemes is a surprising and unexpected effect of the present invention that results just from introducing the protective group to the amine moiety bound to the cyclopropane ring (denoted by the "Pg" protecting groups in the synthetic schemes), which protecting group "Pg" is present throughout the relevant intermediate compounds of formulae Ia-Va' (or as later shown in formulae I-V).

According to another embodiment, alternatively, a compound of formula VII can be added to the compound of formula II' to yield a compound of formula IIIb' (Scheme 9). VII already has a hydroxyethyl group, while the hydroxyl groups at the cyclopentane ring are not protected. From a compound of formula IIIb', a compound of formula IVb' can be obtained by reduction of the nitro group. As the hydroxyl groups at the cyclopentane ring are not protected, the nitrosation of IVb' yields directly a compound of formula Vb.

A compound of formula VII, another embodiment of the present invention, can be prepared for example by acid hydrolysis from AMALA (Scheme 9), which can be prepared as described in WO 01/92263.

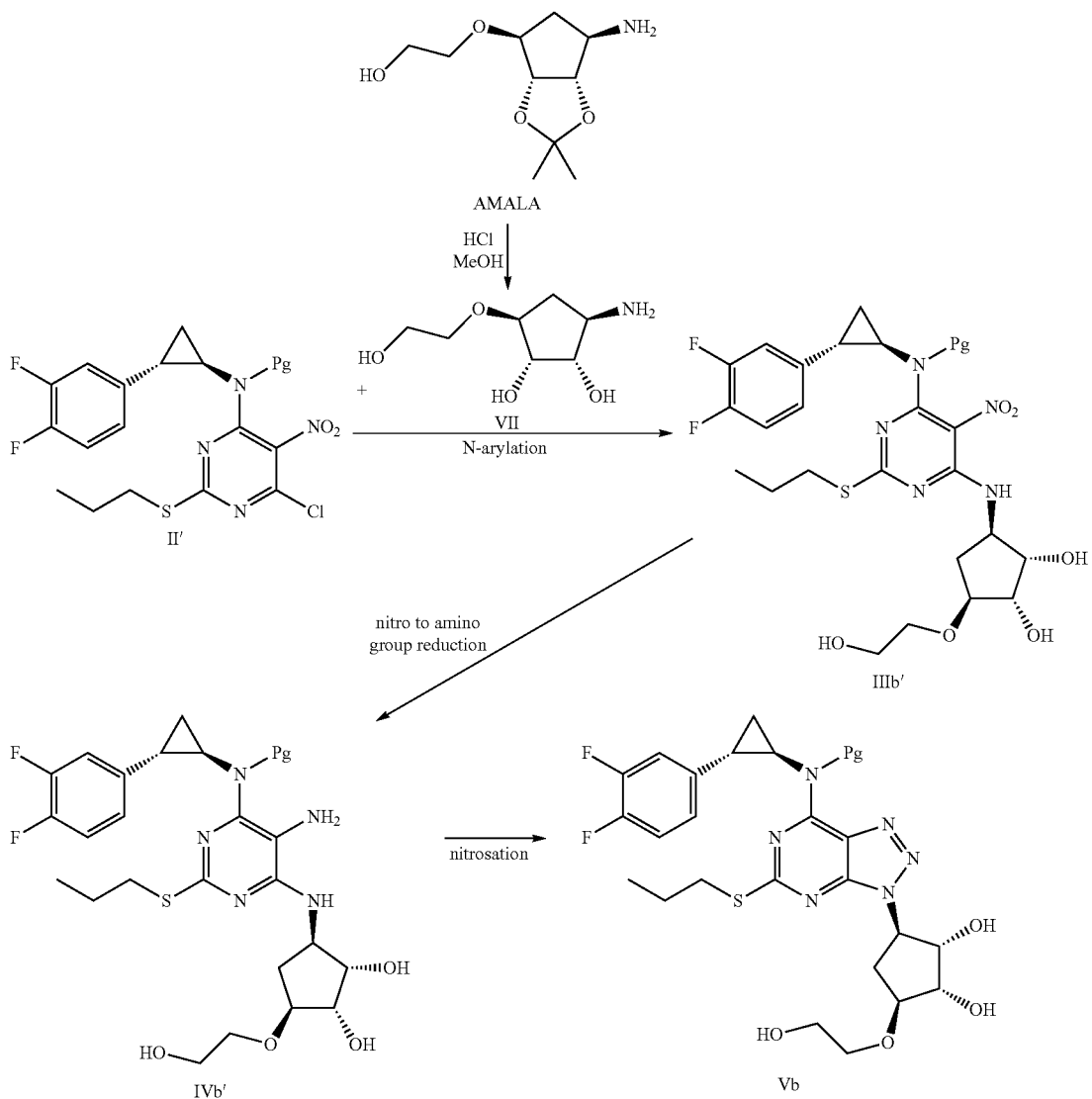

Scheme 9 showing a specific embodiment of the present invention.

Alternatively, a compound of formula VII'

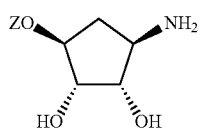

wherein Z is a group convertible to the hydroxyethyl group can be used instead of VII in a sequence of reactions presented in scheme 9. In the final step the group Z is converted to hydroxyethyl group by using methods known to the person skilled in the art as mentioned below.

According to the present invention, the group "Pg" can be selected from the group consisting of oxycarbonyl-type amino protecting groups and sulfonyl-type amino protecting groups, without being limited thereto. The group "Pg" as used in the present invention does not merely serve the purpose of protecting the amino group. It additionally provides for enhanced selectivity of the reactions into which the compounds of formula II enter. It was found that the selectivity for monosubstitution of the compound of formula

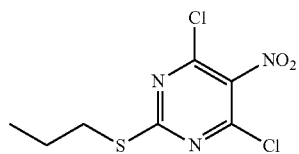

is greatly enhanced by the reaction with the resulting carbamates or sulfamides when compared to the direct reaction between the compound of formula Ia (unprotected cyclopropane analogue) with CLIN. Yields are also improved. Moreover, the oxycarbonyl or sulfonyl N-substituents also allow for the regioselective triazole ring formation during the nitrosation step, and regioselective alkylation during the hydroxyethyl group introducing steps. According to preferred embodiments, Pg can be selected from the group consisting of tert-butyloxycarbonyl (Boc), carbobenzyloxy (Cbz), methanesulfonyl (Ms), benzenesulfonyl (Bs), p-toluenesulfonyl (Ts), and 2-naphthalenesulfonyl.

The group convertible to hydroxyethyl ("Z") according to the invention can be selected from the group consisting of: —$CH_2COOR_1$, wherein $R_1$ is selected from linear or branched $C_1$-$C_6$-alkyl or benzyl; cyanomethyl; —$CH_2CH(E_1R_2)(E_2R_3)$, wherein $E_1$ and $E_2$ are independently selected from a chalcogen element, preferably O or S, and $R_2$ and $R_3$ are the same or different, selected from $C_1$-$C_4$-alkyl, or together form $C_2$-$C_4$-alkylene or o-phenylene connection; or —$CH_2CH_2$—$OR_4$ wherein $R_4$ is a hydroxy protecting group, selected from tertiary alkyl group, preferably tert-butyl or trityl, arylmethyl group, preferably benzyl or para substituted benzyl, methoxy substituted $C_1$-$C_2$-alkyl group, preferably methoxymethyl (MOM), trisubstituted silyl group, preferably trimetylsilyl, tert-butyldimethylsilyl (TBDMS) or tert-butyldiphenylsilyl, acyl, preferably acetyl or benzoyl.

The group "Z" can be converted to the hydroxyethyl group by using methods known to the person skilled in the art, for instance —$CH_2COOR_1$ by reduction, cyanomethyl and —$CH_2CH(OR_2)(OR_3)$ by acid hydrolysis and reduction, silyloxyethyl groups by fluoride cleavage, tert-alkoxyethyl by acid cleavage, benzyloxyethyl by hydrogenation. In view of telescoping intermediates to the next step without isolation as described in route B in Scheme 8 it is preferable that the group is stable in all reactions of the one-step sequence, such as being stable in basic conditions. Most preferable groups are selected from —$CH_2COOMe$, —$CH_2COOEt$, tert-butoxyethyl, trityloxyethyl, and benzyloxyethyl. Preferably, the groups Pg, $R_4$ and the glycol protection group are removed in one reaction step by acid cleavage. In this view tert-butoxyethyl group and trityloxyethyl group are the most preferable.

For preparing a ticagrelor (TCG) with the formula VIII shown below, the compound of formula Va or Vb as described above is subjected to the deprotection reaction(s) in order to remove Pg and in case of Va also the vicinal hydroxyl protecting group at the cyclopentane ring, respectively. The deprotection reaction(s) can proceed at the same time, to concurrently remove both "Pg" and the vicinal hydroxyl protecting group at the cyclopentane ring, for example using acids such as HCl or phosphoric acid in a suitable organic solvent, for example alcohols such as methanol or ethanol. If desired, a salt, a cocrystal or a complex of the compound of formula VIII (ticagrelor, TCG) can be optionally formed.

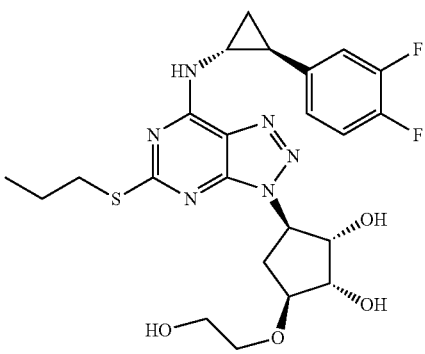

The ticagrelor compound prepared according to the invention may be used or administered on its own, preferably it is administered as a pharmaceutical composition comprising ticagrelor and a pharmaceutically acceptable excipient and/or carrier. Further, the ticagrelor compound prepared according to the invention may be combined with other drugs, especially drugs having activity against platelet aggregation or thrombolytic events.

In a further aspect of the present invention, a pharmaceutical composition comprising the compound of formula VIII (ticagrelor, TCG) or a salt thereof is prepared by comprising the steps of preparing the compound of formula VIII or a salt thereof as described above, and mixing the compound of formula VIII or a salt thereof with a pharmaceutically acceptable carrier and/or excipient. The administration form can be suitably chosen, e.g. a form suitable for oral, parenteral, rectal administration and/or administration by inhalation, and the dosage form may be solid, liquid, or powdery. Therefore, the pharmaceutical composition comprising ticagrelor compound prepared according to the invention may suitably be in the form of tablets, pills, capsules, syrups, powders or granules for oral administration; or as sterile parenteral or subcutaneous solutions, suspensions for parenteral administration; or as suppositories for rectal administration.

Suitable excipients and/or carriers include, without being limited to, diluents, binders, disintegrants, lubricants, etc. For example, the compound or a finely divided form thereof, or particles comprising the compound, are mixed with a carrier or binder substance, e.g. a mono-, di- or polysaccharide such as sugars and starch, a sugar alcohol or another polyol. For example, lactose, saccharose, sorbitol, mannitol, starch, cellulose derivatives, a binder such as polyvinylpyrrolidone, and a lubricant such as magnesium stearate, calcium stearate, polyethylene glycol, waxes, paraffin, and the like are mixed, and then compressed into tablets. The compound or a finely divided form thereof or particles containing the same may be coated by another substance. The powder mixture or particles containing the compound may also be dispensed into capsules.

The pharmaceutical composition comprising ticagrelor prepared according to the invention in a desired dose is generally suitable to treat a disease or condition of a patient in need thereof, specifically to display a desired activity against platelet aggregation, or in the treatment or prophylaxis of thrombolytic events.

Further aspects of the present invention reside in the provision of valuable intermediate compounds useful in the synthesis of a compound of formula VIII (ticagrelor, TCG), which intermediate compounds respectively have in common the amino group protecting group Pg:

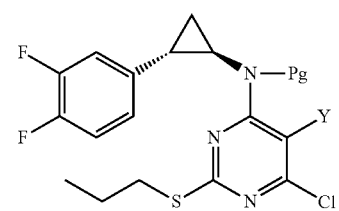

II (Pg is an amino protecting group, and Y is $NO_2$ or $NH_2$)

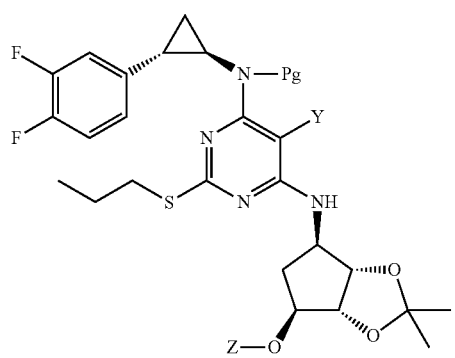

IVa

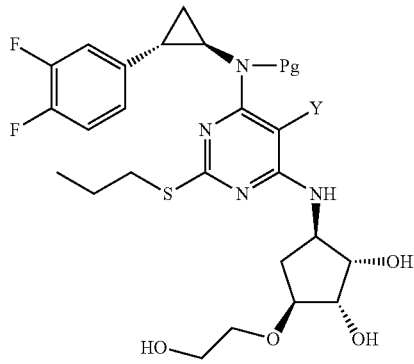

IVb (Pg is an amino protecting group, Y is $NO_2$ or $NH_2$, and Z is hydrogen, hydroxyethyl or a group convertible to hydroxyethyl)

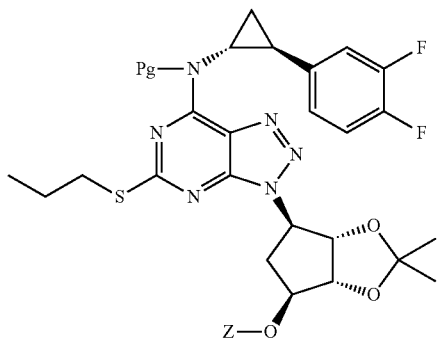

Va (Pg is an amino protecting group, and Z is hydrogen, hydroxyethyl or a group convertible to hydroxyethyl)

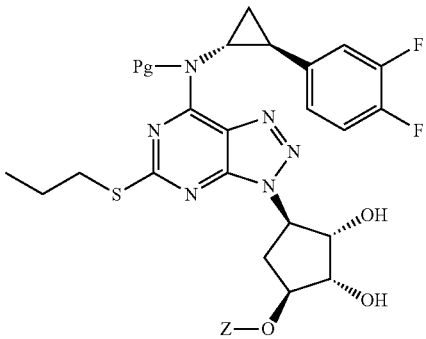

Vb (Pg is an amino protecting group, and Z is hydrogen, hydroxyethyl or a group convertible to hydroxyethyl)

As to the definition of "Pg" and "Z", reference is made to the descriptions elsewhere in the present specification.

Particular examples of such useful intermediate compounds are listed by their respective formulas below (in these formulas, "Pr" denotes "propyl"):

| Formula | Chemical name |
|---|---|
| | tert-butyl(6-chloro-5-nitro-2-(propylthio)pyrimidin-4-yl)((1R,2S)-2-(3,4-difluorophenyl)cyclopropyl)carbamate |
| | tert-butyl((1R,2S)-2-(3,4-difluorophenyl)cyclopropyl)(6-(((3aS,4R,6S,6aR)-6-hydroxy-2,2-dimethyltetrahydro-3aH-cyclopenta[d][1,3]dioxol-4-yl)amino)-5-nitro-2-(propylthio)pyrimidin-4-yl)carbamate |
| | tert-butyl((1R,2S)-2-(3,4-difluorophenyl)cyclopropyl)(6-(((1R,2S,3S,4S)-2,3-dihydroxy-4-(2-hydroxyethoxy)cyclopentyl)amino)-5-nitro-2-(propylthio)pyrimidin-4-yl)carbamate |
| | tert-butyl(5-amino-6-(((3aS,4R,6S,6aR)-6-hydroxy-2,2-dimethyltetrahydro-3aH-cyclopenta[d][1,3]dioxol-4-yl)amino)-2-(propylthio)pyrimidin-4-yl)((1R,2S)-2-(3,4-difluorophenyl)cyclopropyl)carbamate |

| Formula | Chemical name |
|---|---|
| | tert-butyl(5-amino-6-(((1R,2S,3S,4S)-2,3-dihydroxy-4-(2-hydroxyethoxy)cyclopentyl)amino)-2-(propylthio)pyrimidin-4-yl)((1R,2S)-2-(3,4-difluorophenyl)cyclopropyl)carbamate |
| | tert-butyl((1R,2S)-2-(3,4-difluorophenyl)cyclopropyl)(3-((3aS,4R,6S,6aR)-6-hydroxy-2,2-dimethyltetrahydro-3aH-cyclopenta[d][1,3]dioxol-4-yl)-5-(propylthio)-3H-[1,2,3]triazolo[4,5-d]pyrimidin-7-yl)carbamate |
| | tert-butyl((1R,2S)-2-(3,4-difluorophenyl)cyclopropyl)(3-((1R,2S,3S,4S)-2,3-dihydroxy-4-(2-hydroxyethoxy)cyclopentyl)-5-(propylthio)-3H-[1,2,3]triazolo[4,5-d]pyrimidin-7-yl)carbamate |
| | methyl 2-(((3aR,4S,6R,6aS)-6-(7-((tert-butoxycarbonyl)((1R,2S)-2-(3,4-difluorophenyl)cyclopropyl)amino)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)acetate |

| Formula | Chemical name |
|---|---|
| | tert-butyl((1R,2S)-2-(3,4-difluorophenyl)cyclopropyl)(3-(((3aS,4R,6S,6aR)-6-(2-hydroxyethoxy)-2,2-dimethyltetrahydro-3aH-cyclopenta[d][1,3]dioxol-4-yl)-5-(propylthio)-3H-[1,2,3]triazolo[4,5-d]pyrimidin-7-yl)carbamate |
| | tert-butyl(3-(((3aS,4R,6S,6aR)-6-(2-(tert-butoxy)ethoxy)-2,2-dimethyltetrahydro-3aH-cyclopenta[d][1,3]dioxol-4-yl)-5-(propylthio)-3H-[1,2,3]triazolo[4,5-d]pyrimidin-7-yl)((1R,2S)-2-(3,4-difluorophenyl)cyclopropyl)carbamate |
| | N-((1R,2S)-2-(3,4-difluorophenyl)cyclopropyl)-N-(6-(((3aS,4R,6S,6aR)-6-hydroxy-2,2-dimethyltetrahydro-3aH-cyclopenta[d][1,3]dioxol-4-yl)amino)-5-nitro-2-(propylthio)pyrimidin-4-yl)-4-methylbenzenesulfonamide |

-continued

| Formula | Chemical name |
|---|---|
| 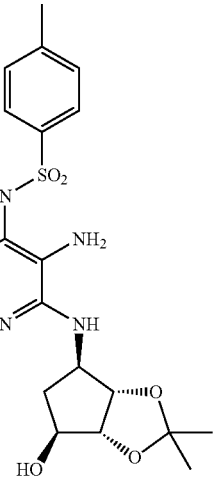 | N-(5-amino-(1R,2S)-2-(3,4-difluorophenyl)cyclopropyl)-N-(6-(((3aS,4R,6S,6aR)-6-hydroxy-2,2-dimethyltetrahydro-3aH-cyclopenta[d][1,3]dioxol-4-yl)amino)-2-(propylthio)pyrimidin-4-yl)-4-methylbenzenesulfonamide |
| 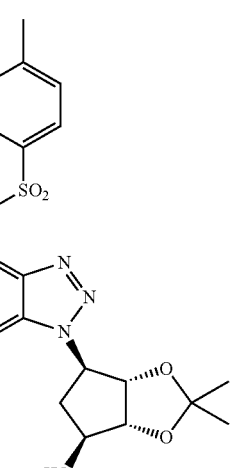 | N-((1R,2S)-2-(3,4-difluorophenyl)cyclopropyl)-N-(3-((3aS,4R,6S,6aR)-6-hydroxy-2,2-dimethyltetrahydro-3aH-cyclopenta[d][1,3]dioxol-4-yl)-5-(propylthio)-3H-[1,2,3]triazolo[4,5-d]pyrimidin-7-yl)-4-methylbenzenesulfonamide |
| 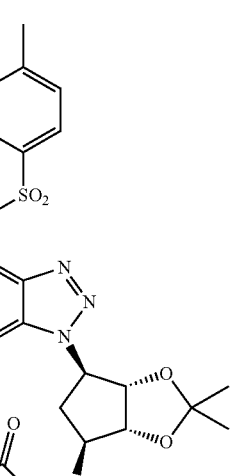 | methyl 2-(((3aR,4S,6R,6aS)-6-(7-(N-((1R,2S)-2-(3,4-difluorophenyl)cyclopropyl)-4-methylphenylsulfonamido)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)acetate |
| 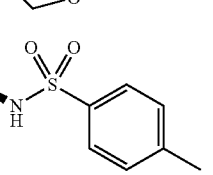 | N-((1R,2S)-2-(3,4-difluorophenyl)cyclopropy)-4-methylbenzenesulfonamide |

In the above particularly exemplified compounds, "Pg" is represented by tert-butyloxycarbonyl (Boc)-group and p-toluenesulfonyl (Ts) group, but it should be apparent that analogous useful and further specifically exemplified intermediate compounds correspond to those listed above, wherein the specific protecting group, Boc or Ts, is replaced by other amino group protecting groups, e.g. carbobenzyloxy (Cbz), p-toluenesulfonyl (Ts) group, benzenesulfonyl (Bs), methanesulfonyl (Ms), or 2-naphthalenesulfonyl.

Specific embodiments representing the basic synthetic concept of the present invention are further described below. More specifically, in an illustrative but non-limiting example, scheme 10 below illustrates a concept of the molecular assembly of ticagrelor (TCG), while noting that this scheme is by no means limiting with respect to the specific nature of transformation, reactions, conditions protecting groups, methods and reagents, which can be used.

This illustration of the general synthetic route first includes a substitution of the amino group of the CPA with an electron withdrawing group, for example of the oxycarbonyl or sulfonyl type, in order to increase the acidity of the N—H bond. It was found that the selectivity for monosubstitution at CLIN is greatly enhanced if in the reaction of N-arylation a carbamate, sulfonamide or other amide derivative of CPA is reacted with CLIN, compared to direct reaction between CPA and CLIN. The obtained N-protected intermediates of the structural type II are then used to arylate AMAL to give intermediates IIIa. The nitro group is then reduced to give the diamines IVa which can be nitrosated to affect the formation of the triazole ring of intermediates Va. The protecting group introduced in the first step allows for the regioselective triazole ring formation during the nitrosation step. Compound Va is already suitably protected for the selective introduction of the hydroxyethyl group on the secondary alcohol group. The hydroxyethylation process and the later deprotection steps to give ticagrelor (TCG) can be performed by various methodologies known to those skilled in the art, such as an O-alkylation with an alkyl haloacetate, ester group reduction and deprotection under acidic conditions.

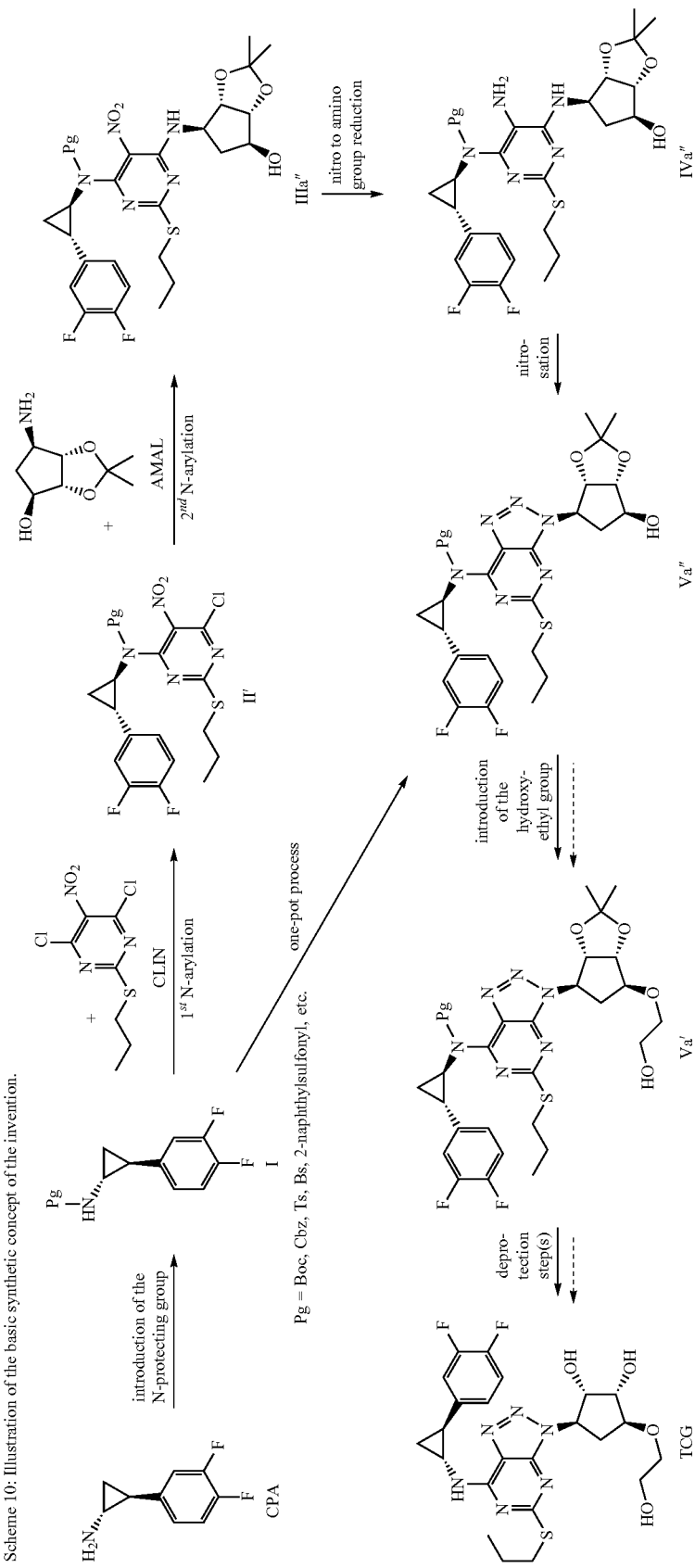
Scheme 10: Illustration of the basic synthetic concept of the invention.
Pg = Boc, Cbz, Ts, Bs, 2-naphthylsulfonyl, etc.

In a more specific example of ticagrelor synthesis, the embodiment of the invention is represented by the use of the tert-butoxycarbonyl (Boc) protected CPA derivative CPABOC (Scheme 11). This is deprotonated with sodium hydride in order to be N-arylated with CLIN. This gives CPABOCCIN with good selectivity and yields. This product is then used for the N-arylation of AMAL, preferably in the presence of a base such as triethylamine or alkali carbonates, to give BAAL. The next reaction steps include the reduction of the nitro group to give BAALA and its nitrosation to give BATAM. This is a key intermediate for use in the subsequent hydroxyethylation and deprotection steps which can be implemented using numerous synthetic approaches. Specifically, this can be achieved by alkylation with methyl bromoacetate to give BATAME, its reduction with lithium borohydride to give BATAMA, and finally the one step deprotection of the acetonide and Boc protecting groups under acidic conditions to give ticagrelor (TCG).

This synthetic route was found particularly advantageous for the application of one-pot methodologies. Specifically, the synthesis can be efficiently carried from CPABOC to BATAM in a one-pot procedure comprised of four chemical steps (Scheme 11).

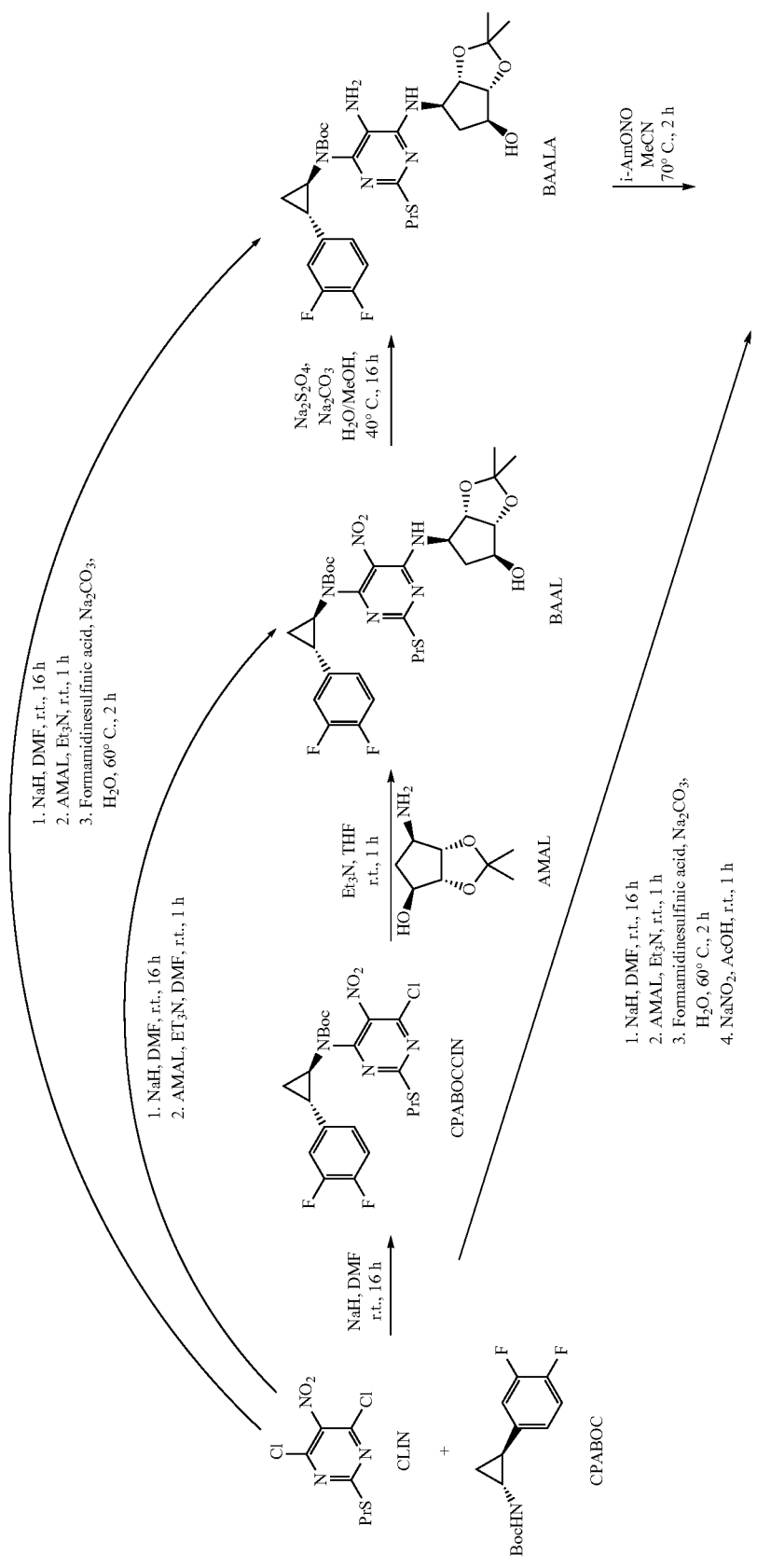

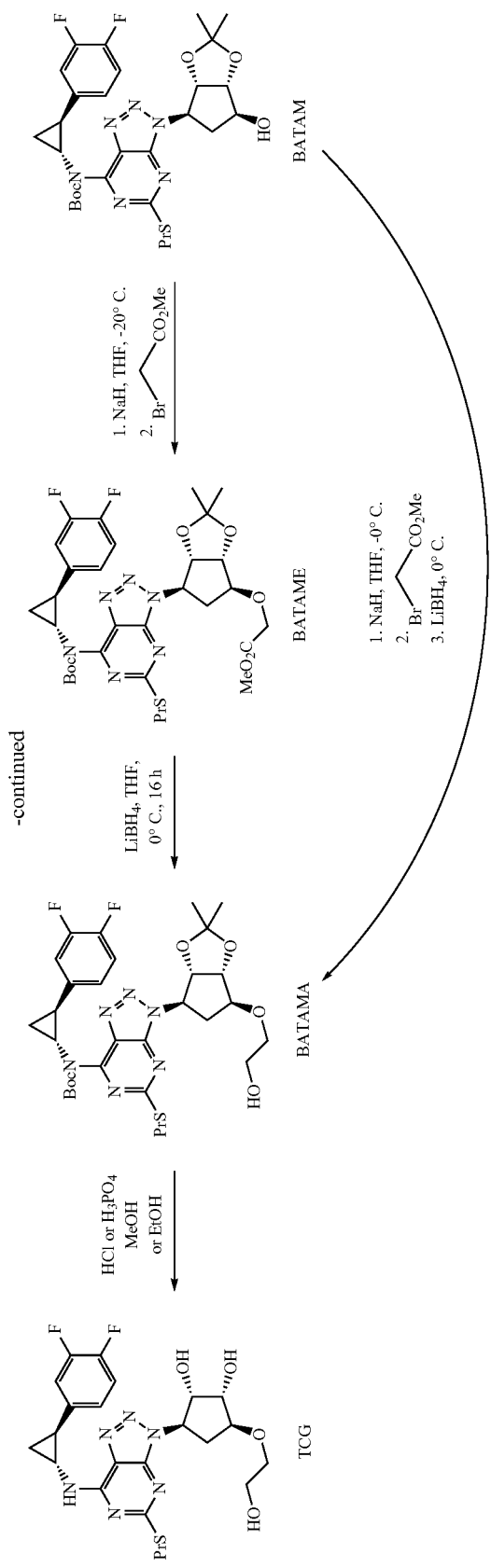

Protecting groups other than Boc may also be suitable. For example, the sulfonyl protecting groups, such as the p-toluenesulfonyl (Ts), benzenesulfonyl (Bs) or the 2-naphthalenesulfonyl group, were found to be suitable for the one pot synthesis of intermediates of type V directly from CPA derived sulfonamides CPATs, CPAS or CPAN correspondingly (Scheme 12). The increased acidity of these sulfonamides in comparison to the less acidic carbamate CPABOC allows for the use of more practical bases than sodium hydride. Tripotassium phosphate in acetonitrile was found particularly suitable for this first chemical step, as well as for the subsequent two chemical steps comprising the one-pot process toward TAALA, SAALA or NAALA. The triazole ring formation is suitably carried out by extracting the water diluted reaction mixture with ethyl acetate, phase separation, addition of isopentyl nitrite to the organic phase and mild heating. The intermediates TAALA, SAALA and NAALA thus need not be isolated in this process.

Scheme 12: One-pot synthesis of sulfonyl protected triazoles without the isolation of intermediates and further transformation to CPATAMA.

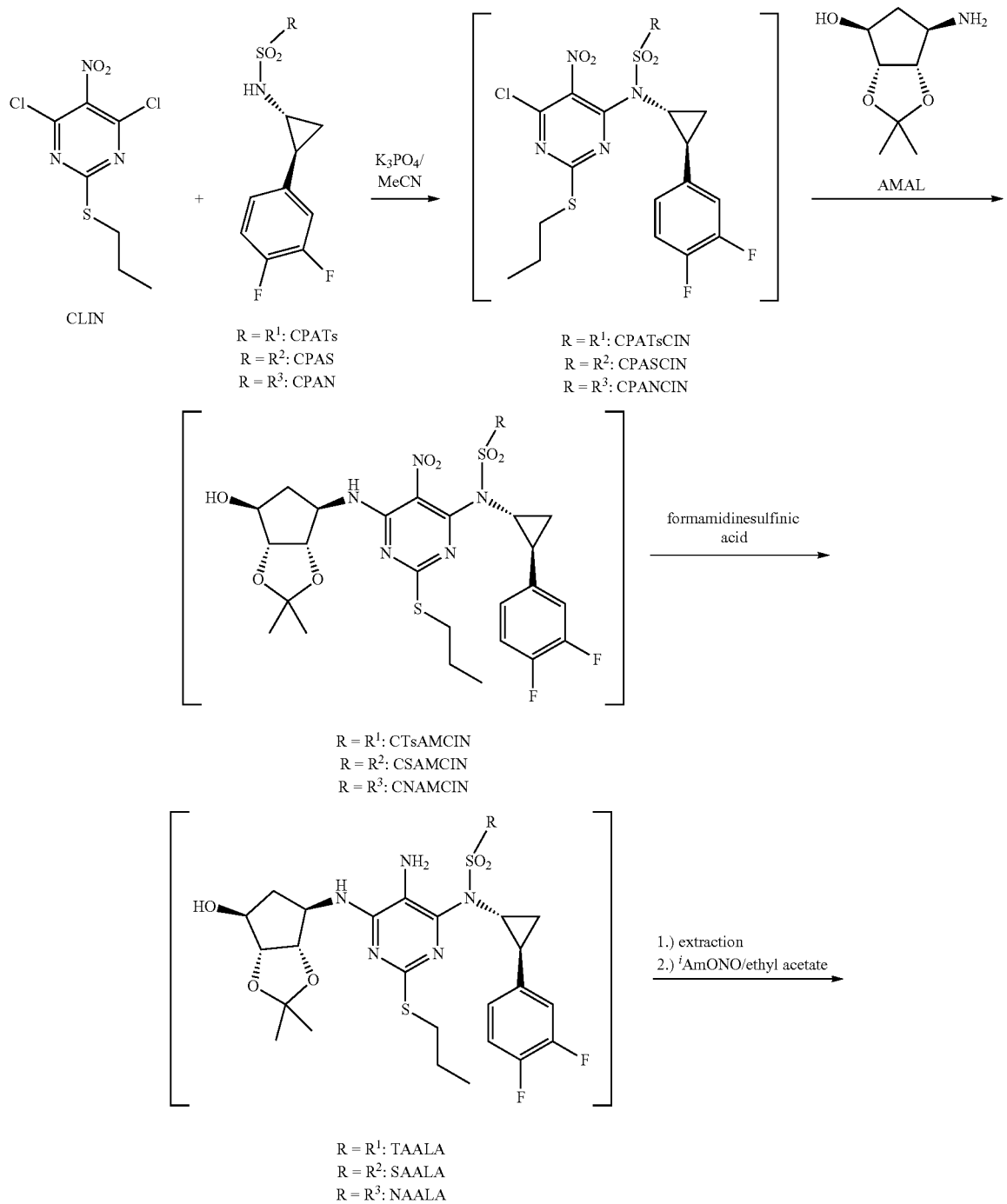

-continued

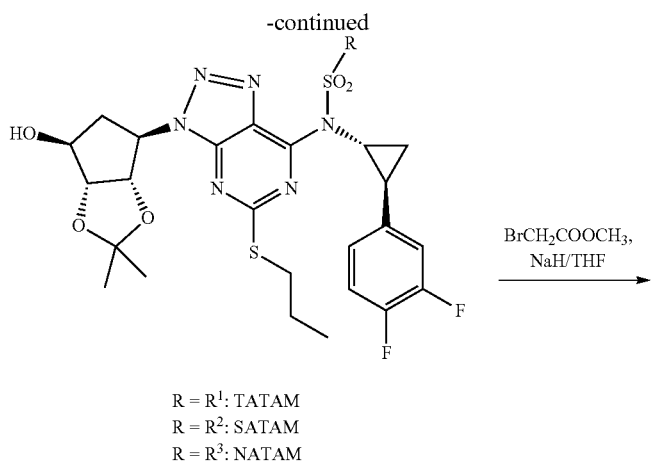

R = R¹: TATAM
R = R²: SATAM
R = R³: NATAM

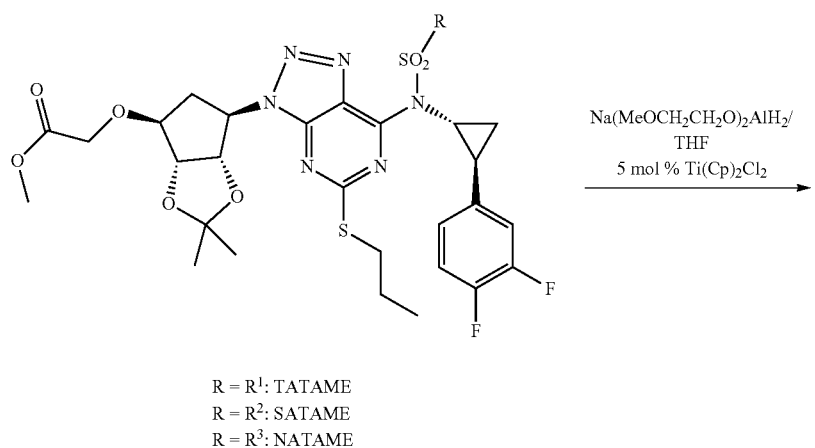

R = R¹: TATAME
R = R²: SATAME
R = R³: NATAME

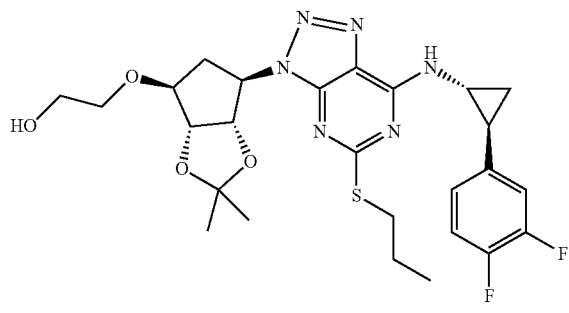

CPATAMA

R = p-tolyl (R¹), benzenesulfonyl (R²), or 2-naphthyl (R³)

The compounds TATAM, SATAM, NATAM, or related sulfonamides, corresponding to intermediates of type Va, can then be used for the introduction of the hydroxyethyl ether side chain on their hydroxy group and further transformations toward ticagrelor. In particular, the hydroxyethyl group introduction can be performed by alkylation with methyl bromoacetate to give the ester intermediate which can then be reduced to the alcohol using the sodium bis(2-methoxyethoxy)aluminumhydride while at the same time catalytic amounts of titanocene dichloride promote the reductive cleavage of the sulfonyl protecting groups. Thus, the final intermediate CPATAMA can be obtained in two reaction steps from TATAM or other such sulfonamides. This new method for sulfonyl group deprotection employing the titanocene catalysis was developed specifically for the purpose of being applicable during the ester group reduction in order to perform both functional group transformations concurrently. CPATAMA is then hydrolysed to ticagrelor in acidic media according to prior art.

In another embodiment the key intermediate BATAM can be prepared from CPATAM, which can be derived from CLTAM as shown in scheme 13. The analogous sulfonyl protected intermediate TATAM can be prepared by the N-arylation of CLTAM with CPATs in acetonitrile and $K_3PO_4$ as a base. CLTAM can be prepared as described in WO 00/34283 (Scheme 1).

Scheme 13: Synthesis of BATAM from CLTAM via CPATAM.

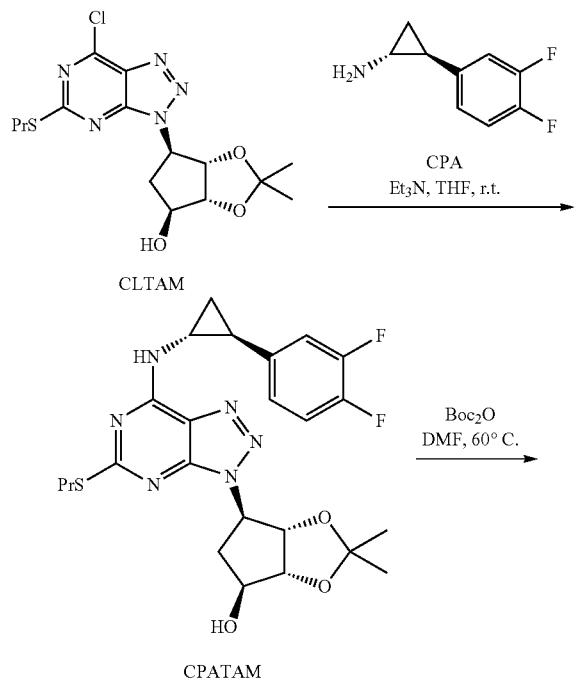

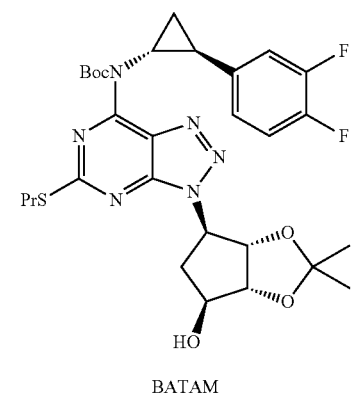

BATAM

In another special embodiment ticagrelor is prepared from the protected cyclopropylamine derivative CPABOC. First step of the synthesis is a one-pot reaction of heteroarylation in basic conditions and condensation with the unprotected cyclopentane derivative OLA (VII), followed by reduction of nitro group to amino group yielding the intermediate BAALOAA, which is further converted to benzotriazole BATOMA. Deprotecting of BATOMA gives ticagrelor in high yield. Again the conversion of a simple starting compound such as CLIN to ticagrelor needs only four technological steps, even with no need for additional protection of cyclopentane hydroxy groups (Scheme 14).

In a further special embodiment presented in Scheme 15 ticagrelor is prepared from the protected cyclopropylamine derivative CPABOC using intermediates with a group convertible to the hydroxyethyl group (TBUAM (VI')). In the first step the molecule BAALAT is constructed of three constituted parts CPABOC, TBUAM and CLIN in one step. The intermediate is further transformed by reduction of nitro group and diazotisation to the triazolo derivative BATAMAT, which is finally deprotected by simultaneous cleavage of Boc, tert-butoxy and isopropylidene groups in acidic methanol solution to give ticagrelor. In spite of the additional conversion to the hydroxy group the process keeps a reduced number of steps by triple deprotection in one step.

Scheme 14: Synthesis of ticagrelor using unprotected cyclopentane derivative.

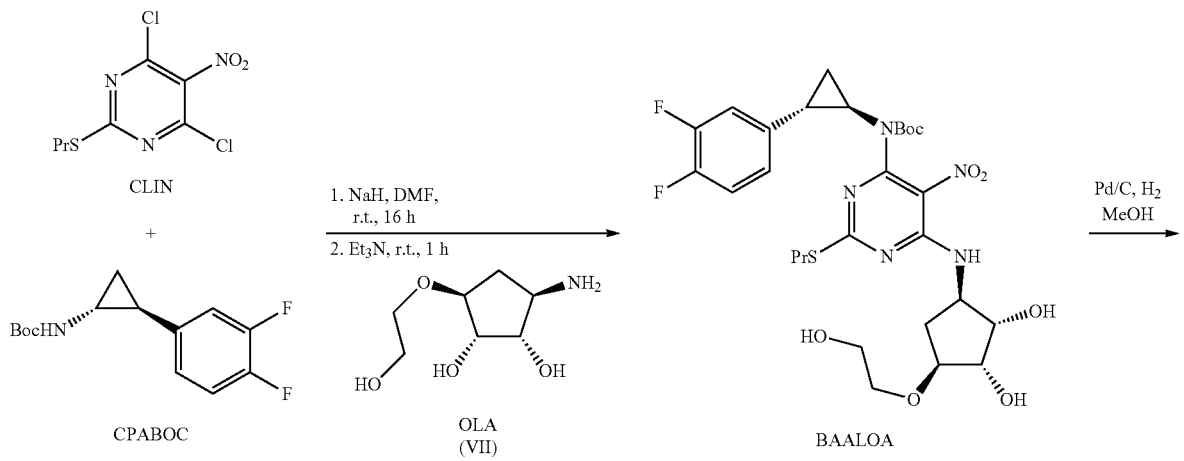

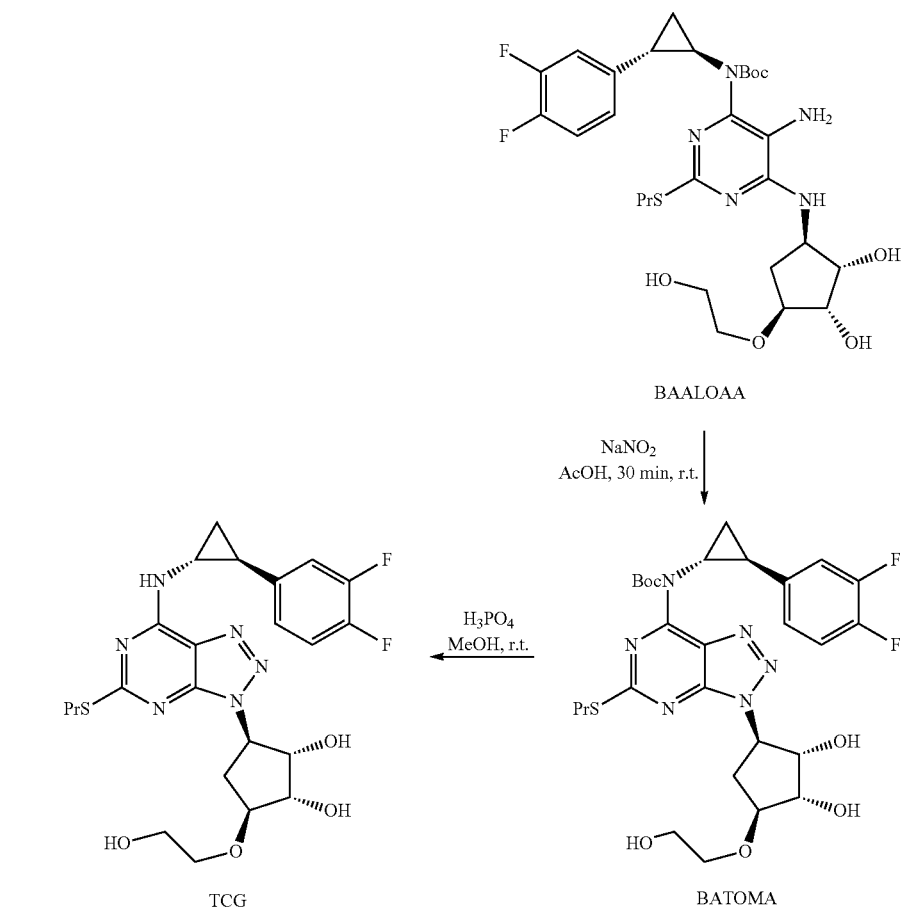
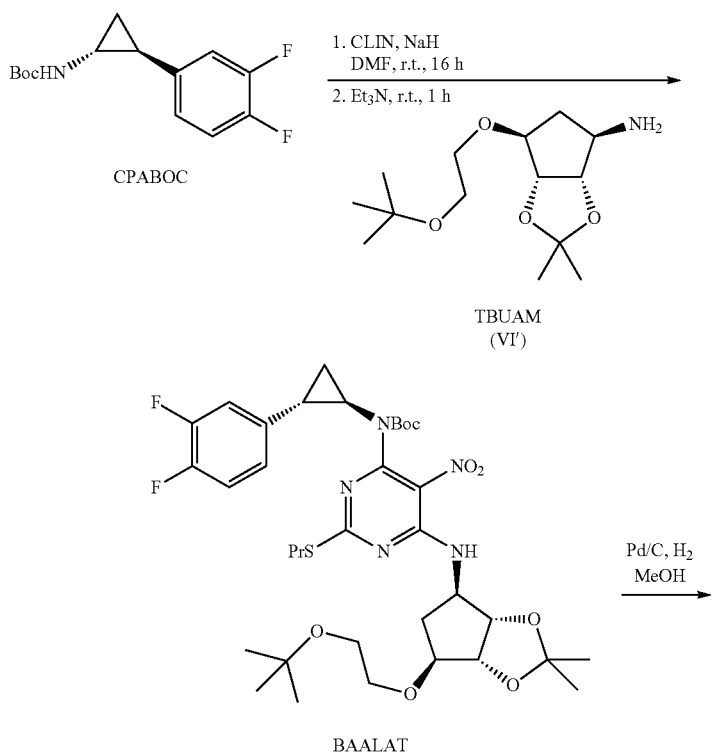
Scheme 15: Synthesis of ticagrelor using triple cleavage of protecting group in one step.

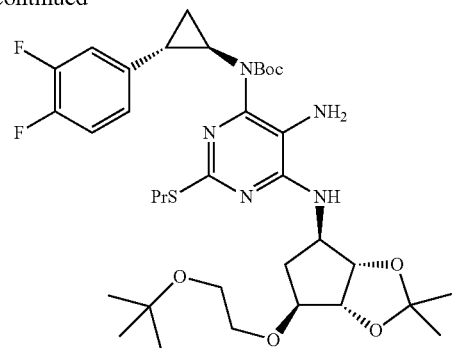

BAALATA

↓ NaNO₂
AcOH, r.t.

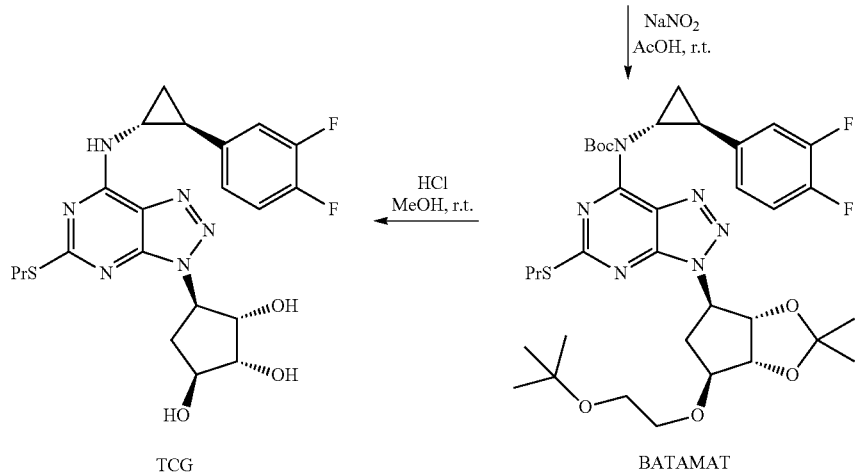

TCG          BATAMAT

In the following the present invention will be described in further detail by illustrative, non-limiting examples.

EXAMPLES

Example 1

Preparation of tert-butyl ((1R,2S)-2-(3,4-difluorophenyl)cyclopropyl)carbamate (CPABOC)

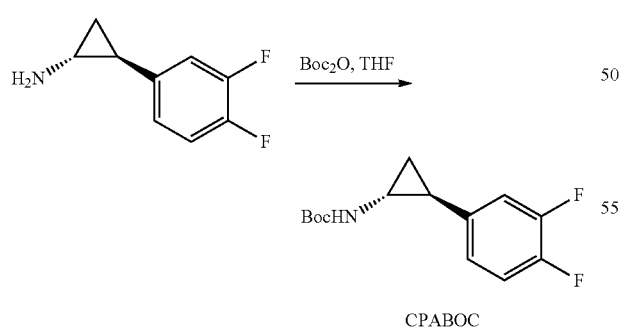

CPABOC

To a solution of trans-(1R,2S)-2-(2,3-difluorophenyl)cyclopropylamine (26.4 g, 156 mmol) (24 mL, 172 mmol) in THF (100 mL) was slowly added a solution of Boc₂O in THF (100 mL). The resulting reaction mixture was stirred at room temperature for 1 h, then concentrated. After addition of water (200 mL), the white precipitate was filtered off, washed with water (3×100 mL), and dried to afford 42.0 g (99% yield) of title compound as white powder. $^1$H NMR (CDCl$_3$, 500 MHz) δ 1.07-1.16 (m, 2H), 1.45 (s, 9H), 2.01 (m, 1H), 2.31 (m, 1H), 2.64 (m, 1H), 4.91 (br s, 1H), 6.88 (m, 1H), 6.95 (m, 1H), 7.03 (m, 1H); $^{19}$F NMR (CDCl$_3$, 470.5 MHz) δ −139.3 (m, 1F), −142.8 (m, 1F); MS (ESI) m/z: 270 [MH]$^+$.

Example 2

Preparation of tert-butyl (6-chloro-5-nitro-2-(propylthio)pyrimidin-4-yl)((1R,2S)-2-(3,4-difluorophenyl)cyclopropyl)carbamate (CPABOCCIN)

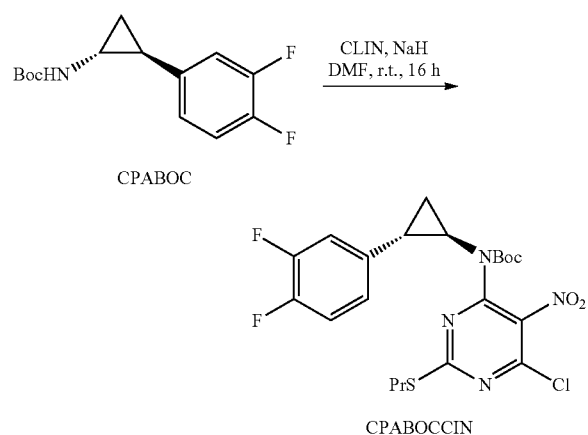

CPABOCCIN

A mixture of CPABOC (0.20 g, 0.74 mmol), CLIN (0.20 g, 0.74 mmol) and NaH (60% in oil, 36 mg, 0.74 mmol) in dry DMF (2 mL) was stirred at room temperature for 16 hours, then acetic acid (0.5 mL) and water (10 mL) were added. After extraction with diisopropyl ether (3×10 mL), the combined organic layers were dried over MgSO$_4$, and concentrated. Purification by chromatography (SiO$_2$, hexane: EtOAc) afforded title compound as yellow oil (0.23 g, 62% yield). $^1$H NMR (CDCl$_3$, 500 MHz) δ 0.95 (t, J=7.3 Hz, 3H), 1.22 (m, 1H), 1.29 (q, J=6.6 Hz, 1H), 1.36 (s, 9H), 1.66 (m, 2H), 2.17 (m, 1H), 2.94 (m, 1H), 3.03 (m, 1H), 3.08 (m, 1H), 6.58 (m, 1H), 6.94 (m, 1H), 7.01 (m, 1H).

Example 3

Preparation of tert-butyl ((1R,2S)-2-(3,4-difluorophenyl)cyclopropyl)(6-(((3aS,4R,6S,6aR)-6-hydroxy-2,2-dimethyltetrahydro-3aH-cyclopenta[d]-[1,3]dioxol-4-yl)amino)-5-nitro-2-(propylthio)pyrimidin-4-yl)carbamate (BAAL)

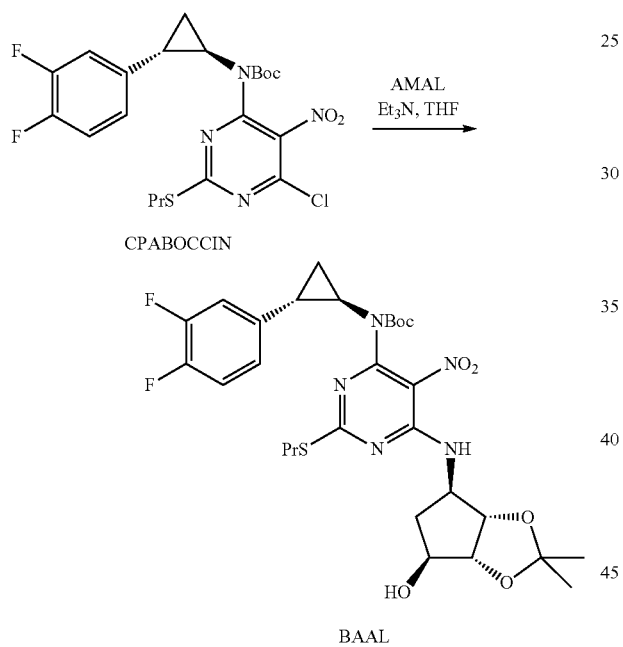

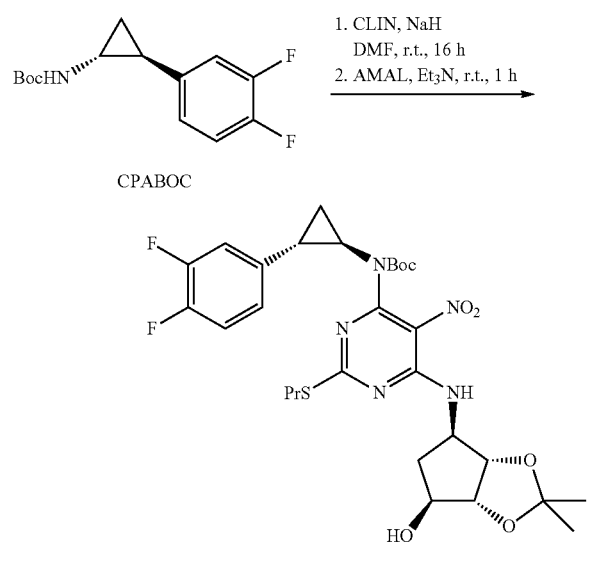

To a solution of CPABOCCIN (0.20 g, 0.40 mmol) and triethylamine (0.061 mL, 0.44 mmol) in dry THF (2 mL) was added AMAL (76 mg, 0.44 mmol). The resulting reaction mixture was stirred at room temperature for 1 h, then water was added (10 mL), and the product was extracted to THF (3×5 mL). Combined organic layers were dried over MgSO$_4$, and then concentrated. Purification by chromatography (SiO$_2$, hexane:EtOAc) afforded the title compound as a yellow oil (0.24 g, 93% yield). $^1$H NMR (CDCl$_3$, 500 MHz) δ 0.96 (t, J=7.3 Hz, 3H), 1.19 (s, 3H), 1.27 (m, 2H), 1.31 (s, 9H), 1.36 (s, 3H), 1.69 (m, 2H), 1.77 (m, 1H), 2.19 (br s, 1H), 2.26 (m, 1H), 2.67 (m, 1H), 2.91-3.08 (m, 3H), 4.29 (m, 1H), 4.46 (m, 1H), 4.52 (m, 1H), 4.68 (m, 1H), 6.88 (m, 1H), 6.94-7.01 (m, 2H), 8.64 (d, J=8.0 Hz, 1H); $^{19}$F NMR (CDCl$_3$, 470.5 MHz) δ −139.4 (m, 1F), −142.6 (m, 1F); MS (ESI) m/z: 638 [MH]$^+$.

BAAL was also prepared through one-pot reaction starting from CPABOC.

A mixture of CPABOC (1.0 g, 3.71 mmol), CLIN (1.0 g, 3.71 mmol) and NaH (60% in oil, 0.16 g, 4.08 mmol) in dry DMF (8 mL) was stirred at room temperature for 16 hours, then triethylamine (0.57 mL, 4.08 mmol) and AMAL (0.71 g, 4.08 mmol) were added at room temperature, and the resulting reaction mixture was stirred at room temperature for 1 h. Water (50 mL) was slowly added and product was extracted to diisopropyl ether (3×30 mL). Combined organic phases were dried over MgSO$_4$, then concentrated to afford crude compound, which was then purified by chromatography (SiO$_2$, hexane:EtOAc) to afford title compound as yellow oil (1.94 g, 82% yield).

Example 4

Preparation of tert-butyl (5-amino-6-(((3aS,4R,6S,6aR)-6-hydroxy-2,2-dimethyltetrahydro-3aH-cyclopenta[d][1,3]dioxol-4-yl)amino)-2-(propylthio)pyrimidin-4-yl)((1R,2S)-2-(3,4-difluorophenyl)cyclopropyl)carbamate (BAALA)

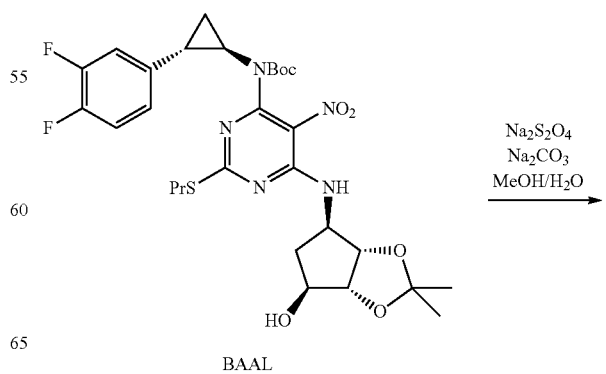

-continued

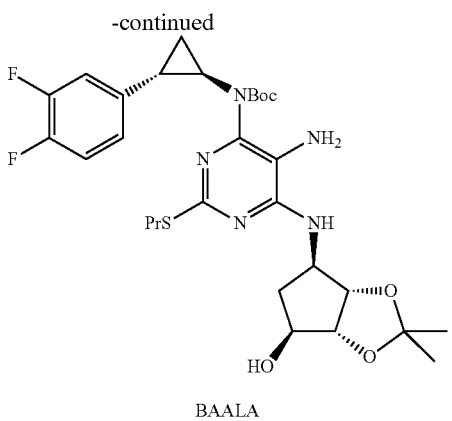

BAALA

A solution of BAAL (0.64 g, 1.0 mmol) in MeOH (2 mL) was added to a mixture of sodium dithionite (0.57 g, 3.3 mmol), Na$_2$CO$_3$ (0.35 g, 3.3 mmol), water (1 mL) and MeOH (1 mL). Resulting reaction mixture was stirred at 40° C. for 16 h, then water was added (30 mL), and product was extracted to EtOAc (3×20 mL). Combined organic phases were dried over MgSO$_4$, then concentrated to give a crude compound, which was then purified by chromatography (SiO$_2$, hexane: EtOAc) to afford the title compound as an orange oil (0.41 g, 68% yield). $^{19}$F NMR (CDCl$_3$, 470.5 MHz) δ −139.4 (m, 1F), −142.7 (m, 1F); MS (ESI) m/z: 608 [MH]$^+$.

BAALA was also prepared through a one-pot reaction starting from CPABOC.

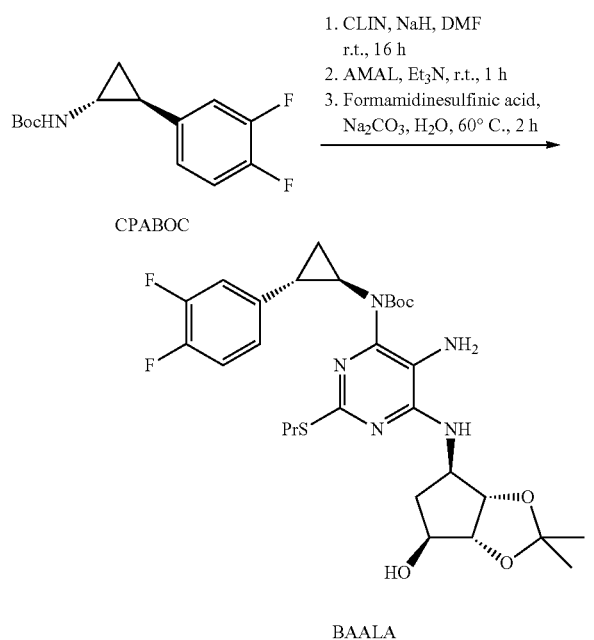

A mixture of CPABOC (1.0 g, 3.71 mmol), CLIN (1.0 g, 3.71 mmol) and NaH (60% in oil, 0.16 g, 4.08 mmol) in dry DMF (8 mL) was stirred at room temperature for 16 hours, then triethylamine (0.57 mL, 4.08 mmol) and AMAL (0.64 g, 3.71 mmol) were added at room temperature. The resulting reaction mixture was stirred at room temperature for 1 h. Then water (1 mL), Na$_2$CO$_3$ (1.29 g, 12.2 mmol) and formamidinesulfinic acid (1.32 g, 12.2 mmol) were added, and the resulting reaction mixture was stirred at 60° C. for 2 h. Water (100 mL) was added and the product was extracted to 2-methyltetrahydrofuran (3×30 mL). Combined organic phases were dried over MgSO$_4$, then concentrated to give a crude compound, which was then purified by chromatography (SiO$_2$, hexane:EtOAc) to afford the title compound as a orange oil (1.42 g, 63% yield).

Example 5

Preparation tert-butyl ((1R,2S)-2-(3,4-difluorophenyl)cyclopropyl)(3-((3aS,4R,6S,6aR)-6-hydroxy-2,2-dimethyltetrahydro-3aH-cyclopenta[d][1,3]dioxol-4-yl)-5-(propylthio)-3H-[1,2,3]triazolo[4,5-d]pyrimidin-7-yl)carbamate (BATAM)

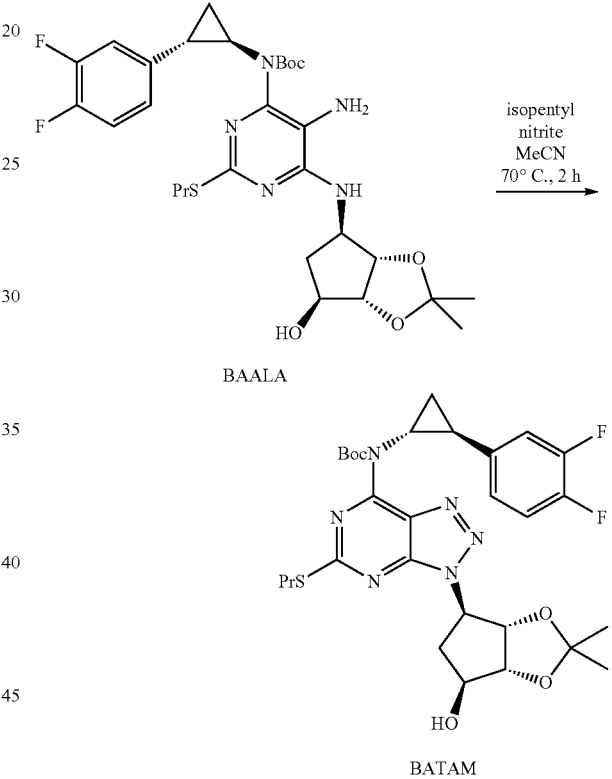

The title compound was prepared using the method described in WO 00/34283.

A solution of BAALA (0.40 g, 0.66 mmol) and isopentyl nitrite (0.13 mL, 1.0 mmol) in acetonitrile (4 mL) was stirred for 2 h at 70° C. Volatile components were then evaporated, and crude product was purified by chromatography (SiO$_2$, hexane:EtOAc) to afford the title compound as a yellow oil (0.40 g, 98% yield). $^1$H NMR (CDCl$_3$, 500 MHz) δ 0.99 (t, J=7.3 Hz, 3H), 1.22 (m, 1H), 1.25 (s, 3H), 1.38 (m, 1H), 1.42 (s, 9H), 1.47 (s, 3H), 1.72 (m, 2H), 2.12 (m, 1H), 2.23 (m, 1H), 2.84 (m, 1H), 2.99-3.05 (m, 1H), 3.07-3.14 (m, 1H), 3.17 (m, 1H), 4.28 (m, 1H), 4.36 (m, 1H), 4.72 (m, 1H), 4.86 (m, 1H), 5.30 (m, 1H), 6.90 (m, 1H), 6.98-7.04 (m, 2H); $^{19}$F NMR (CDCl$_3$, 470.5 MHz) δ −139.1 (m, 1F), −142.3 (m, 1F); MS (ESI) m/z: 619 [MH]+.

BATAM was also prepared through a one-pot reaction starting from CPABOC.

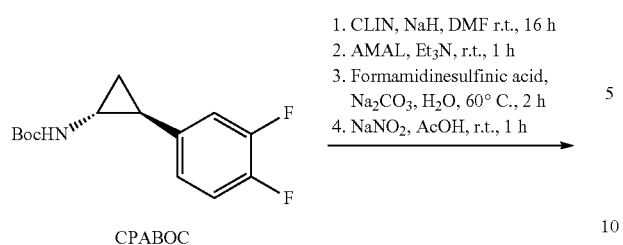

CPABOC

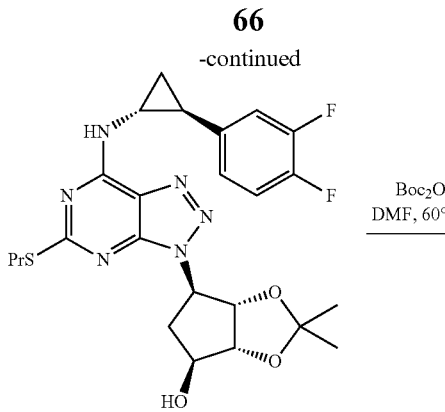

CPATAM

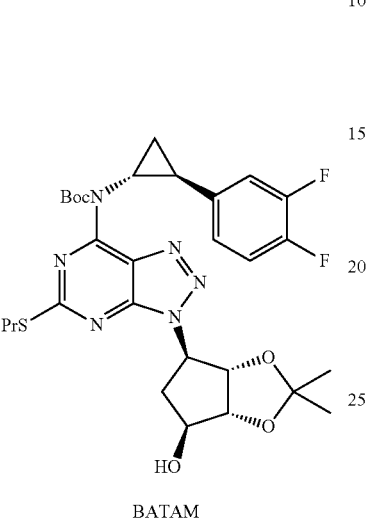

BATAM

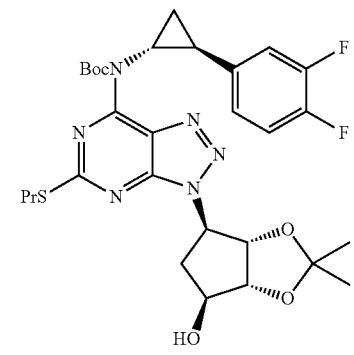

BATAM

A mixture of CPABOC (10.0 g, 37.1 mmol), CLIN (9.95 g, 37.1 mmol) and NaH (60% in oil, 1.63 g, 40.8 mmol) in dry DMF (50 mL) was stirred at room temperature for 16 hours, then triethylamine (5.69 mL, 40.8 mmol), and AMAL (6.43 g, 37.1 mmol) were slowly added at room temperature. The resulting reaction mixture was stirred at room temperature for 1 h, then water (20 mL), $Na_2CO_3$ (12.9 g, 122 mmol) and formamidinesulfinic acid (13.2 g, 122 mmol) were added, and the resulting reaction mixture was stirred at 60° C. for 2 h. The reaction mixture was then cooled to 0° C. Acetic acid (50 mL) was added dropwise over 2 h. $NaNO_2$ (3.84 g, 55.7 mmol) was then added and resulting reaction mixture was stirred at room temperature for 1 h. Water was added (500 mL), product was extracted to 2-methyltetrahydrofuran (3×100 mL), combined organic phases were dried over $MgSO_4$, then concentrated to afford crude product, which was purified by chromatography ($SiO_2$, hexane:EtOAc) to afford the title compound as yellow oil (12.0 g, 52% yield).

BATAM was also prepared from CLTAM via CPATAM.

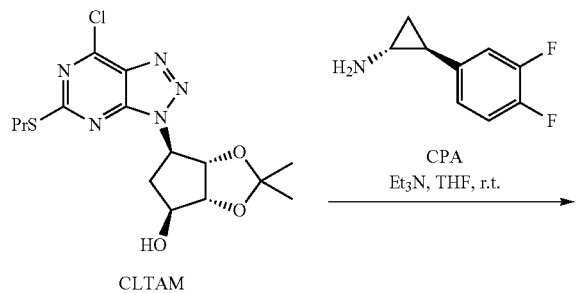

To a solution of CLTAM, which was prepared using the method described in WO 00/34283 (2.0 g, 5.18 mmol) and $Et_3N$ (0.13 mL, 1.0 mmol) in dry THF (7 mL) was slowly added at room temperature a solution of CPA in dry THF (3 mL). The resulting reaction mixture was stirred for 1 h, then salts were filtered off, and the filtrate was concentrated. CPATAM was then crystallized from hexane/diisopropyl ether mixture to afford a white powder (2.29 g, 85% yield). Mp 108° C.; $^1H$ NMR ($CDCl_3$, 500 MHz) δ 0.96 (t, J=7.2 Hz, 3H), 1.31 (s, 3H), 1.35-1.44 (m, 2H), 1.53 (s, 3H), 1.67 (m, 2H), 1.92 (m, 1H), 2.15 (m, 1H), 2.23 (m, 1H), 2.92 (m, 1H), 3.00 (m, 1H), 3.09 (m, 1H), 3.15 (m, 1H), 4.44 (m, 1H), 4.83 (m, 1H), 4.89 (m, 1H), 5.35 (d, J=8.4 Hz, 1H), 5.46 (m, 1H), 7.00 (m, 1H), 7.07-7.13 (m, 2H); $^{19}F$ NMR ($CDCl_3$, 470.5 MHz) δ −139.0 (m, 1F), −142.3 (m, 1F); MS (ESI) m/z: 519 [MH]$^+$.

A solution of CPATAM (2.0 g, 3.86 mmol) and $Boc_2O$ (0.93 g, 4.26 mmol) in DMF (10 mL) was stirred at 60° C. until TLC and HPLC analysis showed total conversion (several days). Then water (100 mL) was added, and product was extracted to 2-methyltetrahydrofuran (3×20 mL). The combined organic phases were dried over $MgSO_4$, and concentrated to give a crude product, which was then purified by chromatography ($SiO_2$, hexane:EtOAc) to afford a yellowish oil (0.82 g, 34% yield). $^1H$ NMR ($CDCl_3$, 500 MHz) δ 0.99 (t, J=7.3 Hz, 3H), 1.22 (m, 1H), 1.25 (s, 3H), 1.38 (m, 1H), 1.42 (s, 9H), 1.47 (s, 3H), 1.72 (m, 2H), 2.12 (m, 1H), 2.23 (m, 1H), 2.84 (m, 1H), 2.99-3.05 (m, 1H), 3.07-3.14 (m, 1H), 3.17 (m, 1H), 4.28 (m, 1H), 4.36 (m, 1H), 4.72 (m, 1H), 4.86 (m, 1H), 5.30 (m, 1H), 6.90 (m, 1H), 6.98-7.04 (m, 2H); $^{19}F$ NMR ($CDCl_3$, 470.5 MHz) δ −139.1 (m, 1F), −142.3 (m, 1F); MS (ESI) m/z: 619 [MH]$^+$.

Example 6

Preparation of methyl 2-(((3aR,4S,6R,6aS)-6-(7-((tert-butoxycarbonyl)((1R,2S)-2-(3,4-difluorophenyl)cyclopropyl)amino)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy) acetate (BATAME)

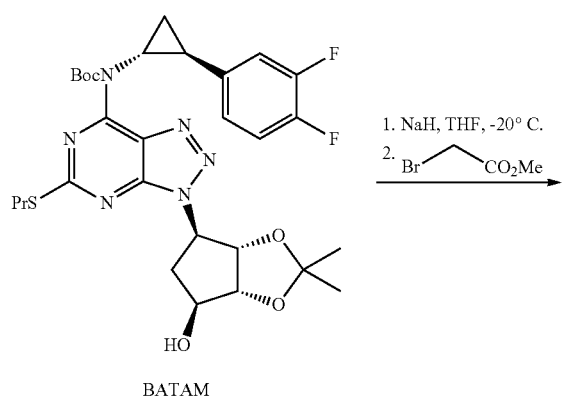

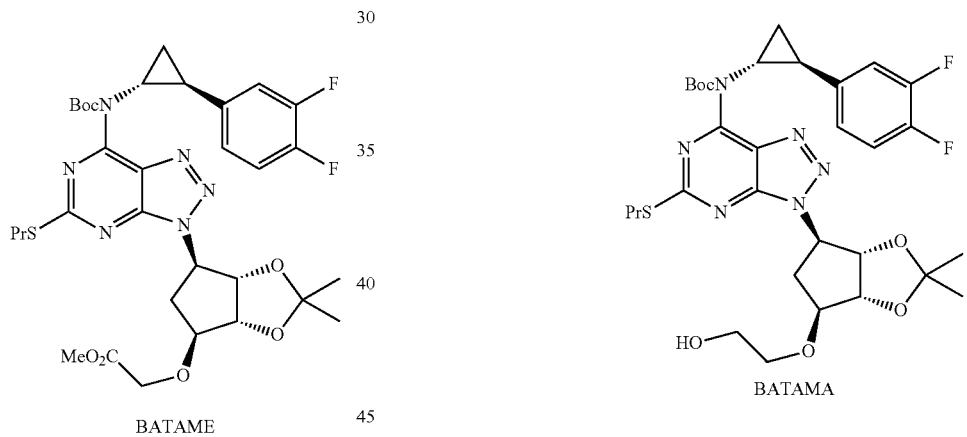

To a solution of BATAM (1.79 g, 2.89 mmol) in dry THF (10 mL) NaH (0.13 g, 3.18 mmol) was added at −20° C. and stirred for 1 h, then methyl bromoacetate (0.30 mL, 3.18 mmol) was added at −20° C. The resulting reaction mixture was stirred at −20° C. for 16 h. Acetic acid (5 mL) was added slowly, then water (50 mL) was added, and the product was extracted to 2-methyltetrahydrofuran (3×100 mL). The combined organic phases were washed with saturated NaHCO$_3$ (3×10 mL), dried over MgSO$_4$, and concentrated to give a crude product, which was then purified by chromatography (SiO$_2$, hexane:EtOAc). Colorless oil (1.60 g, 80% yield). $^1$H NMR (CDCl$_3$, 500 MHz) δ 0.99 (t, J=7.3 Hz, 3H), 1.21 (m, 1H), 1.28 (s, 3H), 1.36 (m, 1H), 1.40 (s, 9H), 1.48 (s, 3H), 1.73 (m, 2H), 2.14 (m, 1H), 2.68 (m, 2H), 3.00-3.11 (m, 2H), 3.18 (m, 1H), 3.65 (s, 3H), 4.01-4.10 (m, 3H), 4.76 (dd, J=6.8, 2.5 Hz, 1H), 5.11 (m, 1H), 5.42 (dd, J=6.8, 3.7 Hz, 1H), 6.91 (m, 1H), 6.97-7.05 (m, 2H); $^{19}$F NMR (CDCl$_3$, 470.5 MHz) δ −139.4 (m, 1F), −142.5 (m, 1F); MS (ESI) m/z: 691 [MH]$^+$.

Example 7

Preparation of tert-butyl ((1R,2S)-2-(3,4-difluorophenyl)cyclopropyl)(3-((3aS,4R,6S,6aR)-6-(2-hydroxyethoxy)-2,2-dimethyltetrahydro-3aH-cyclopenta[d][1,3]dioxol-4-yl)-5-(propylthio)-3H-[1,2,3]triazolo[4,5-d]pyrimidin-7-yl)carbamate (BATAMA)

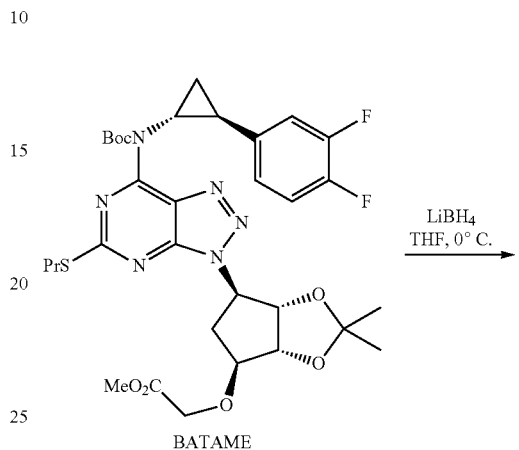

To a solution of BATAME (1.79 g, 2.89 mmol) in dry THF (10 mL) at 0° C. LiBH$_4$ (0.10 g, 4.63 mmol) was added and stirred for 16 h. The reaction was quenched by addition of saturated NaHCO$_3$ solution (5 mL). Water was added (50 mL), product was extracted to MeTHF (3×30 mL), combined organic phases were dried over MgSO$_4$, then concentrated to give a crude product, which was purified by chromatography (SiO$_2$, hexane:EtOAc) to afford the title compound as a colorless oil (1.20 g, 78% yield). $^1$H NMR (CDCl$_3$, 500 MHz) δ 1.07 (t, J=7.3 Hz, 3H), 1.29 (m, 1H), 1.37 (s, 3H), 1.43 (q, J=6.9 Hz, 1H), 1.48 (s, 9H), 1.56 (s, 3H), 1.80 (m, 2H), 2.21 (m, 1H), 2.26 (m, 1H), 2.56 (m, 1H), 2.70 (m, 1H), 3.07-3.20 (m, 2H), 3.26 (m, 1H), 3.49 (m, 1H), 3.52-3.66 (m, 3H), 4.05 (m, 1H), 4.87 (d, J=6.4 Hz, 1H), 5.22 (m, 1H), 5.53 (m, 1H), 6.98 (m, 1H), 7.04-7.12 (m, 2H); $^{19}$F NMR (CDCl$_3$, 470.5 MHz) δ −139.3 (m, 1F), −142.4 (m, 1F); MS (ESI) m/z: 663 [MH]$^+$.

BATAMA was also prepared through a one-pot reaction starting from BATAM.

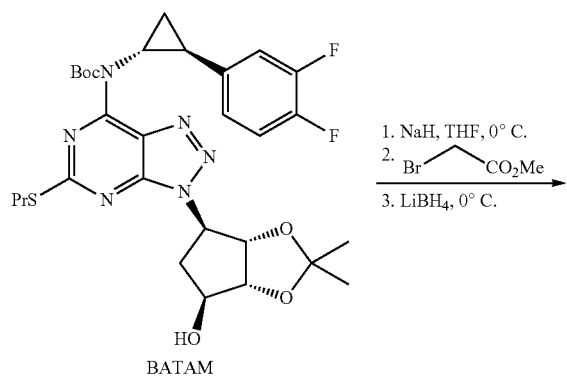

BATAM

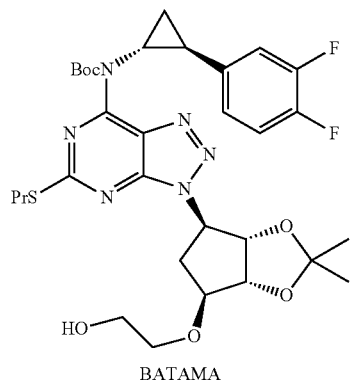

BATAMA

To a solution of BATAM (2.0 g, 3.23 mmol) in dry THF (10 mL) NaH (60% in oil, 0.14 g, 3.56 mmol) was added at 0° C. and stirred for 15 min, then methyl bromoacetate (0.36 mL, 3.80 mmol) was added, and the resulting reaction mixture was stirred at 0° C. for 2 h. Then LiBH$_4$ (0.14 g, 6.46 mmol) was added at 0° C. and stirred for 2 h. The reaction was quenched by addition of saturated NaHCO$_3$ solution (5 mL). Water was added (20 mL), product was extracted to MeTHF (3×10 mL), combined organic phases were dried over MgSO$_4$, then concentrated to give a crude product, which was purified by chromatography (SiO$_2$, hexane:EtOAc) to afford the title compound as colorless oil (0.42 g, 20% yield).

Example 8

Preparation of (1S,2S,3R,5S)-3-(7-(((1R,2S)-2-(3,4-difluorophenyl)cyclopropyl)amino)-5-(propylthio)-3H-[1,2,3]triazolo[4,5-c]pyrimidin-3-yl)-5-(2-hydroxyethoxy)cyclopentane-1,2-diol (TCG, ticagrelor)

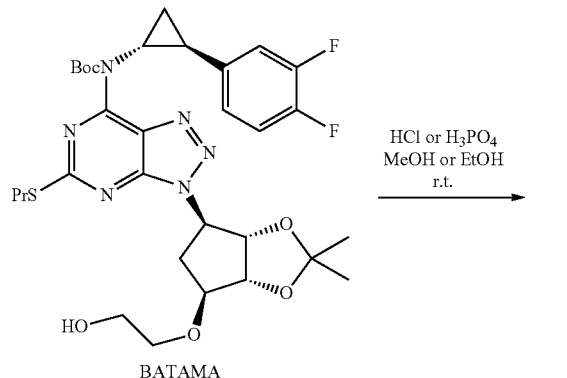

BATAMA

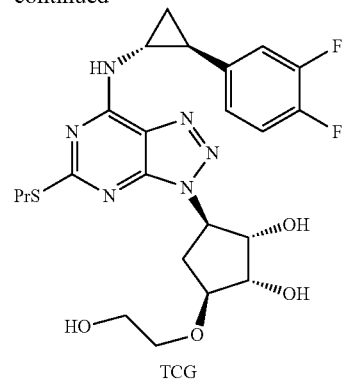

TCG

To a solution of BATAMA (0.25 g, 0.38 mmol) in EtOH (10 mL) at room temperature ortho-phosphoric acid (85%, 1.5 mL) was slowly added. The resulting reaction mixture was stirred at room temperature for 24 h. Water was then added (20 mL) and the reaction mixture neutralized with 1 M NaOH. The product was extracted to ethyl acetate (5×10 mL), the combined organic phases were dried over Na$_2$SO$_4$, then concentrated to give a crude product, which was purified by chromatography (SiO$_2$, EtOAc) to afford title compound as a white powder (0.17 g, 87% yield). $^{19}$F NMR (CD$_3$OD, 470.5 MHz) δ −141.9—−142.1 (m, 1F), −145.6—−145.9 (m, 1F); MS (ESI) m/z: 523 [MH]$^+$.

Example 9

Preparation of N-((1R,2S)-2-(3,4-difluorophenyl)cyclopropyl)-4-methylbenzene sulfonamide (CPATs)

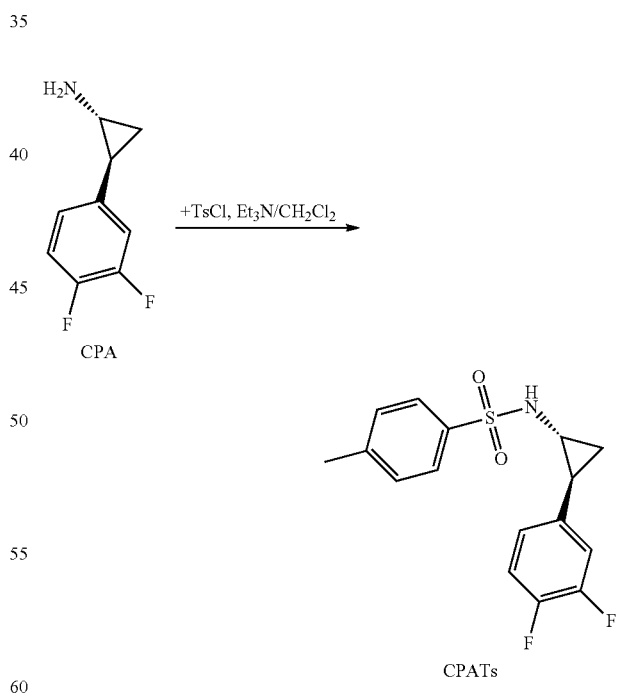

To a solution of CPA (16.92 g, 100 mmol) and triethylamine (17.4 mL, 125 mmol) in dichloromethane (140 mL) stirring in an ice bath was drop-wise added a solution of p-toluenesulfonyl chloride (20.02 g, 105 mmol) in dichloromethane (50 mL) in the course of 30 min. After 1 h reaction time there was added NH$_3$(aq) (25%, 10 mL), the mixture was left stirring for additional 10 min and then washed with water (300 mL), 1 M HCl (aq) (150 mL), water (300 mL) and evaporated under reduced pressure to give a white solid (31.45 g, 97% yield): $^1$H NMR (CDCl$_3$, 500 MHz) δ 1.06 (q, J=6.8 Hz, 1H), 1.26 (m, 1H), 2.11 (m, 1H), 2.31 (m, 1H), 2.43 (s, 3H), 5.33 (s, 1H), 6.74 (m, 2H), 7.02 (m, 1H), 7.29 (d, J=8.0 Hz, 2H), 7.73 (d, J=8.0 Hz, 2H); $^{19}$F NMR (CDCl$_3$, 470.5 MHz) δ −138.89 (m, 1F), −142.17 (m, 1F).

Example 10

Preparation of N-((1R,2S)-2-(3,4-difluorophenyl)cyclopropyl)naphthalene-2-sulfonamide (CPAN)

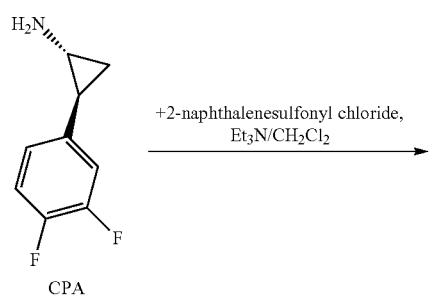

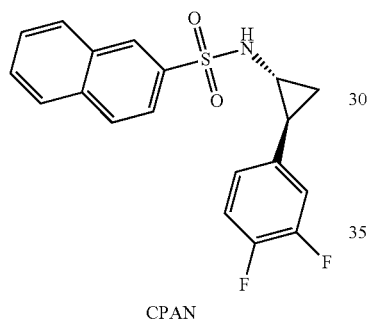

CPAN

Prepared in the same manner as CPATs (Example 9) by using 2-naphthalenesulfonyl chloride (11.90 g, 52.5 mmol) giving CPAN as a white solid (17.43 g, 97% yield): $^{19}$F NMR (CDCl$_3$, 470.5 MHz) δ −138.78 (m, 1F), −142.11 (m, 1F).

Example 11

Preparation of N-(6-chloro-5-nitro-2-(propylthio)pyrimidin-4-yl)-N-((1R,2S)-2-(3,4-difluorophenyl)cyclopropyl)-4-methylbenzenesulfonamide (CPTsCIN)

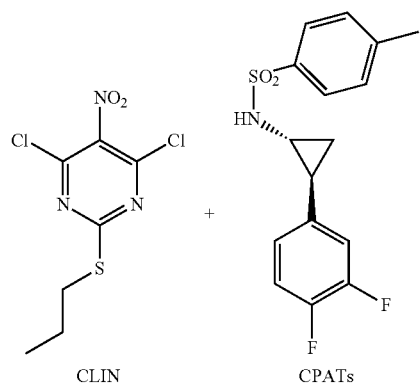

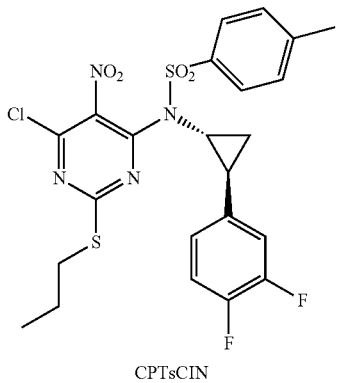

CPTsCIN

To a solution of CPATs (1.29 g, 4 mmol) and CLIN (1.07 g, 4 mmol) in acetonitrile (15 mL) was added anhydrous K$_3$PO$_4$ (1.27 g, 6 mmol) and the mixture stirred for 24 h at 25° C. The reaction mixture was then diluted with water (50 mL), extracted with diisopropyl ether (50 mL), the extract washed with water (2×50 mL) and evaporated under reduced pressure. The crude product was purified with flash chromatography to give a brownish resin (1.08 g, 49% yield): MS (ESI) m/z: 555 [MH]$^+$; $^{19}$F NMR (CDCl$_3$, 470.5 MHz) δ −138.43 (m, 1F), −141.32 (m, 1F).

Example 12

Preparation of N-(6-chloro-5-nitro-2-(propylthio)pyrimidin-4-yl)-N-((1R,2S)-2-(3,4-difluorophenyl)cyclopropyl)naphthalene-2-sulfonamide (CPNCIN)

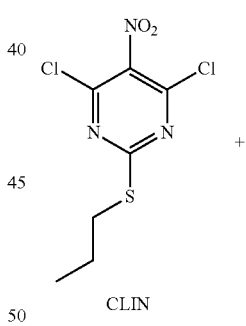

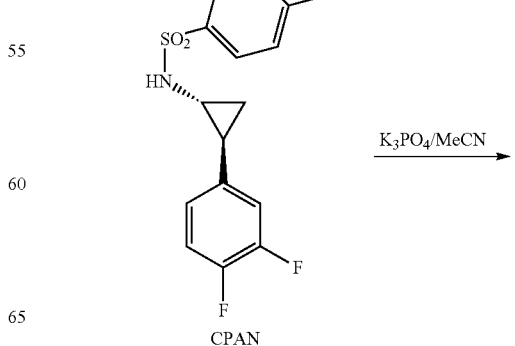

-continued

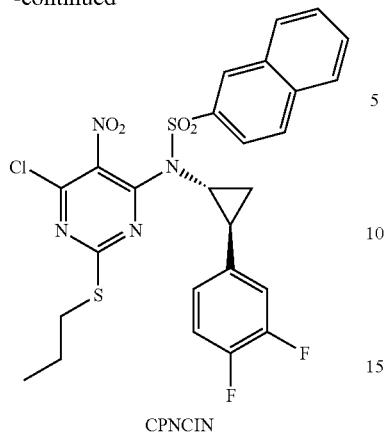

CPNCIN

To a solution of CPAN (1.44 g, 4 mmol) and CLIN (1.07 g, 4 mmol) in acetonitrile (15 mL) was added anhydrous $K_3PO_4$ (1.27 g, 6 mmol) and the mixture stirred for 48 h at 25° C. The reaction mixture was then diluted with water (50 mL), extracted with diisopropyl ether (50 mL), the extract washed with water (2×50 mL) and evaporated under reduced pressure. The crude product was purified with flash chromatography to give a brownish resin (1.56 g, 67% yield): MS (ESI) m/z: 591 [MH]+.

Example 13

Preparation of N-((1R,2S)-2-(3,4-difluorophenyl)cyclopropyl)-N-(6-(((3aS,4R,6S,6aR)-6-hydroxy-2,2-dimethyltetrahydro-3aH-cyclopenta[d][1,3]dioxol-4-yl)amino)-5-nitro-2-(propylthio)pyrimidin-4-yl)-4-methylbenzenesulfonamide (CTsAMCIN)

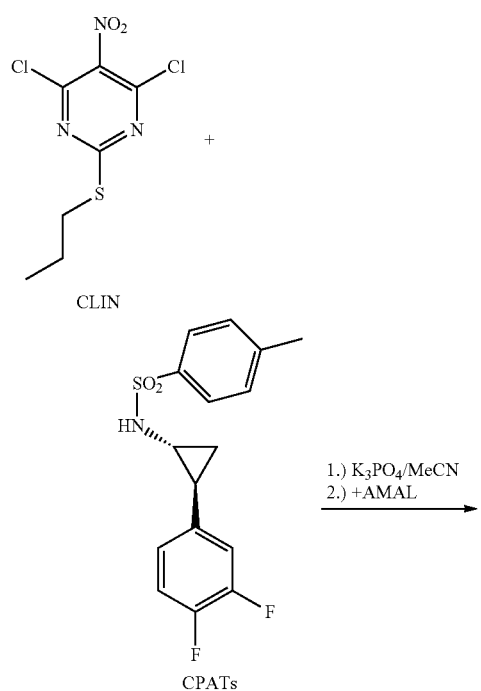

-continued

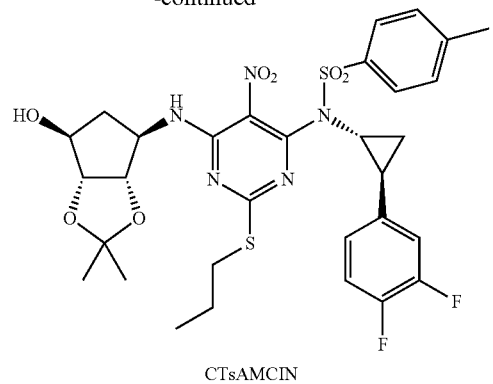

CTsAMCIN

To a solution of CPATs (1.29 g, 4 mmol) and CLIN (1.07 g, 4 mmol) in acetonitrile (15 mL) was added anhydrous $K_3PO_4$ (1.27 g, 6 mmol) and the mixture stirred for 24 h at 25° C. AMAL (0.66 g, 3.8 mmol) was then added and stirring continued for additional 2 h. The reaction mixture was then diluted with water (50 mL), extracted with diisopropyl ether (50 mL), the extract washed with water (2×50 mL) and evaporated under reduced pressure. The crude product was purified with flash chromatography to give an amorphous solid (2.14 g, 77% yield): 95 area % HPLC; MS (ESI) m/z: 692 [MH]+; $^{19}$F NMR (CDCl$_3$, 470.5 MHz) δ −138.93 (m, 1F), −141.97 (m, 1F).

Example 14

Preparation of N-(5-amino-6-(((3aS,4R,6S,6aR)-6-hydroxy-2,2-dimethyltetrahydro-3aH-cyclopenta[d][1,3]dioxol-4-yl)amino)-2-(propylthio)pyrimidin-4-yl)-N-((1R,2S)-2-(3,4-difluorophenyl)cyclopropyl)-4-methylbenzenesulfonamide (TAALA)

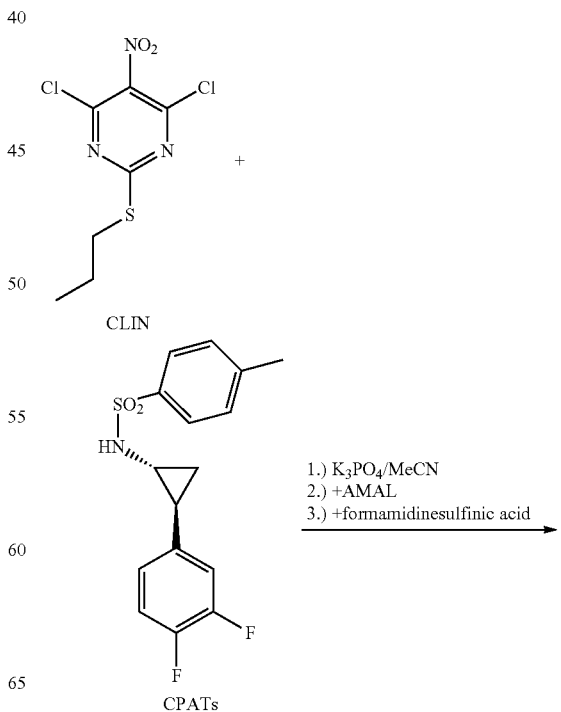

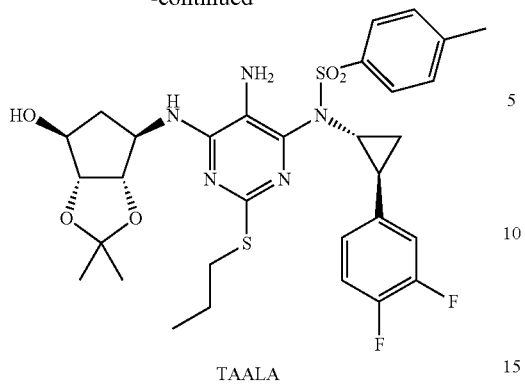

TAALA

A mixture of CLIN (0.96 g, 3.6 mmol), CPATs (1.29 g, 4 mmol) and K₃PO₄ (2.29 g, 10.8 mmol) in acetonitrile (15 mL) was stirred for 120 min at 25° C. AMAL (0.66 g, 3.8 mmol) was added and the mixture stirred for additional 2 hours. At this point formamidinesulfinic acid (1.36 g, 12.6 mmol) was added and the reaction temperature increased to 60° C. After 24 hours, the mixture was diluted with water (75 mL), extracted with ethyl acetate (50 mL), the extract washed with 0.1 M HCl(aq) (50 mL) and evaporated on a rotavapor to give a pale orange amorphous solid which was further purified by flash chromatography with hexane/ethyl acetate eluent (gradient from 4:1 to 1:1) to give TAALA as an light brown amorphous powder (1.20 g, 50% yield): MS (ESI) m/z: 662 [MH]⁺.

Example 15

Preparation of N-((1R,2S)-2-(3,4-difluorophenyl)cyclopropyl)-N-(3-((3aS,4R,6S,6aR)-6-hydroxy-2,2-dimethyltetrahydro-3aH-cyclopenta[d][1,3]dioxol-4-yl)-5-(propylthio)-3H-[1,2,3]triazolo[4,5-d]pyrimidin-7-yl)-4-methylbenzenesulfonamide (TATAM)

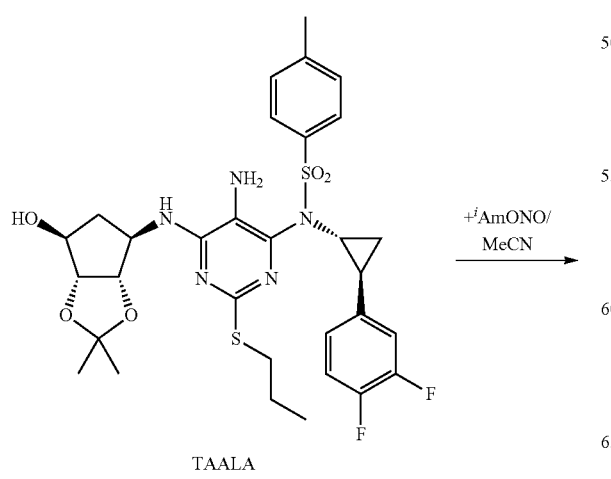

TAALA

+$^i$AmONO/ MeCN →

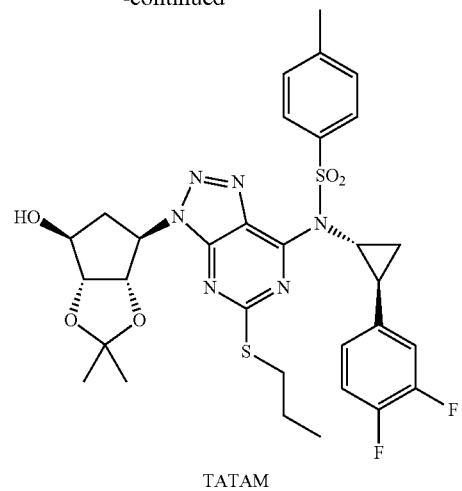

TATAM

To a solution of TAALA (500 mg, 0.75 mmol) in acetonitrile (5 mL) was added isopentyl nitrite (0.13 mL, 0.94 mmol) and the mixture stirred for 2 h at 60° C. The reaction mixture was then diluted with water (50 mL), extracted with diisopropyl ether (30 mL), the extract washed with water (2×50 mL) and evaporated under reduced pressure to give an off-white amorphous powder (450 mg, 89% yield): 97 area % HPLC; MS (ESI) m/z: 673 [MH]⁺.

TATAM was also prepared from CLTAM via CPATs.

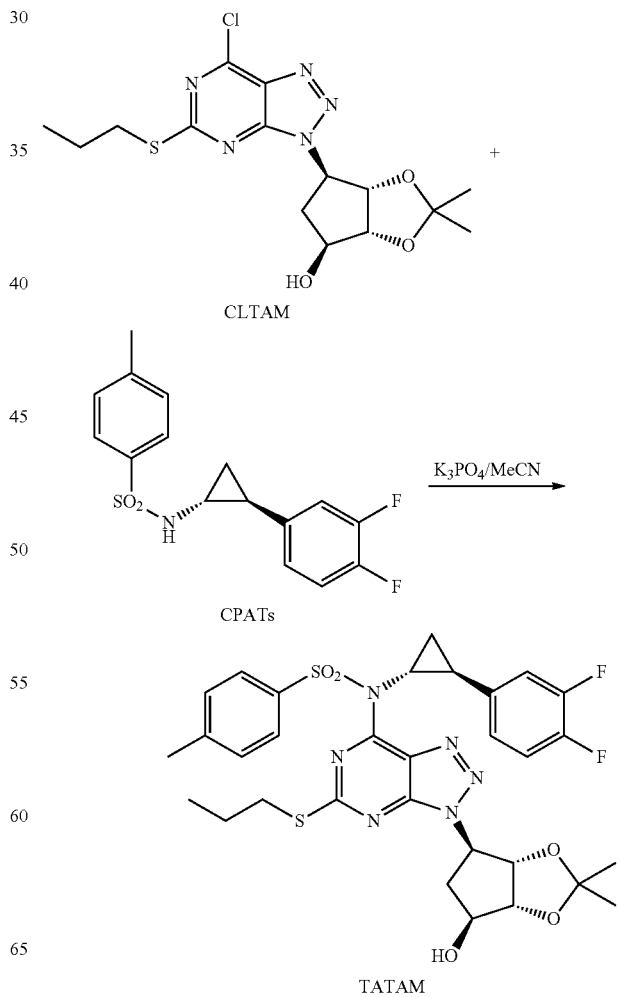

To a solution of CLTAM (1.16 g, 3 mmol), which was prepared using the method described in WO 00/34283, and CPATs (0.97 g, 3 mmol) in acetonitrile (20 mL) was added anhydrous $K_3PO_4$ (0.96 g, 4.5 mmol). After stirring for 24 h at 25° C., the mixture was diluted with water (80 mL) and extracted with diisopropyl ether (50 mL). The extract was washed with water (80 mL) and evaporated under reduced pressure to give a resinous crude product which was purified by flash chromatography to afford TATAM as an amorphous powder (1.52 g, 75% yield).

Example 16

Preparation of N-((1R,2S)-2-(3,4-difluorophenyl)cyclopropyl)-N-(3-((3aS,4R,6S,6aR)-6-hydroxy-2,2-dimethyltetrahydro-3aH-cyclopenta[d][1,3]dioxol-4-yl)-5-(propylthio)-3H-[1,2,3]triazolo[4,5-d]pyrimidin-7-yl)naphthalene-2-sulfonamide (NATAM)

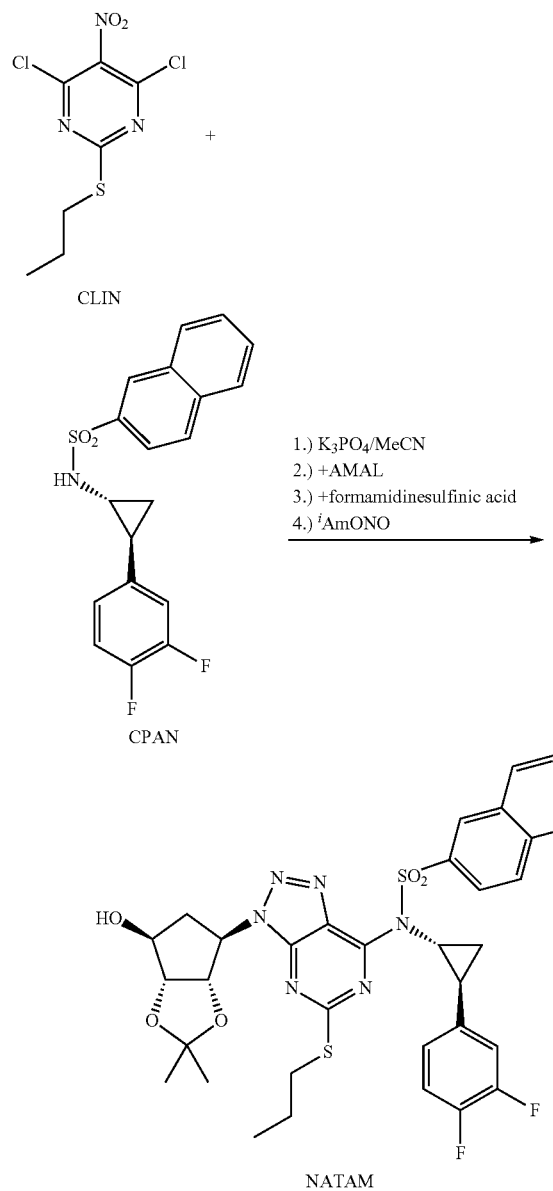

A mixture of CLIN (1.27 g, 4.75 mmol), CPAN (1.80 g, 5 mmol) and $K_3PO_4$ (3.03 g, 14.25 mmol) in acetonitrile (20 mL) was stirred for 150 min at 25° C. AMAL (0.78 g, 4.5 mmol) was added and the mixture stirred for additional 2 hours. At this point formamidinesulfinic acid (2.05 g, 19 mmol) was added and the reaction temperature increased to 60° C. After 18 hours, the mixture was diluted with water (100 mL), extracted with ethyl acetate (60 mL), the extract washed with 0.1 M HCl(aq) (60 mL) and evaporated under reduced pressure to give a brown resin (3.18 g). This was dissolved in ethyl acetate (30 mL), isopentyl nitrite (0.76 mL, 5.63 mmol) was added and the solution stirred for 1 h at 60° C. The brown solution was concentrated and the product isolated using flash chromatography with hexane/ethyl acetate eluent (gradient from 5:1 to 2:1). NATAM was thus obtained as a beige powder (1.86 g, 58% yield).

Example 17

Preparation of benzyl ((1R,2S)-2-(3,4-difluorophenyl)cyclopropyl)carbamate (CPAZ)

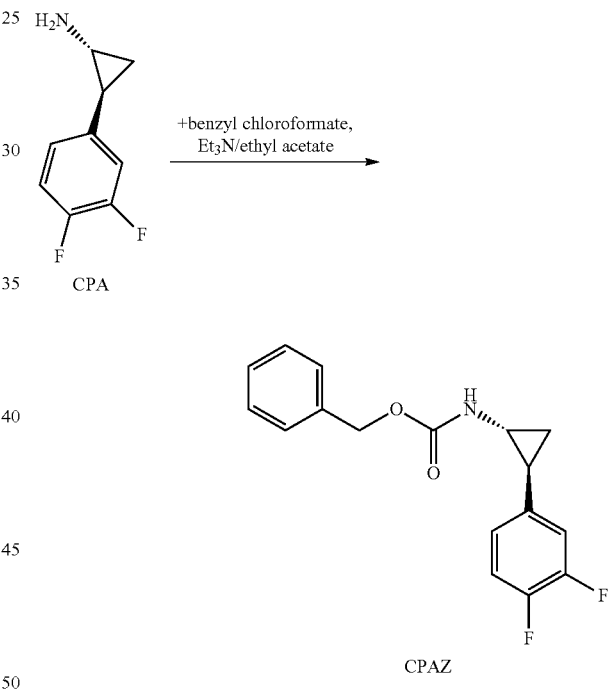

To a solution of CPA (11.84 g, 70 mmol) and triethylamine (12.2 mL, 87.5 mmol) in ethyl acetate (80 mL) stirring in an ice bath was drop-wise added a solution of benzyl chloroformate (11.0 mL, 77 mmol) in ethyl acetate (40 mL) at such a rate to maintain the reaction temperature bellow 15° C. After 1 h stirring in the ice bath, water (120 mL) was added and the mixture kept stirring for additional 30 min. The organic phase was separated, washed with 0.2 M HCl(aq) (200 mL), water (2×100 mL) and evaporated on a rotavapor. There was obtained a white solid (22.28 g) which was recrystallized from cyclohexane to give the product as a white crystalline solid (19.62 g, 92% yield): $^1$H NMR (CDCl$_3$, 500 MHz) δ 1.17 (m, 2H), 2.07 (m, 1H), 2.71 (m, 1H), 5.15 (s, 2H), 5.35 (bs, 1H), 6.70-7.10 (m, 3H), 7.33-7.42 (m, 5H); $^{19}$F NMR (CDCl$_3$, 470.5 MHz) δ −139.10 (m, 1F), −142.53 (m, 1F).

Example 18

Preparation of benzyl (6-chloro-5-nitro-2-(propylthio)pyrimidin-4-yl)((1R,2S)-2-(3,4-difluorophenyl)cyclopropyl)carbamate (CPZCIN)

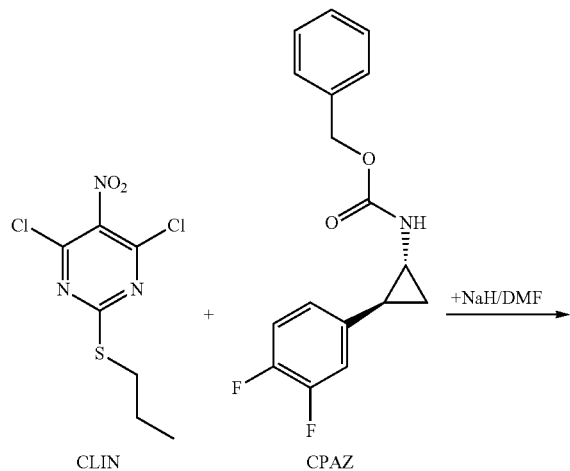

To a solution of CPAZ (4.85 g, 16 mmol) and CLIN (5.35 g, 20 mmol) in DMF (75 mL) stirring under a nitrogen atmosphere on an ice-bath was added 60% sodium hydride in oil (0.80 g, 20 mmol). After 1 h in an ice-bath, the reaction is stirred for 19 h at 25° C. The mixture is then diluted with 1% aqueous acetic acid (300 mL), extracted with ethyl acetate (200 mL), the extract washed with water (3×300 mL) and evaporated under reduced pressure. The crude product was purified by flash chromatography to give a yellow resin (5.31 g, 62% yield).

Example 19

Preparation of 6-chloro-N-((1R,2S)-2-(3,4-difluorophenyl)cyclopropyl)-5-nitro-2-(propylthio)pyrimidin-4-amine (CPACIN)

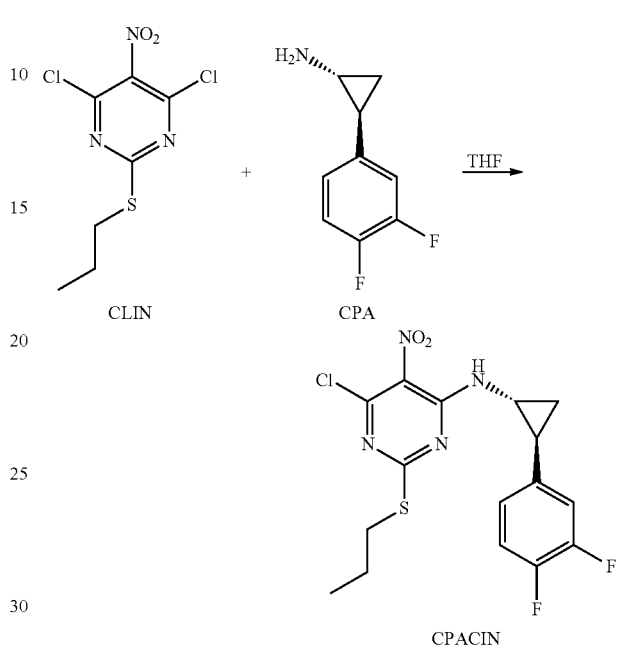

To a solution of CLIN (13.4 g, 50 mmol) in THF (150 mL) was added a solution of CPA (8.50 g, 50 mmol) at an addition rate of 10 mL/h while maintaining the reaction temperature at 0° C. After the addition, the reaction mixture was then stirred at 25° C. for 4 days. n-Hexane (200 mL) was then added and the mixture diluted with water (500 mL). The organic phase was then washed with water and evaporated under reduced pressure to give a crude product which was purified by flash chromatography to afford CPACIN as a crystalline product (12.2 g, 61% yield): MS (ESI) m/z: 401 [MH]$^+$.

Example 20

Preparation of (1S,2S,3R,5S)-3-amino-5-(2-hydroxyethoxy)cyclopentane-1,2-diol (OLA=VII)

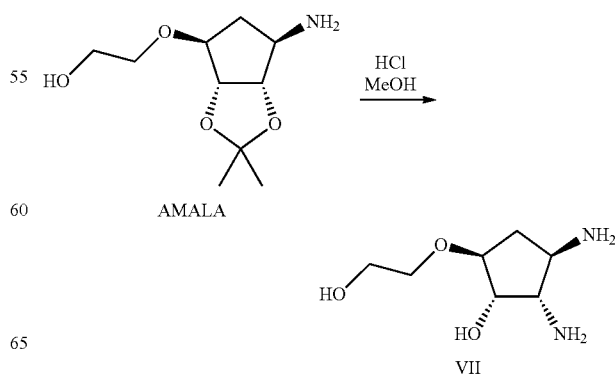

AMALA was prepared according to the process described in WO01/92263.

A solution of AMALA (1.0 g, 4.60 mmol) and 3 M HCl (5 mL) in MeOH (15 mL) was stirred at room temperature for 24 hours. Solvents were then evaporated to dryness. 2-Propanol (20 mL) and Na$_2$CO$_3$ (2.0 g) was added to the residue. The resulting mixture was stirred at room temperature for 24 h. Insoluble salts were then filtered off and filtrate was concentrated to afford title compound as a colorless oil (0.57 g, 80% yield): $^1$H NMR (DMSO-d$_6$) δ=1.07 (m, 1H), 2.19 (m, 1H), 2.87 (dd, J=14.7, 7.8 Hz, 1H), 3.00-3.60 (m, 10H), 3.53 (m, 1H), 3.74 (dd, J=5.4, 3.4, 1H); $^{13}$C NMR (DMSO-d$_6$) δ=36.4, 55.0, 60.4, 70.7, 75.1, 78.7, 83.3; MS (ESI) m/z: 178 [MH]$^+$.

Example 21

Preparation of tert-butyl ((1R,2S)-2-(3,4-difluorophenyl)cyclopropyl)(6-(((1R,2S,3S,4S)-2,3-dihydroxy-4-(2-hydroxyethoxy)cyclopentyl)amino)-5-nitro-2-(propylthio)pyrimidin-4-yl)carbamate (BAALOA)

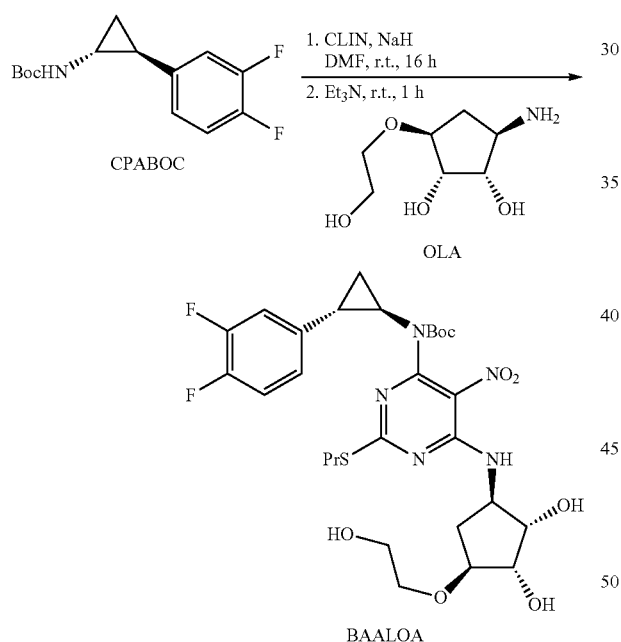

A mixture of CPABOC (1.31 g, 4.87 mmol), CLIN (1.30 g, 3.71 mmol) and NaH (60% in oil, 0.21 g, 5.36 mmol) in dry DMF (10 mL) was stirred at room temperature for 16 hours, then triethylamine (0.75 mL, 5.36 mmol) and OLA (0.90 g, 5.08 mmol) were added at room temperature, and the resulting reaction mixture was stirred at room temperature for 2 h. Water (70 mL) was slowly added and product was extracted to MeTHF (3×20 mL). Combined organic phases were dried over MgSO$_4$, then concentrated to afford crude compound, which was then purified by chromatography (SiO$_2$, hexane: EtOAc) to afford title compound as yellow oil (2.53 g, 81% yield). MS (ESI) m/z: 642 [MH]$^+$.

Example 22

Preparation of tert-butyl (5-amino-6-(((1R,2S,3S,4S)-2,3-dihydroxy-4-(2-hydroxy ethoxy)cyclopentyl)amino)-2-(propylthio)pyrimidin-4-yl)((1R,2S)-2-(3,4-difluorophenyl)cyclopropyl)carbamate (BAALOAA)

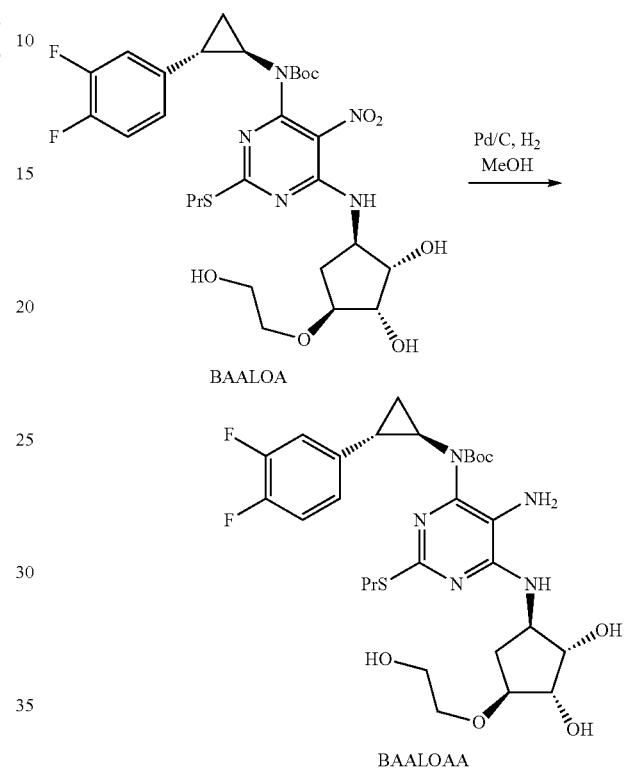

A mixture of BAALOA (0.66 g, 1.03 mmol) and Pd/C (5%, 70 mg) in MeOH (7 mL) was hydrogenated under 10 bar H$_2$ for 16 h. Catalyst was then filtered off and filtrate was concentrated to afford title compound as yellow syrup (0.56 g, 89% yield). MS (ESI) m/z: 612 [MH]$^+$.

Example 23

Preparation tert-butyl ((1R,2S)-2-(3,4-difluorophenyl)cyclopropyl)(3-((1R,2S,3S,4S)-2,3-dihydroxy-4-(2-hydroxyethoxy)cyclopentyl)-5-(propylthio)-3H-[1,2,3]triazolo[4,5-d]pyrimidin-7-yl)carbamate (BATOMA)

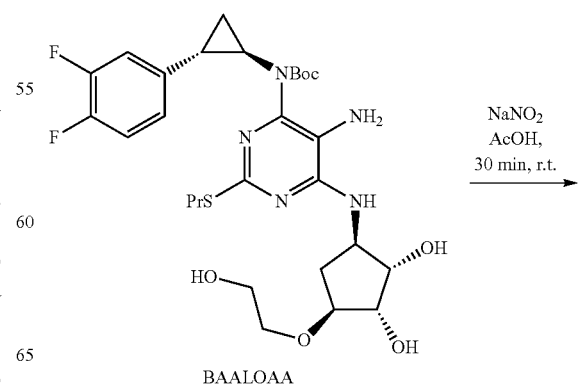

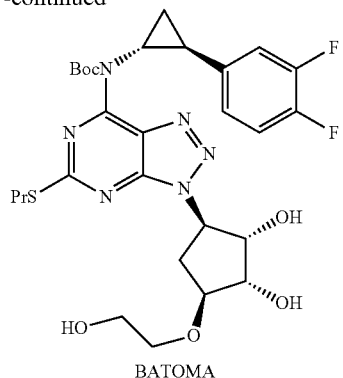

BATOMA

To a solution of BAALOAA (0.60 g, 0.98 mmol) in AcOH (5 mL) was added NaNO$_2$ (81 mg, 1.18 mmol). Resulting reaction mixture was stirred for 30 min at room temperature. Water (50 mL) was added and product was extracted to MeTHF (3×20 mL). Combined organic phases were dried over MgSO$_4$, then concentrated to afford crude compound, which was then purified by chromatography (SiO$_2$, hexane: EtOAc) to afford title compound as yellowish syrup (0.58 g, 96% yield). MS (ESI) m/z: 623 [MH]$^+$.

Example 24

Preparation of (1S,2S,3R,5S)-3-(7-(((1R,2S)-2-(3,4-difluorophenyl)cyclopropyl)amino)-5-(propylthio)-3H-[1,2,3]triazolo[4,5-d]pyrimidin-3-yl)-5-(2-hydroxyethoxy)cyclopentane-1,2-diol (TCG)

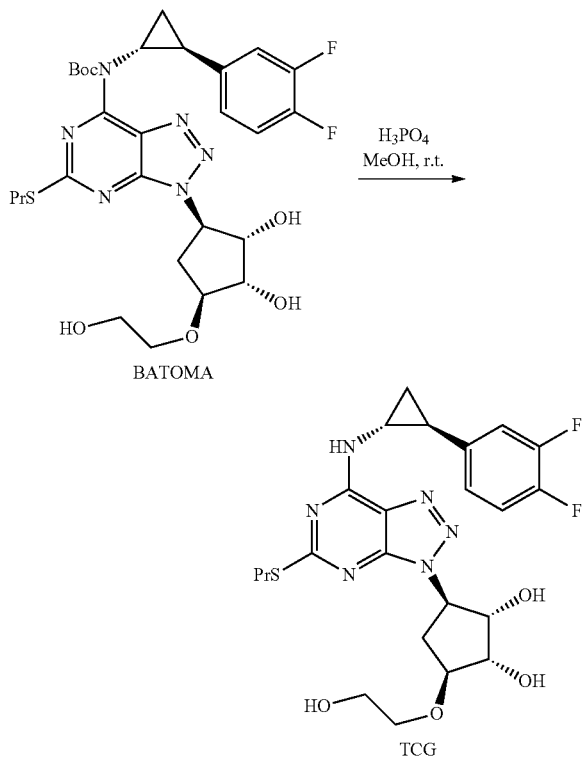

To a solution of BATOMA (0.10 g, 0.15 mmol) in MeOH (4 mL) at room temperature ortho-phosphoric acid (85%, 1.5 mL) was added. Resulting reaction mixture was stirred at room temperature for 24 h, then water was added (10 mL), and reaction mixture was neutralized with 1 M NaOH. The product was extracted to EtOAc (5×5 mL), combined organic phases were dried over Na$_2$SO$_4$, and then concentrated to afford crude product, which was purified by chromatography (SiO$_2$, EtOAc) to afford title compound as a white powder (66 mg, 84% yield). MS (ESI) m/z: 523 [MH]$^+$.

Example 25

Preparation of (3aS,4R,6S,6aR)-N-benzyl-6-(2-tert-butoxy)ethoxy)-2,2-dimethyltetrahydro-3aH-cyclopenta[d][1,3]dioxol-4-amine (BAMALAT)

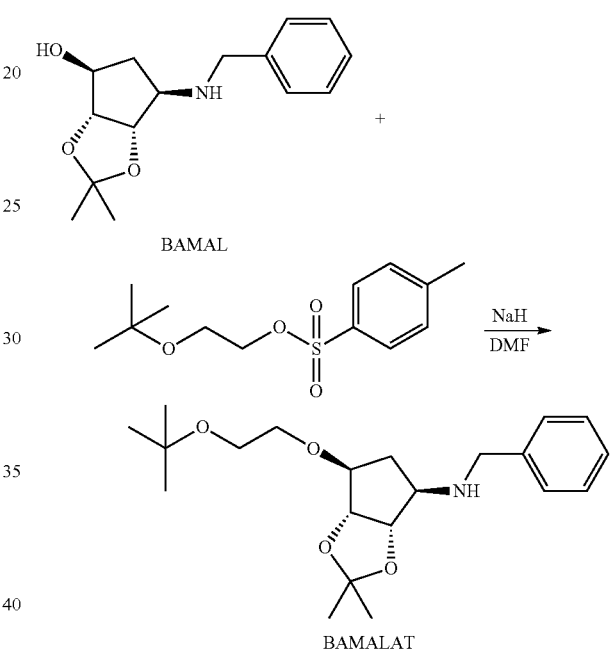

A solution of 10 g (38 mmol) of (3aR,4S,6R,6aS)-6-(benzylamino)-2,2-dimethyltetrahydro-3aH-cyclopenta[d][1,3]dioxol-4-ol (BAMAL, prepared according to J. Org. Chem. 70, 6884 (2005)) in dry DMF (100 mL) under nitrogen atmosphere was cooled at 0° C. followed by addition of NaH (60%, 1.8 g, 46 mmol). After stirring for 30 min at 0° C., 2-(tert-butoxy)ethyl 4-methylbenzenesulfonate (10.3 g, 38 mmol) was added and the reaction mixture was allowed to warm at room temperature. After stirring for 4 hours, the reaction mixture was quenched with water (100 mL). The mixture was extracted 3×100 mL of n-hexane. The combined organic phases were dried over MgSO$_4$, filtered and evaporated to the dryness.

Obtained BAMALAT was isolated from the reaction mixture by salt formation with fumaric acid. The solution of reaction mixture of BAMALAT (contained about 60% of BAMALAT) in 2-butanone was warmed to 50° C. 1 eq of fumaric acid (calculated to amount of BAMALAT) was added and reaction mixture was stirred at 50° C. until fumaric acid dissolution. The reaction mixture was allowed to cool at room temperature followed by addition of n-hexane. After overnight stirring at room temperature, the precipitated white salt of BAMALAT was sucked off, washed with n-hexane and dried under reduce pressure at 40° C.

Fumarate salt of BAMALAT was suspended in EtOAc and 5% aqueous solution of NaHCO₃ was added to the suspension. The mixture was stirred vigorously at room temperature for an hour. The two clear phases were separated and organic phase was washed with water, dried over MgSO₄ and evaporated to the dryness to provide pure BAMALAT. ¹H NMR (CDCl₃) δ=1.14 (s, 9H), 1.30 (s, 3H), 1.40 (s, 3H), 1.88 (d, 1H), 2.10 (m, 1H), 3.14 (m, 1H), 3.45 (m, 2H), 3.59 (m, 2H), 3.80-3.90 (m, 3H), 4.62 (m, 2H), 7.22-7.35 (m, 5H) ppm. 13C NMR (CDCl3) δ=24.0, 26.4, 27.4, 33.8, 51.7, 60.1, 63.1, 69.1, 72.9, 83.9, 84.6, 84.8 110.2, 126.7, 128.1, 128.2, 140.3 ppm.

Example 26

3aS,4R,6S,6aR)-6-(2-(tert-butoxy)ethoxy)-2,2-dimethyltetrahydro-3aH-cyclopenta[d][1,3]dioxol-4-amine (TBUAM

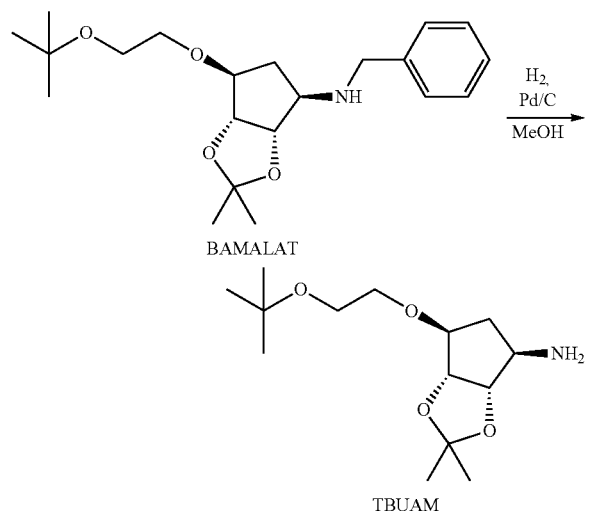

The solution of BAMALAT (6.0 g, 16.5 mmol) in MeOH (50 mL) was hydrogenated at 5 bar of hydrogen for 16 hours at 50° C. in the presence of Pd/C (10%, 0.6 g). The reaction mixture was passed through the pad of Celite and evaporated to the dryness to provide TBUAM. ¹H NMR (CDCl₃) δ=1.13 (s, 9H), 1.23 (s, 3H), 1.36 (s, 3H), 1.74 (d, 1H), 2.06 (m, 1H), 3.25 (d, 1H), 3.43 (m, 2H), 3.55 (m, 2H), 3.81 (d, 1H), 4.38 (d, 1H), 4.61 (d, 1H) ppm. ¹³C NMR (CDCl₃) δ=23.8, 26.2, 27.4, 35.2, 57.8, 60.8, 68.8, 72.8, 84.0, 85.1, 88.5, 109.8 ppm.

Example 27

Preparation of tert-butyl (6-(((3aS,4R,6S,6aR)-6-(2-(tert-butoxy)ethoxy)-2,2-dimethyltetrahydro-3aH-cyclopenta[d][1,3]dioxol-4-yl)amino)-5-nitro-2-(propyl thio)pyrimidin-4-yl)((1R,2S)-2-(3,4-difluorophenyl)cyclopropyl)carbamate (BAALAT)

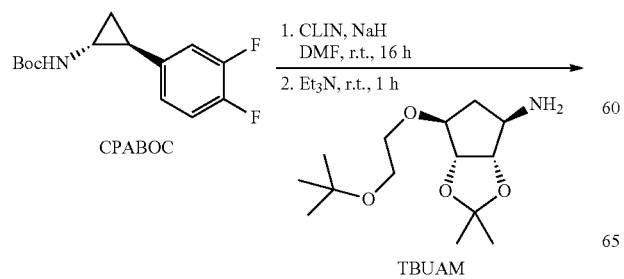

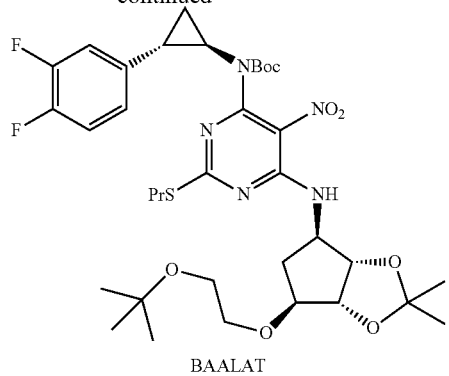

A mixture of CPABOC (1.06 g, 3.95 mmol), CLIN (1.06 g, 3.95 mmol) and NaH (60% in oil, 0.17 g, 4.35 mmol) in dry DMF (10 mL) was stirred at room temperature for 16 hours, then triethylamine (0.61 mL, 4.35 mmol) and TBUAM (1.08 g, 3.95 mmol) were added at room temperature, and the resulting reaction mixture was stirred at room temperature for 2 h. Water (70 mL) was slowly added and product was extracted to MeTHF (3×20 mL). Combined organic phases were dried over MgSO₄, then concentrated to afford crude compound, which was then purified by chromatography (SiO₂, hexane:EtOAc) to afford title compound as yellow oil (2.13 g, 73% yield).

Example 28

Preparation of tert-butyl (5-amino-6-(((3aS,4R,6S,6aR)-6-(2-(tert-butoxy)ethoxy)-2,2-dimethyltetrahydro-3aH-cyclopenta[d][1,3]dioxol-4-yl)amino)-2-(propylthio) pyrimidin-4-yl)((1R,2S)-2-(3,4-difluorophenyl)cyclopropyl)carbamate (BAALATA)

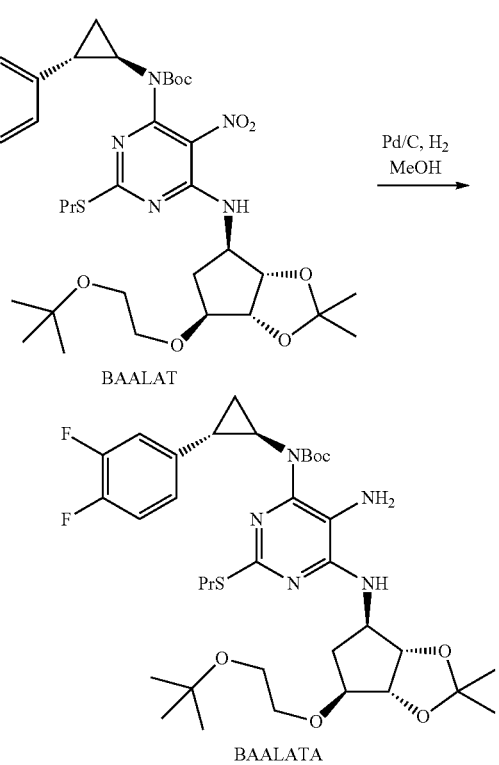

A mixture of BAALAT (0.50 g, 1.03 mmol) and Pd/C (5%, 50 mg) in MeOH (5 mL) was hydrogenated under 10 bar of hydrogen for 16 h. Catalyst was then filtered off and filtrate was concentrated to afford crude compound, which was then purified by chromatography (SiO$_2$, hexane:EtOAc) to afford title compound as yellow oil (0.44 g, 92% yield). MS (ESI) m/z: 708 [MH]$^+$.

Example 29

Preparation tert-butyl (3-((3aS,4R,6S,6aR)-6-(2-(tert-butoxy)ethoxy)-2,2-dimethyltetrahydro-3aH-cyclopenta[d][1,3]dioxol-4-yl)-5-(propylthio)-3H-[1,2,3]triazolo[4,5-d]pyrimidin-7-yl)((1R,2S)-2-(3,4-difluorophenyl)cyclopropyl) carbamate (BATAMAT)

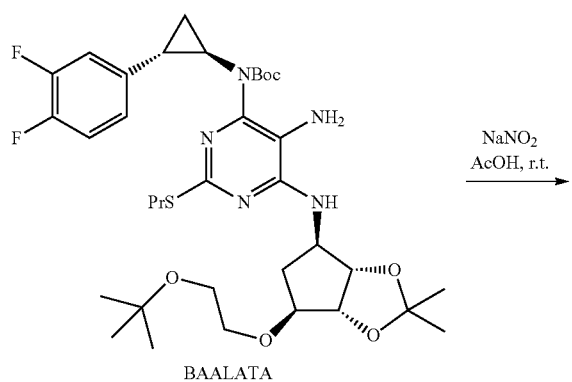

BAALATA

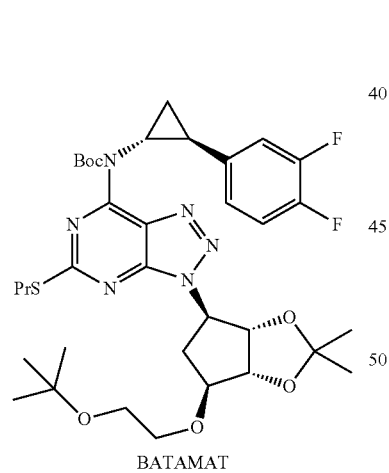

BATAMAT

To a solution of BAALATA (0.35 g, 0.49 mmol) in AcOH (5 mL) was added NaNO$_2$ (41 mg, 0.59 mmol). Resulting reaction mixture was stirred for 1 h at room temperature. Water (50 mL) was added and product was extracted to MeTHF (3×10 mL). Combined organic phases were dried over MgSO$_4$, then concentrated to afford crude compound, which was then purified by chromatography (SiO$_2$, hexane:EtOAc) to afford title compound as yellow oil (0.33 g, 95% yield). MS (ESI) m/z: 719 [MH]$^+$.

Example 30

Preparation of (1S,2S,3R,5S)-3-(7-(((1R,2S)-2-(3,4-difluorophenyl)cyclopropyl)amino)-5-(propylthio)-3H-[1,2,3]triazolo[4,5-c]pyrimidin-3-yl)-5-(2-hydroxy ethoxy)cyclopentane-1,2-diol (TCG)

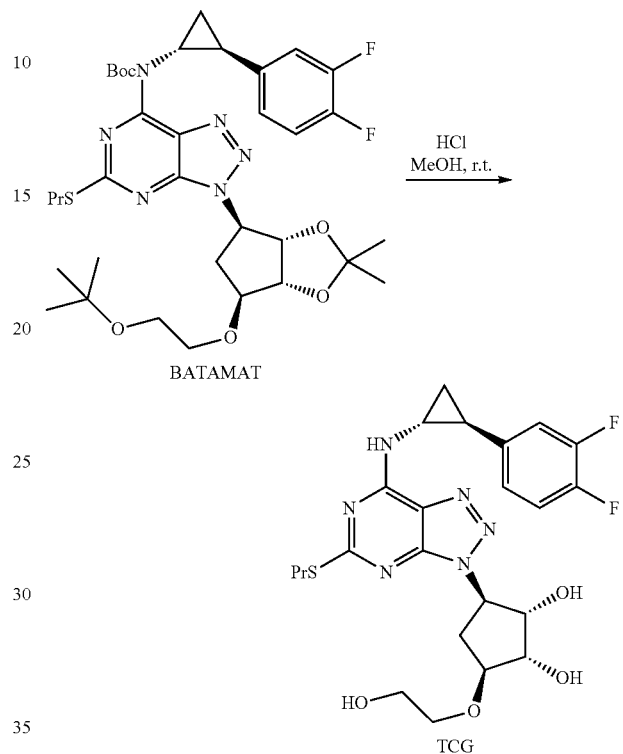

To a solution of BATAMAT (0.10 g, 0.14 mmol) in MeOH (4 mL) at room temperature 37% HCl (1 mL) was added. Resulting reaction mixture was stirred at room temperature and monitored by TLC and HPLC. After total conversion (several days) water was added (10 mL), and reaction mixture was neutralized with 1 M NaOH. The product was extracted to EtOAc (5×5 mL), combined organic phases were dried over Na$_2$SO$_4$, and then concentrated to afford crude product, which was purified by chromatography (SiO$_2$, EtOAc) to afford title compound as a white powder (50 mg, 63% yield). MS (ESI) m/z: 523 [MH]$^+$.

Example 31

Preparation of N-((1R,2S)-2-(3,4-difluorophenyl)cyclopropyl)methanesulfonamide (CPAMs)

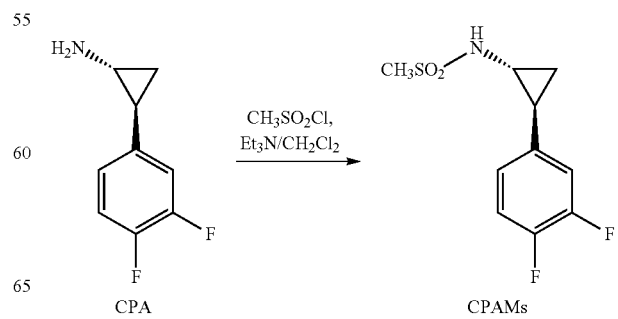

To a solution of CPA (6.77 g, 40 mmol) and triethylamine (6.70 mL, 50 mmol) in dichloromethane (60 mL) at 0° C. was slowly added a solution of methanesulfonyl chloride (3.87 mL, 50 mmol) in dichloromethane (20 mL) in the course of 3 h. After two additional hours of stirring, the reaction mixture was washed with 1 M HCl (aq) (60 mL) and water (60 mL), and then evaporated under reduced pressure to give a crude product (9.89 g) which was recrystallized from an ethanol/water mixture to give the title compound as a white crystalline product (7.60 g, 77% yield): $^1$H NMR (CDCl$_3$, 500 MHz) δ=1.24 (m, 1H), 1.38 (m, 1H), 2.31 (m, 1H), 2.70 (m, 1H), 3.05 (s, 3H), 4.85 (s, 1H), 6.90 (m, 1H), 6.96 (m, 1H), 7.10 (m, 1H); $^{19}$F NMR (CDCl$_3$, 470.5 MHz) δ=−141.67 (m, 1F), −138.46 (m, 1F).

Example 32

Preparation of N-(6-chloro-5-nitro-2-(propylthio)pyrimidin-4-yl)-N-((1R,2S)-2-(3,4-difluorophenyl)cyclopropyl)methanesulfonamide (CPMsCIN)

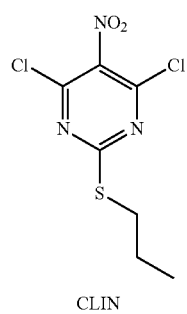

CLIN

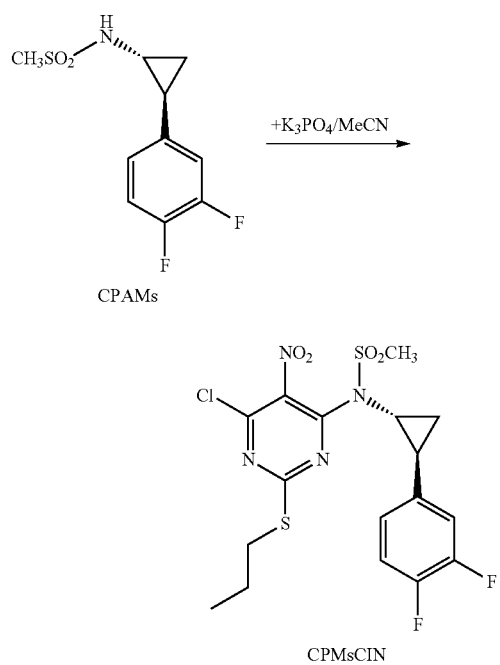

CPAMs

CPMsCIN

To a solution of CPAMs (1.98 g, 8 mmol) and CLIN (2.14 g, 8 mmol) in acetonitrile (30 mL) was added anhydrous K$_3$PO$_4$ (3.40 g, 16 mmol) and the mixture stirred for 24 h at 25° C. The reaction mixture was then diluted with water (100 mL), extracted with diisopropyl ether (50 mL), the extract washed with water (2×100 mL) and evaporated under reduced pressure. The crude product was purified with flash chromatography to give a yellowish resin (2.32 g, 61% yield): $^{19}$F NMR (CDCl$_3$, 470.5 MHz) δ=−140.83 (m, 1F), −138.14 (m, 1F).

Example 33

Preparation of methyl 2-(((3aR,4S,6R,6aS)-6-(7-(N-((1R,2S)-2-(3,4-difluoro-phenyl)cyclopropyl)-4-methylphenylsulfonamido)-5-(propylthio)-3H-[1,2,3]triazolo[4,5-d]pyrimidin-3-yl)-2,2-dimethyltetrahydro-3aH-cyclopenta[d][1,3]dioxol-4-yl)-oxy)acetate (TATAME)

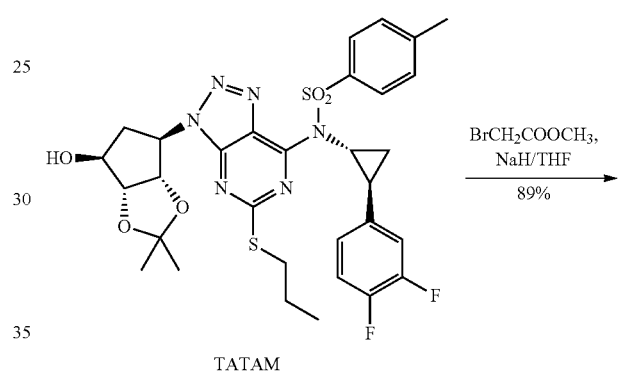

TATAM

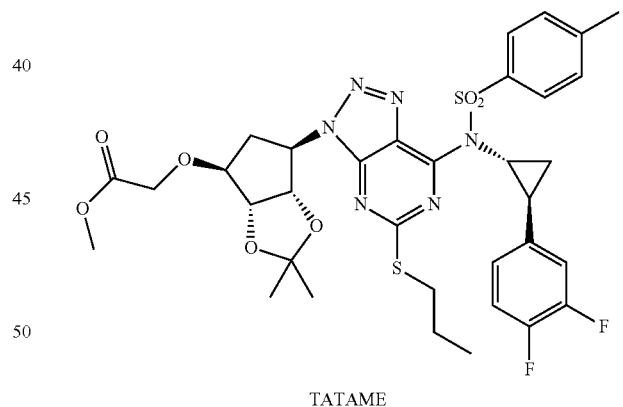

TATAME

To a solution of TATAM (3.31 g, 5 mmol) in dry THF (20 mL) 60% NaH (0.35 g, 8.75 mmol) was added at −20° C. and stirred for 20 min, then methyl bromoacetate (0.83 mL, 8.75 mmol) was added. The resulting reaction mixture was stirred at −20° C. for 18 h. Acetic acid (0.5 mL) was added slowly followed by water (50 mL). The product was extracted with MTBE (50 mL), extract washed with water (3×50 mL) and and concentrated to give a crude product, which was then purified by chromatography (SiO$_2$, hexane:EtOAc) to give the title compound as an amorphous solid (3.30 g, 89% yield): $^{19}$F NMR (CDCl$_3$) δ=−141.83 (m, 1F), −138.9 (m, 1F).

Example 34

Preparation of 2-(((3aR,4S,6R,6aS)-6-(7-(((1R,2S)-2-(3,4-difluorophenyl)cyclopropyl)amino)-5-(propylthio)-3H-[1,2,3]triazolo[4,5-c]pyrimidin-3-yl)-2,2-dimethyltetrahydro-3aH-cyclopenta[d][1,3]dioxol-4-yl)oxy)ethanol (CPATAMA)

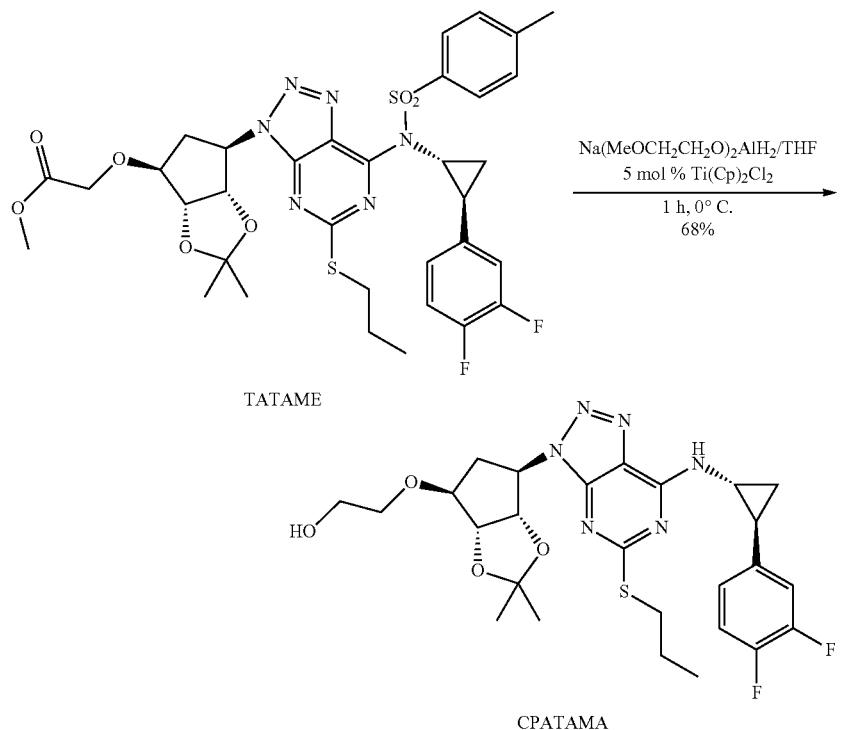

To a solution of TATAME (370 mg, 0.5 mmol) and titanocene dichloride (6 mg, 5 mol %) in THF (5 mL) stirring on an ice bath was added sodium bis(2-methoxyethoxy)aluminumhydride (3.5 M solution in toluene, 0.36 mL, 1.25 mmol). The mixture was stirred for 1 h in an ice bath and then 2 h at about 25° C. The reaction mixture was poured into 0.1 M NaOH(aq) (50 mL), extracted with MTBE (50 mL), the extract washed with water (2×50 mL), concentrated and the residue purified by chromatography (SiO$_2$, hexane:EtOAc) to give the title compound as a resinous product (0.19 g, 68% yield).

The invention claimed is:

1. A process for the preparation of a compound of formula Va or Vb

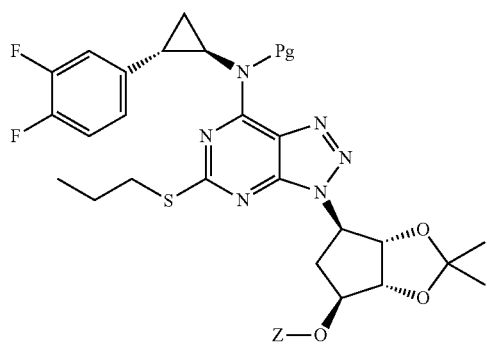

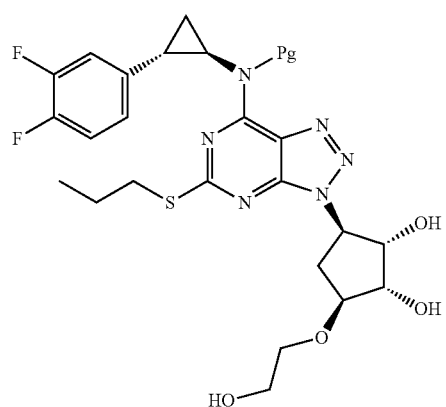

wherein Pg is an amino protecting group, and Z is hydrogen, hydroxyethyl or a group convertible to hydroxyethyl, the process comprising the steps of:
(i) reacting a compound of formula II'

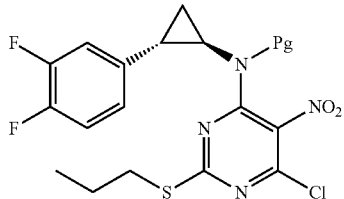

wherein Pg is defined as above, with a compound of the formula VI or VII

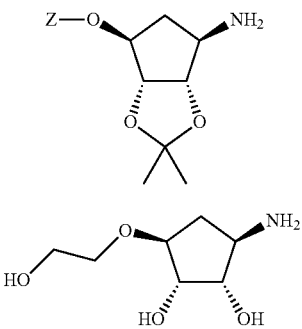

VI

VII wherein Z is defined as above, to obtain a compound of formula IIIa' or IIIb', respectively

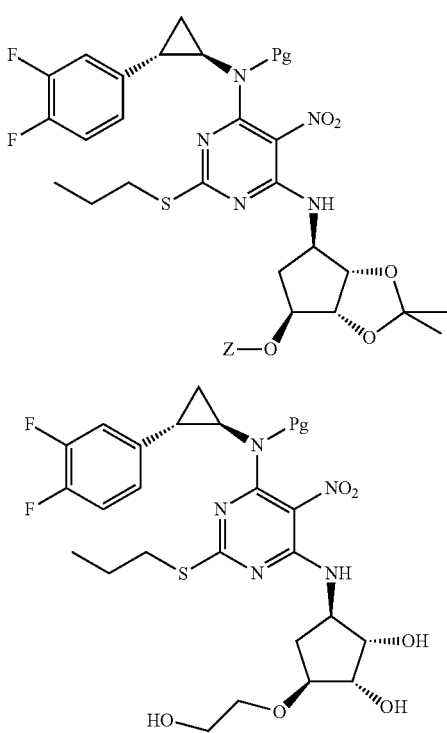

IIIa'

IIIb' wherein Pg and Z are as defined above,
(ii) reducing the nitro group in the compound of formula IIIa' or IIIb' to an amino group to obtain a compound of formula IVa' or IVb', respectively,

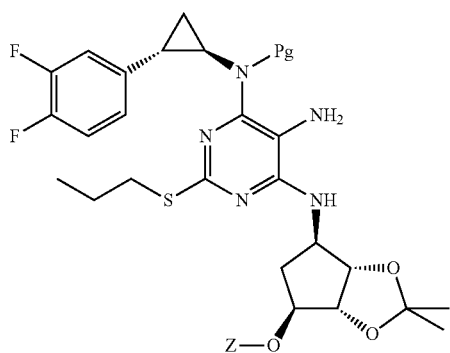

IVa'

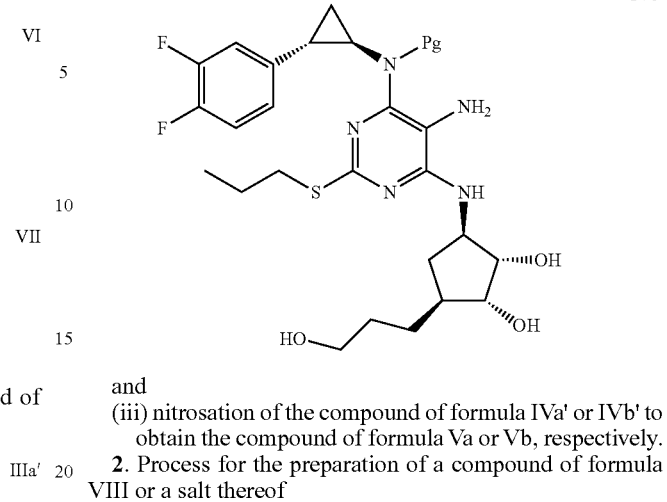

IVb' and
(iii) nitrosation of the compound of formula IVa' or IVb' to obtain the compound of formula Va or Vb, respectively.

2. Process for the preparation of a compound of formula VIII or a salt thereof

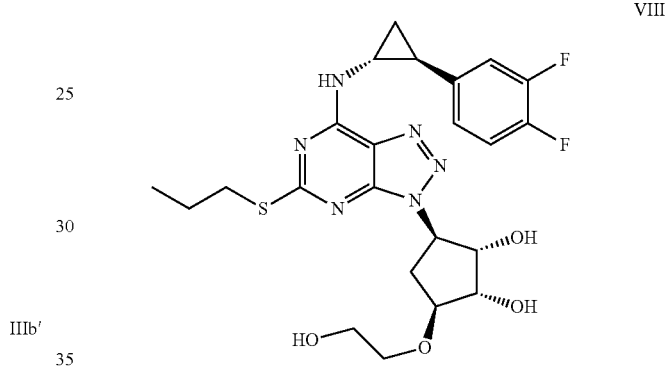

VIII comprising the steps of:
(i) preparing a compound of formula Va, Va' or Vb according to claim 1

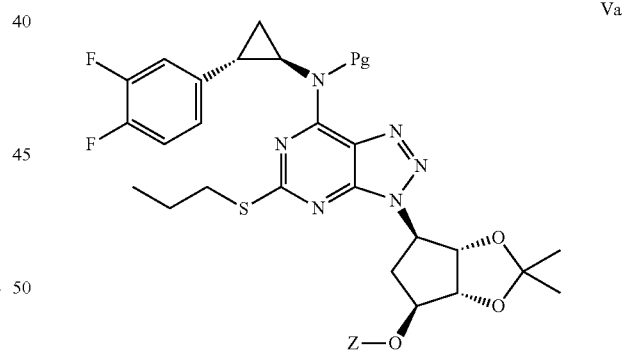

Va

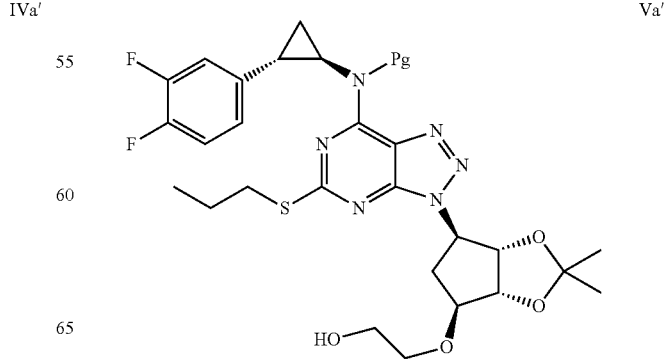

Va'

-continued

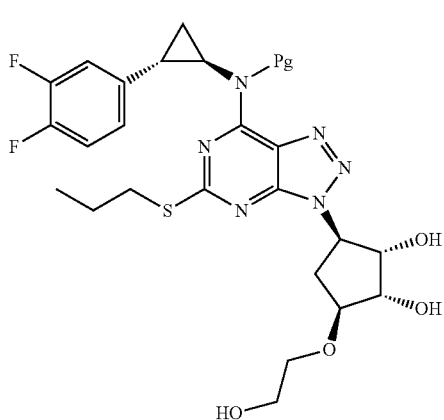

Vb wherein Pg and Z are as defined above, wherein if Z in the compound of formula Va is hydrogen or a group convertible to hydroxyethyl, a hydroxyethyl group is introduced to obtain a compound of formula Va', (ii) carrying out deprotection reaction(s) to remove Pg and in the compound of formula Va or Va' deprotection reaction(s) of the vicinal hydroxyl protecting group at the pentane ring, respectively, (iii) optionally forming a salt of the compound of formula VIII.

3. Process for the preparation of a pharmaceutical composition comprising a compound of formula VIII or a salt thereof

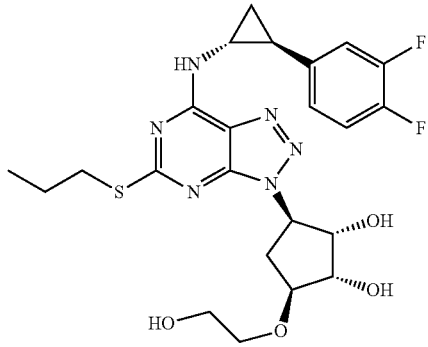

VIII comprising the steps of:
(i) preparing a compound of formula VIII or a salt thereof according to claim 2, and
(ii) mixing the compound of formula VIII or a salt thereof with a pharmaceutically acceptable carrier and/or excipient.

* * * * *